United States Patent
French et al.

(10) Patent No.: US 6,749,432 B2
(45) Date of Patent: Jun. 15, 2004

(54) EDUCATION SYSTEM CHALLENGING A SUBJECT'S PHYSIOLOGIC AND KINESTHETIC SYSTEMS TO SYNERGISTICALLY ENHANCE COGNITIVE FUNCTION

(75) Inventors: Barry J. French, Bay Village, OH (US); Kevin R. Ferguson, Avon Lake, OH (US)

(73) Assignee: Impulse Technology LTD, Westlake, OH (US)

(*) Notice: Subject to any disclaimer, the term of this patent is extended or adjusted under 35 U.S.C. 154(b) by 0 days.

(21) Appl. No.: 10/128,394

(22) Filed: Apr. 22, 2002

(65) Prior Publication Data

US 2003/0077556 A1 Apr. 24, 2003

Related U.S. Application Data

(63) Continuation of application No. PCT/US00/41390, filed on Oct. 20, 2000.
(60) Provisional application No. 60/160,571, filed on Oct. 20, 1999.

(51) Int. Cl.[7] .............................. G09B 9/00; G09B 7/00
(52) U.S. Cl. ........................ 434/247; 434/322; 434/362
(58) Field of Search ................................ 434/219, 247, 434/248, 249, 250, 251, 252, 253, 254, 255, 256, 257, 258, 262, 322, 323, 236, 362

(56) References Cited

U.S. PATENT DOCUMENTS

| | | | | |
|---|---|---|---|---|
| 4,948,371 A | * | 8/1990 | Hall | 434/21 |
| 5,518,402 A | * | 5/1996 | Tommarello et al. | 434/226 |
| 5,577,981 A | * | 11/1996 | Jarvik | 482/4 |
| 5,807,114 A | * | 9/1998 | Hodges et al. | 434/236 |
| 5,989,157 A | * | 11/1999 | Walton | 482/4 |
| 6,012,926 A | * | 1/2000 | Hodges et al. | 434/236 |
| 6,050,822 A | * | 4/2000 | Faughn | 434/11 |
| 6,066,075 A | * | 5/2000 | Poulton | 482/8 |
| 6,097,927 A | * | 8/2000 | LaDue | 434/308 |
| 6,098,458 A | * | 8/2000 | French et al. | 73/379.04 |
| 6,152,854 A | * | 11/2000 | Carmein | 482/4 |
| 6,159,100 A | * | 12/2000 | Smith | 463/42 |
| 6,308,565 B1 | * | 10/2001 | French et al. | 73/379.04 |
| 6,425,764 B1 | * | 7/2002 | Lamson | 434/236 |
| 6,430,997 B1 | | 8/2002 | French et al. | |

FOREIGN PATENT DOCUMENTS

| | | |
|---|---|---|
| EP | 0 959 444 | 11/1999 |
| WO | 97/17598 | 5/1997 |
| WO | 98/07129 | 2/1998 |
| WO | 99/07153 | 2/1999 |
| WO | 99/44698 | 9/1999 |

OTHER PUBLICATIONS

International Search Report, Application No. PCT/US00/41390, Filing Date: Oct. 20, 2000.

* cited by examiner

*Primary Examiner*—John Edmund Rovnak
(74) *Attorney, Agent, or Firm*—Renner, Otto, Boisselle & Sklar, LLP

(57) ABSTRACT

An interactive educational system includes a tracking system for determining changes in an overall physical location of a student, and a display for displaying cues for the student to engage in full-body motion and to engage in an interactive cognitive learning task. An educational method includes prompting a student to engage in an interactive cognitive learning task which involves full body motion, thereby enabling the student to reach the enhanced learning state which results from elevated metabolic rate, and synergistically engaging the student's kinesthetic learning facilities.

18 Claims, 29 Drawing Sheets

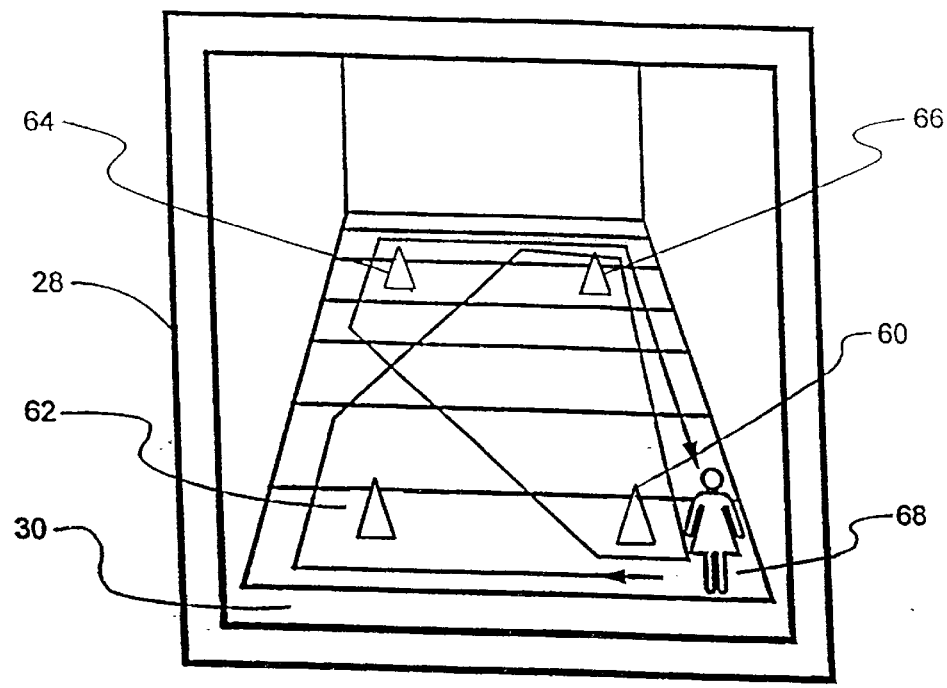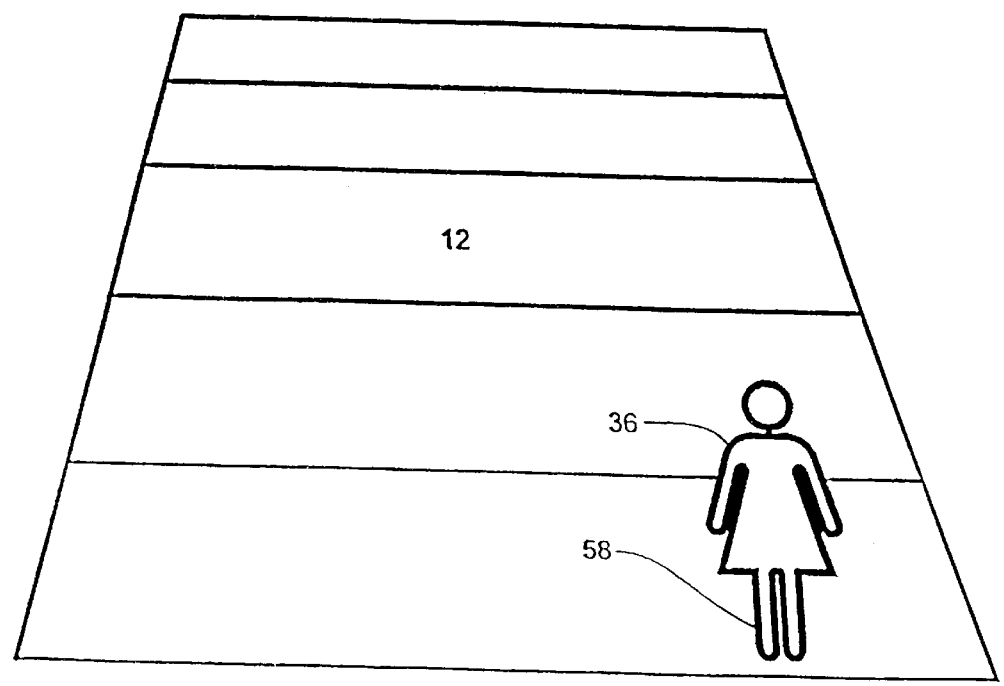
FIG. 4

EDUCATION SYSTEM CHALLENGING A SUBJECT'S PHYSIOLOGIC AND KINESTHETIC SYSTEMS TO SYNERGISTICALLY ENHANCE COGNITIVE FUNCTION

This application is a continuation of International Application No. PCT/US00/41390, filed Oct. 20, 2000, which has been published in English as WO 01/29799, and which claims priority from U.S. Provisional Application No. 60/160,571 filed Oct. 20, 1999.

TECHNICAL FIELD OF THE INVENTION

The present invention relates to an education system for engaging a student in a kinesthetic learning process. Specifically, the invention relates to an education system utilizing a wireless position tracker for continuously tracking and determining a student's position during movement in a defined physical space.

BACKGROUND OF THE INVENTION

Some learners benefit from education utilizing kinesthetic processes in that they learn better when the learning task involves movement that enables manipulation of objects. Such kinesthetic learners preferentially involve their whole bodies in their activities. For such individuals the educational experience is enhanced by use of educational activities that involve physical movement, such as whole-body movement. Even for students who do not learn best by kinesthetic methods, learning is often enhanced through multisensory experiences that combine body motion with traditional visual and auditory methods of delivering information.

In particular, children often learn most effectively when they have to actively "grapple" with information and have their "hands on" the materials. Indeed, many children learn best through direct experience and experimentation.

Cognitive research reiterates the significant value of children's play to their cognitive and motor development. In such play children in essence learn effectively through observation and direct manipulation of their environments. It is expected that brain development is enhanced by simultaneously engaging different cognitive functions simultaneously. Such simultaneous engagement of different cognitive functions is particularly useful for learning and retaining educational material. For instance a student that reads material aloud engages both auditory and visual cognitive functions, and may be expected to retain the material better than if exposed to it only visually (through reading silently), or auditorially (through having the material read to him or her).

From the above it is seen that education or learning is enhanced by engaging multiple cognitive functions, including kinesthetic learning.

SUMMARY OF THE INVENTION

An interactive educational system includes a tracking system for determining changes in an overall physical location of a student, and a display for displaying cues for the student to engage in full-body motion and to engage in an interactive cognitive learning task. An educational method includes prompting a student to engage in an interactive cognitive learning task which involves full body motion, thereby enabling the student to reach the enhanced learning state which results from elevated metabolic rate, and synergistically engaging the student's kinesthetic learning facilities.

According to an aspect of the invention, an educational method includes engaging a student in cognitive learning tasks while the student's metabolic rate is elevated.

According to another aspect of the invention, an educational method includes monitoring a measure of the student's metabolic rate while the student engages in cognitive learning tasks, and adjusting the learning tasks based on the metabolic rate.

According to yet another aspect of the invention, an educational system includes a tracking system for tracking movements of a student engaged in a cognitive learning task which involves full body motion.

According to a further aspect of the invention, an interactive educational system includes a display of a view of a virtual world which includes cognitive learning elements, and a tracking system for tracking movements of a student engaged in a cognitive learning task, movements of the student in a physical world causing manipulation of cognitive learning elements in the virtual world.

According to still further aspect of the invention, a method of educating includes prompting a person to engage in body core movement which elevates the person's metabolic rate; and prompting the person to engage in a cognitive learning task while the person's metabolic rate is elevated, wherein the prompting engage in a cognitive learning task includes displaying a view of a virtual space.

According to another aspect of the invention, an interactive education system includes a continuous tracking system for determining changes in an overall physical location of a person, in a defined physical space; and a computer operatively coupled to the tracking system for updating in real time a player virtual location in a virtual space corresponding to the physical location of the player in the physical space, and for updating a view of the virtual space, wherein the view includes cognitive learning material.

According to yet another aspect of the invention, an interactive education system includes means for elevating a person's metabolic rate by prompting body core movement of the person; and means for engaging the person in a cognitive learning task while the person's metabolic rate is elevated.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

In the annexed drawings:

FIG. 4 is a perspective view of a simulated agility skills protocol for the system of FIG. 1;

DETAILED DESCRIPTION OF THE INVENTION

In the following, a tracking system is described for tracking movement of a person in a defined physical space. Many applications of the tracking system to sports-related activities are described, followed by a description of the application of the tracking system as part of an educational system and method. It will be appreciated that many of the aspects described with respect to sports-related activities may also be utilized with the educational system.

Tracking and Display Systems

Figure 1:
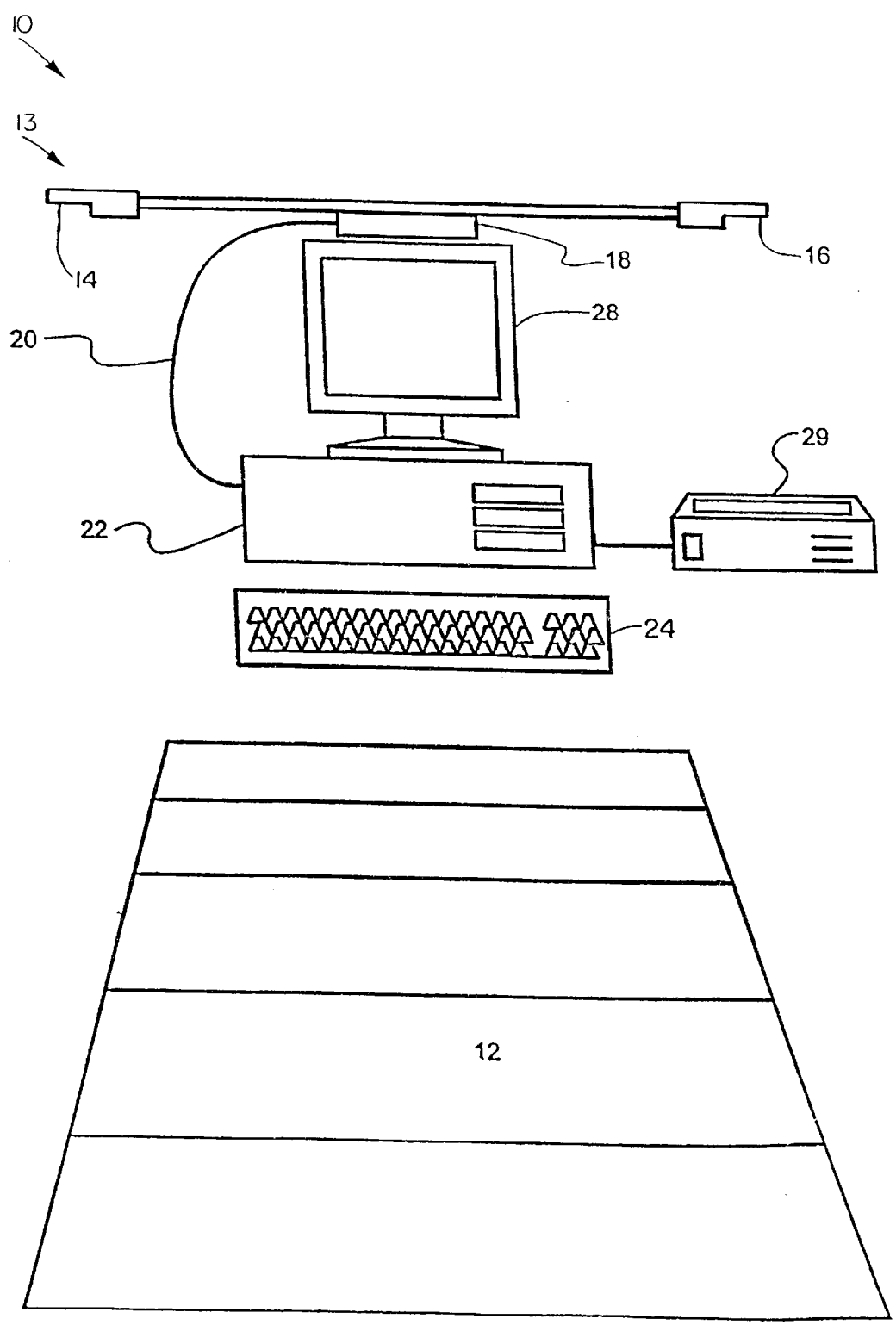
FIG. 1 is a perspective view of a testing and training system in accordance with the invention.

Referring now in detail to the drawings, FIG. 1 shows an interactive, virtual reality testing and training system 10 for assessing movement and agility skills without a confining field. The system 10 comprises a three dimensionally defined physical space 12 in which the player moves, and a wireless position tracking system 13 which includes a pair of laterally spaced wireless optical sensors 14, 16 coupled to a processor 18. The processor 18 provides a data signal along a line 20 via a serial port to a personal computer 22. The computer 22, under control of associated software, processes the data signal and provides a video signal to a large screen video monitor or video display 28. The computer 22 is operatively connected to a printer 29, such as a Hewlett Packard Desk Jet 540 or other such suitable printer, for printing output data related to testing and training sessions. The computer 22 may be coupled to a data inputting device 24. Such a device may be a mouse, trackpad, keyboard, joystick, track ball, touch-sensitive video screen, or the like. The computer 22 may be coupled to the data inputting device 24 by a wired or wireless connection.

Figure 2:
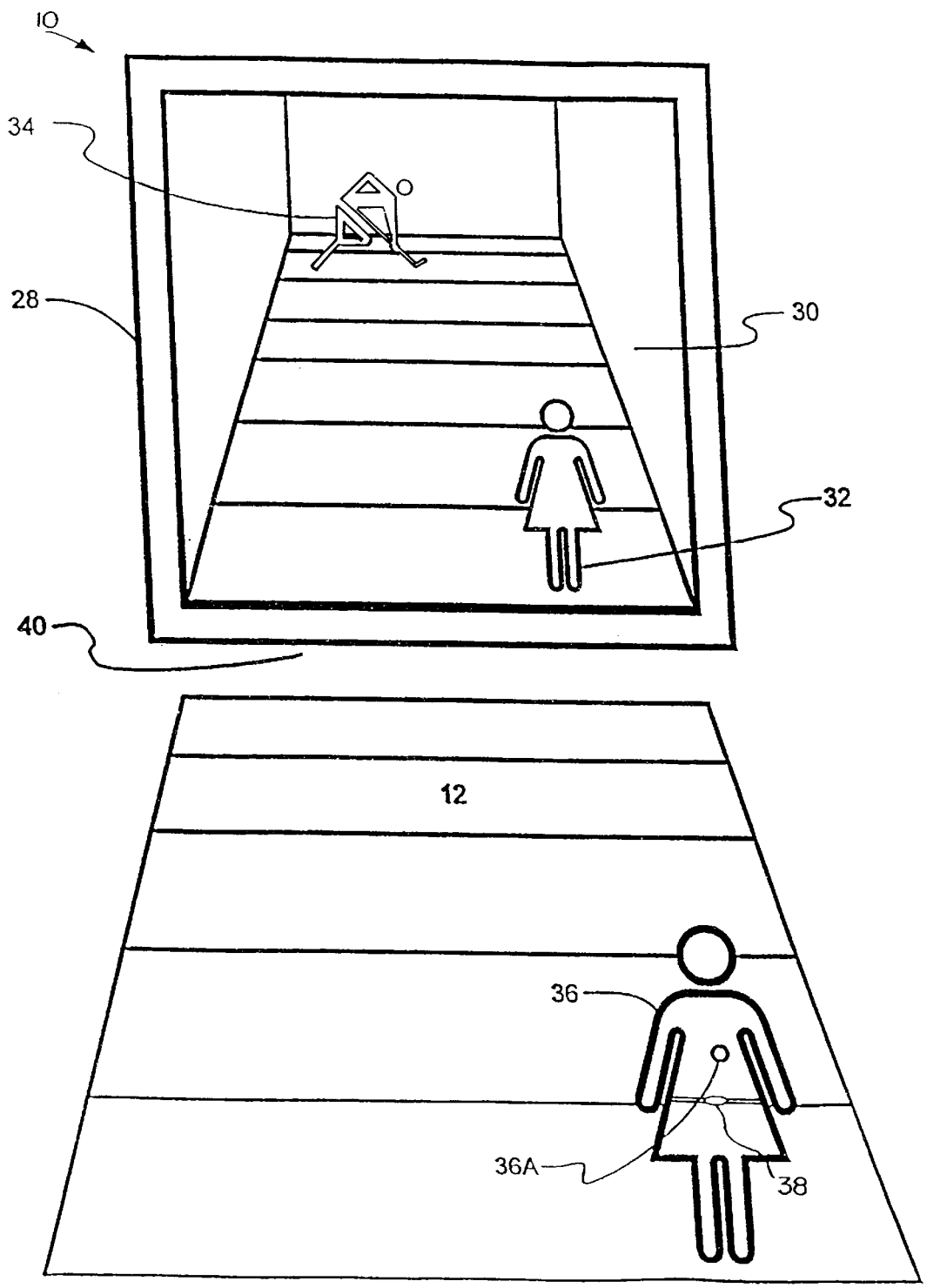
FIG. 2 is a perspective view showing a representative monitor display.

Referring additionally to FIG. 2, the monitor 28 displays a computer generated, defined virtual space 30 which is a scaled translation of the defined physical space 12. The overall position of the player in the physical space 12 is represented and correctly referenced in the virtual space 30 by a player icon 32. The overall position of the player will be understood as the position of the player's body as a whole, which may be the position of the player's center of mass, or may be the position of some part of the player's body.

The player icon 32 may represent a person or a portion thereof. Alternatively it may represent an animal or some other real or imaginary creature or object. The player icon 32 may interact with a protagonist icon 34 representing a protagonist (also referred to as an avatar or virtual opponent) in the performance of varying tasks or games to be described below.

The protagonist icon may be a representation of a person. Alternatively the protagonist icon may be a representation of another object or may be an abstract object such as a shape.

The system 10 assesses and quantifies agility and movement skills by continuously tracking the player in the defined physical space 12 through continuous measurement of Cartesian coordinate positions. By scaling translation to the virtual space 30, the player icon 32 is represented in a spatially correct position and can interact with the protagonist icon 34 such that movement related to actual distance and time required by a player 36 (also known as an athlete or a subject) to travel in the physical space 12 can be quantified. The player icon 32 is at a player virtual location in virtual space, and the protagonist icon 34 is at a protagonist virtual location in virtual space.

The defined physical space 12 may be any available area, indoors or outdoors of sufficient size to allow the player to undertake the movements for assessing and quantifying distance and time measurements relevant to the player's conditioning, sport and ability. A typical physical space 12 may be an indoor facility such as a basketball or handball court where about a 20 foot by 20 foot area with about a 10 foot ceiling clearance can be dedicated for the training and testing. It will be appreciated that the system 10 may be adaptable to physical spaces of various sizes.

Inasmuch as the system is portable, the system may be transported to multiple sites for specific purposes. For relevant testing of sports skills on outdoor surfaces, such as football or baseball, where the player is most relevantly assessed under actual playing conditions, i.e., on a grass surface and in athletic gear, the system may be transported to the actual playing field for use.

The optical sensors 14, 16 and processor 18 may take the form of commercially available tracking systems. Preferably the system 10 uses an optical sensing system available as a modification of the DynaSight system from Origin Instruments of Grand Prairie Tex. Such a system uses a pair of optical sensors, i.e., trackers, mounted about 30 inches apart on a support mast centered laterally with respect to the defined physical space 12 at a distance sufficiently outside the front boundary 40 to allow the sensors 14, 16 to track movement in the desired physical space. The processor 18 communicates position information to an application program in a host computer through a serial port. The host computer is provided with a driver program available from Origin which interfaces the DynaSight system with the application program.

The sensors 14, 16, operating in the near infrared frequency range, interact with a passive or active reflector or beacon 38 worn by the player 36. The reflector or beacon 38 (collectively herein referred to as a marker) is preferably located at or near the center of mass of the player 36, although it may be located elsewhere relative to the player. For example the reflector or beacon may be attached to a belt which is worn about the waist of the player. The sensors report positions of the reflector or beacon 38 in three dimensions relative to a fiducial mark midway between the sensors. The fiducial mark is the origin of the default coordinate system.

Another suitable tracking system is the MacReflex Motion Measurement System from Qualisys.

As is evident, a skilled person will recognize that many other suitable tracking systems may be substituted for or used in addition to the optical tracking systems described above. For example, known electromagnetic, acoustic and video/optical technologies may be employed. Sound waves such as ultrasonic waves, or light waves in the visible or infrared spectra, may be propagated through the air between the player and the sensor(s) and utilized to track the player. Such waves may be transmitted by an external source and reflected off of a passive reflector worn by the player. It will be understood that such waves may reflect off of the player or his or her clothing, dispensing with the need for the player to wear a passive sensor.

Alternatively, the player may wear an active emitter which emits sound or light waves. Such an emitter may be battery operated, and may continuously emit sound or light waves when turned on. Alternatively, the emitter may emit waves only in response to an external signal or stimulus.

Multiple reflecting or emitting elements may be incorporated in a single reflector or emitter. Such multiple elements may be used to aid in tracking the location of the player. In an exemplary embodiment, three spaced-apart infrared emitting elements are incorporated in an emitter worn around the player's waist. The emitting elements are activated intermittently on a rotating basis at a known frequency. Information on the relative timing of the signals received from the various emitting elements allows the player to be tracked.

Alternatively or in addition such multiple elements may be used to track the orientation of the player's body as well as his or her position. For example, twisting of the player's body may be detected independent of the movement of the player by relative motion of the elements.

It will be appreciated further that one or more cameras or other image capturing devices may be used to continuously view the physical space. Image analysis techniques may be used to determine the position of the player from these images. Such image analysis techniques may for example include edge tracking techniques for detecting the location of the player relative to the background, and tracking of an item worn by the player, such a distinctively colored badge.

Any of the above such systems should provide an accurate determination of the players location in at least two coordinates and preferably three.

As is evident from the foregoing, tracking means used in the invention include all such tracking systems described above which are suitable for use in the invention.

In a particular embodiment, the position-sensing hardware tracks the player 36 in the defined physical space 12 at a sample rate of 500 Hz, with an absolute position accuracy of one inch or better in all dimensions over a tracking volume of approximately 432 cubic feet (9 ft. W×8 ft D×6 ft. H).

In the described embodiment, the player icon 32 is displayed on the monitor 28 in the corresponding width, lateral x axis, height, y axis and depth, or fore-aft z axis and over time t, to create a four dimensional space-time virtual world. For tasks involving vertical movement, tracking height, y axis, is required. The system 10 determines the coordinates of the player 36 in the defined physical space 12 in essentially real time and updates current position without any perceived lag between actual change and displayed change in location in the virtual space 30, preferably at an update rate in excess of about 20 Hz. A video update rate approximately 30 Hz, with measurement latency less than 30 milliseconds, has been found to serve as an acceptable, real-time, feedback tool for human movement. However, it is more preferable for the update rate be even higher, in excess of about 50 Hz, or even more preferably in excess of 70 Hz.

The monitor 28 should be sufficiently large to enable the player to view clearly the virtual space 30. The virtual space 30 is a spatially correct representation of the physical space as generated by the computer 22. For a 20 foot by 20 foot working field, a 27-inch diagonal screen or larger allows the player to perceptively relate to the correlation between the physical and virtual spaces. An acceptable monitor is a Mitsubishi 27" Multiscan Monitor. It will be appreciated that other display devices, such as projection displays, liquid crystal displays, or virtual reality goggles or headsets, may also be employed to display a view of the virtual reality space.

The computer 22 receives the signal for coordinates of the player's location in the physical space 12 from the processor 18 and transmits a signal to the monitor 28 for displaying the player icon in scaled relationship in the virtual space 30. An acceptable computer is a Compaq Pentium PC. Other computers using a Pentium processor, a Pentium II processor, or other suitable processors would also be acceptable. In other words, the player icon 32 typically will be positioned in the computer-generated virtual space 30 at the x, y, z coordinates corresponding to the player's actual location in the physical space 12. However, it will be appreciated that the player icon may be placed in the virtual space at location(s) other than those corresponding to the player's location in physical space.

As the player 36 changes location within the physical space 12, the player icon 32 is repositioned accordingly in the virtual space 30. The repositioning is taken into account in an updated view fed to the display 28. In addition, past positions of the player icon 32 may be represented in the display. For example, "ghosts", reduced brightness images of the player icon, may be displayed at locations where the player has recently been. This gives an indication of the recent path of motion of the player. Alternatively, the recent motion of the player may be indicated by a line trace which fades in intensity over time. Such indications may be used only for certain parts of a player's motion—for example only for jumps or leaps.

The computer 22 may retain a record of some or all of the data regarding the player's position on a data storage device such as hard disk or a writeable optical disk. This retained data may be in raw form, with the record containing the actual positions of the player at given times. Alternatively, the data may be processed before being recorded, for example with the accelerations of the player at various times being recorded.

To create tasks that induce the player 36 to undertake certain movements, a protagonist icon 34 is displayed in the computer-generated virtual space 30 by the computer software. The protagonist icon 34 serves to induce, prompt and lead the player 36 through various tasks, such as testing and training protocols in an interactive game-like format that allows the assessment and quantification of movement and agility skills related to actual distance traveled and elapsed time in the physical space 12 to provide physics-based vector and scalar information.

The protagonist icon 34 may be interactive with the player 36. For example, an interception task allows the player icon 32 and the protagonist icon 34 to interact until the two icons occupy the same or a similar location, whence the task ends. An evasion task, on the other hand, involves interaction of the player icon 32 and the protagonist icon 34 until the two icons have attained a predetermined separation. As used herein the protagonist icon is the graphic representation with which the player interacts, and defines the objective of the task. Other collision-based icons, such as obstacles, barriers, walls and the like may embellish the task, but are generally secondary to the objective being defined by the protagonist.

The protagonist icon 34 may have varying attributes. For example, the protagonist icon may be dynamic, rather than stationary, in that its location changes with time under the control of the software thereby requiring the player to determine an w ever changing interception or evasion path to complete the task.

Further, the protagonist icon can be intelligent, programmed to be aware of the player's position in the computer-generated virtual space 30 and to intercept or evade according to the objectives of the task. Such intelligent protagonist icons are capable of making course correction changes in response to changes in the position of the player icon 32 in much the same manner as conventional video games wherein the targets are responsive to the icon under the player's control, the difference being that the player's icon does correspond to the player's actual position in a defined physical space.

The foregoing provides a system for assessing movement skills and agility skills. Movement skills are generally characterized in terms of the shortest time to achieve the distance objective. They can be further characterized by direction of movement with feedback, quantification and assessment being provided in absolute units, i.e., distance/time unit, or as a game score indicative of the player's movement capabilities related to physics-based information including speed, velocity, acceleration, deceleration and displacement. Agility is generally characterized as the ability to quickly and efficiently change body position and direction while undertaking specific movement patterns. The results also are reported in absolute units, with success determined by the elapsed time to complete the task.

Figure 6:
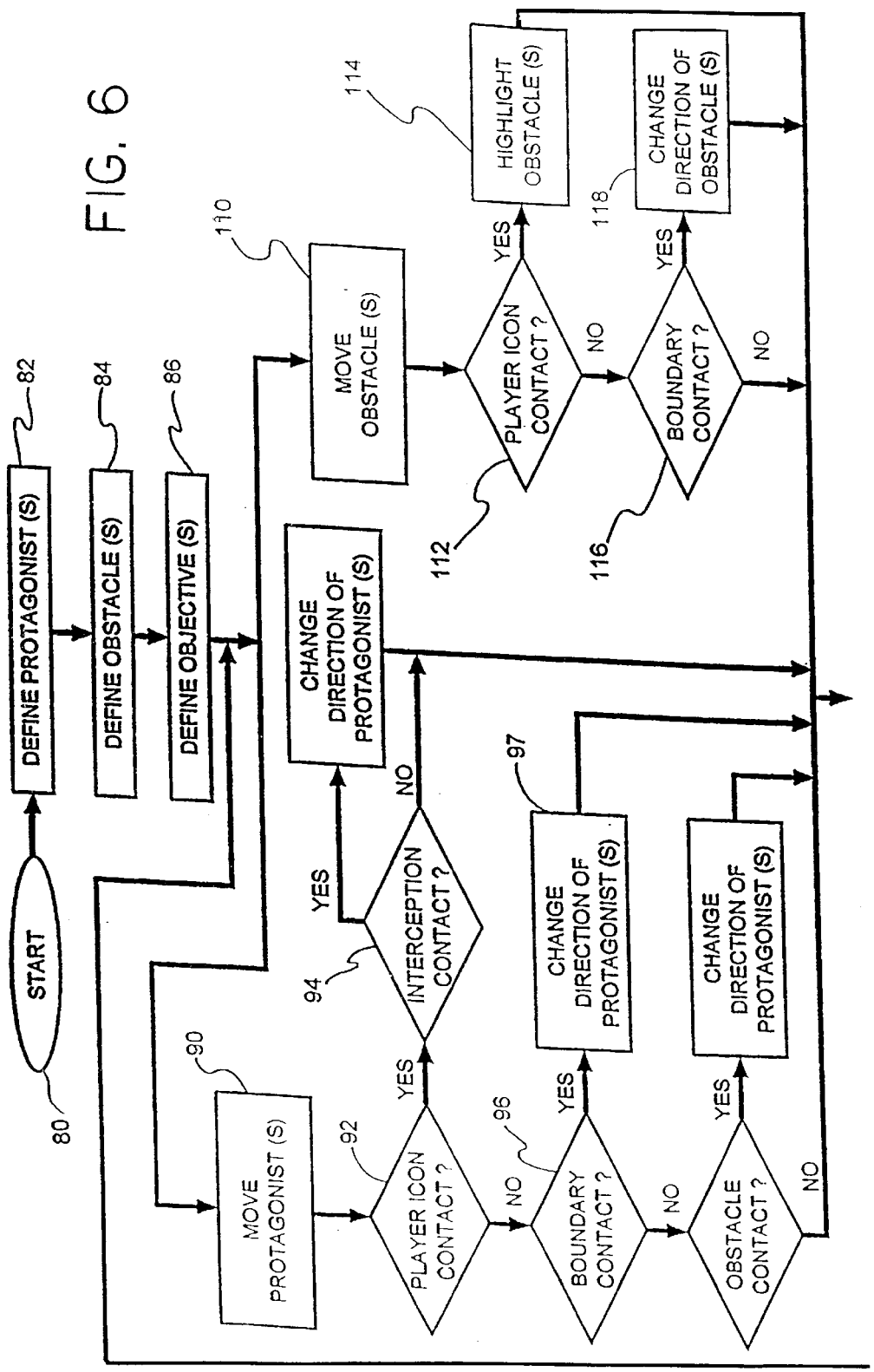
FIGS. 6 and 7 are software flow charts of a representative task for the system.
Figure 7:
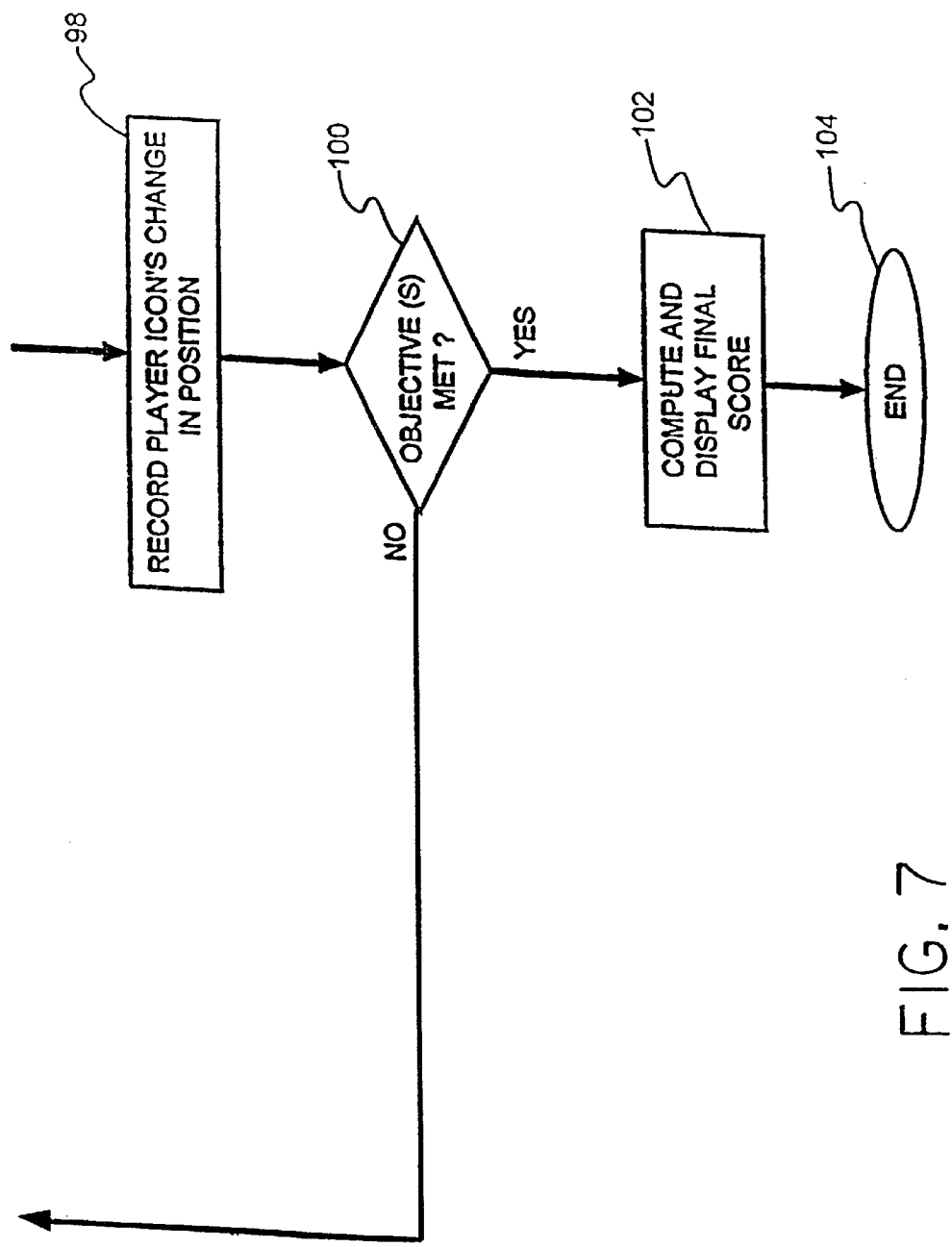

An exemplary software flow chart for the foregoing tasks is shown in FIGS. 6 and 7. At the start 80 of the assessment, the player is prompted to Define Protagonist(s) 82. The player may select the intelligence level, number, speed and size of the protagonists to reside in the selected routine. Thereafter the player is prompted to Define Obstacle(s) 84, i.e., static vs. dynamic, number, speed, size and shape. The player is then prompted to Define Objective(s) 86, i.e., avoidance or interception, scoring parameters, and goals, to complete the setup routine.

To start the task routine, the player is prompted to a starting position for the task and upon reaching this position, the protagonist(s) and the obstacle(s) for the task are generated on the display. The protagonist moves on the display in step 90, in a trajectory dependent on the setup definition. For an interception routine, the player moves in a path which the player determines will result in the earliest interception point with the protagonist in accordance with the player's ability. During player movement, the player icon is generated and continually updated, in scaled translation in the virtual space to the player's instantaneous position in the defined physical space. Movement continues until player contact with the protagonist icon in step 92, resulting in interception in step 94, or until the protagonist contacts a boundary of the virtual space corresponding to the boundary of the defined physical space, 96. In the former case, if interception has occurred, a new protagonist appears on a new trajectory, 97. The player icon's position is recorded, 98, the velocity vectors calculated and recorded, and a score or assessment noted on the display. The system then determines if the task objectives have been met, 100, and for a single task, the final score is computed and displayed, 102, as well as information related to time and distance traveled in completing the task, and the session ends, 104.

In the event the player does not intercept the protagonist icon prior to the latter contacting a virtual space boundary corresponding to the boundary on the defined physical space, the direction of the protagonist is changed dependent on the setup definition, and the pursuit of the protagonist by the player continues as set forth above.

Concurrently with the player pursuit, in the event that obstacles have been selected in the setup definition, the same are displayed, 110, and the player must undertake a movement path to avoid these obstacles. For a single segment task, if the player contacts the obstacle, 112, the obstacle is highlighted, 114, and the routine is completed and scored as described above. In the event a moving obstacle was selected in the setup definition, if the obstacle strikes a boundary, 116, the obstacle's direction is changed, 118, and the task continues.

For a multiple segment task, if the obstacle is contacted, the protagonist's direction changes and the movements continue. Similarly, upon interception for a multiple segment task, a new protagonist trajectory is initiated and the obstacles also may be reoriented. The routine then continues until the objectives of the task have been met and the session completed.

The tasks are structured to require the player to move forward, backward, left and right, and optionally vertically. The player's movement is quantified as to distance and direction dependent on the sampling rate and the update rate of the system. For each sampling period, the change in position is calculated. At the end of the session, these samples are totaled and displayed for the various movement vectors.

For an avoidance task wherein the objective of the session is to avoid a protagonist seeking to intercept the player, the aforementioned is appropriately altered. Thus if the player is intercepted by the protagonist, the session ends for a single segment task and the time and distance related information is calculated and displayed. For multiple segment tasks, the protagonist trajectory has a new origin and the session continues for the defined task until completed or terminated.

Figure 3:
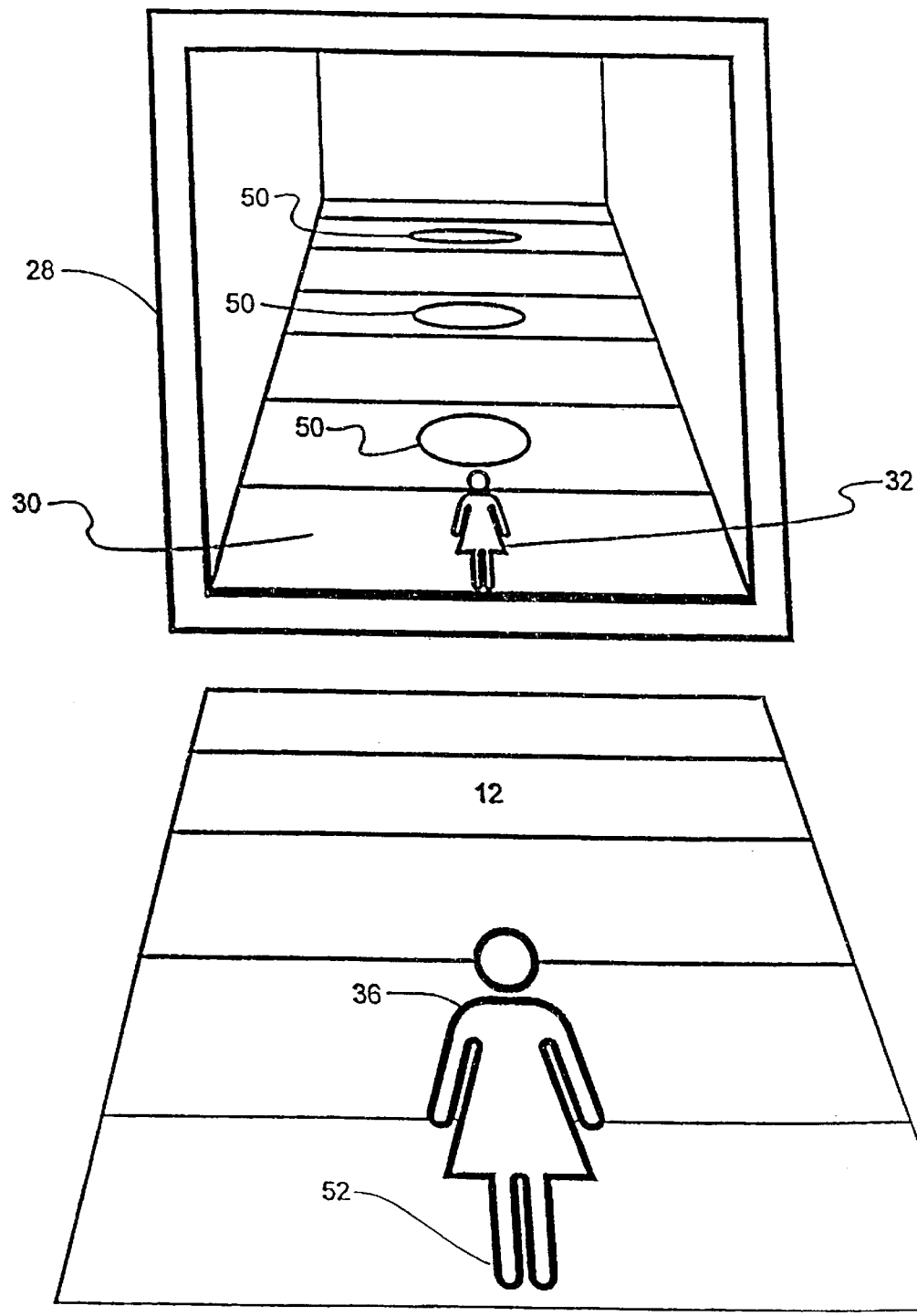
FIG. 3 is a perspective view of simulated movement skills protocol for the system of FIG. 1.

An example of a functional movement skills test is illustrated in FIG. 3 by reference to a standard three hop test. Therein the player 36 or patient stands on one leg and performs three consecutive hops as far as possible and lands on the same foot. In this instance the player icon 32 is displayed at the center of the rear portion of the computer-generated virtual space 30, a position in scaled translation to the position of the player 36 in the defined physical space 12. Three hoops 50, protagonist icons, appear on the display indicating the sequence of hops the player should execute. The space of the hoops may be arbitrarily spaced, or may be intelligent, based on standard percentile data for such tests, or on the best or average past performances of the player.

In one embodiment, the player 36 is prompted to the starting position 52. When the player reaches such position, the three hoops 50 appear representing the 50th percentile hop distances for the player's classification, and after a slight delay the first hoop is highlighted indicating the start of the test. The player then executes the first hop with the player's movement toward the first hoop being depicted in essentially real-time on the display. When the player lands after completion of the first hop this position is noted and stored on the display until completion of the test and the second hoop and third hoop are sequentially highlighted as set forth above. At the end of the three hops, the player's distances will be displayed with reference to normative data.

A test for agility assessment is illustrated in FIG. 4 for a SEMO Agility Test wherein the generated virtual space 30 is generally within the confines of a basketball free throw lane. Four cones 60, 62, 64, 66 are the protagonist icons. As in the movement skills test above, the player 36 is prompted to a starting position 68 at the lower right corner. When the player 36 reaches the starting position in the defined physical space the left lower cone 62 is highlighted and the player side steps leftward thereto while facing the display. After clearing the vicinity of cone 62, the fourth cone 66, diagonally across at the front of the virtual space 30 is highlighted and the player moves toward and circles around cone 66. Thereafter the player moves toward the starting cone 60 and circles the same and then moves to a highlighted third virtual cone 64. After circling the cone 64, cone 66 is highlighted and the player moves toward and circles the cone 66 and then side steps to the starting position 68 to complete the test. In the conventional test, the elapsed time from start to finish is used as the test score. With the present invention, however, each leg of the test can be individually reported, as well as forward, backward and side to side movement capabilities.

As will be apparent from the above embodiment, the system provides a unique measurement of the player's visual observation and assesses skills in a sport simulation wherein the player is required to intercept or avoid the protagonist based on visual observation of the constantly changing spatial relationship with the protagonist. Additionally, excursions in the Y-plane can be quantified during movement as a measure of an optimal stance of the player.

Figure 5:
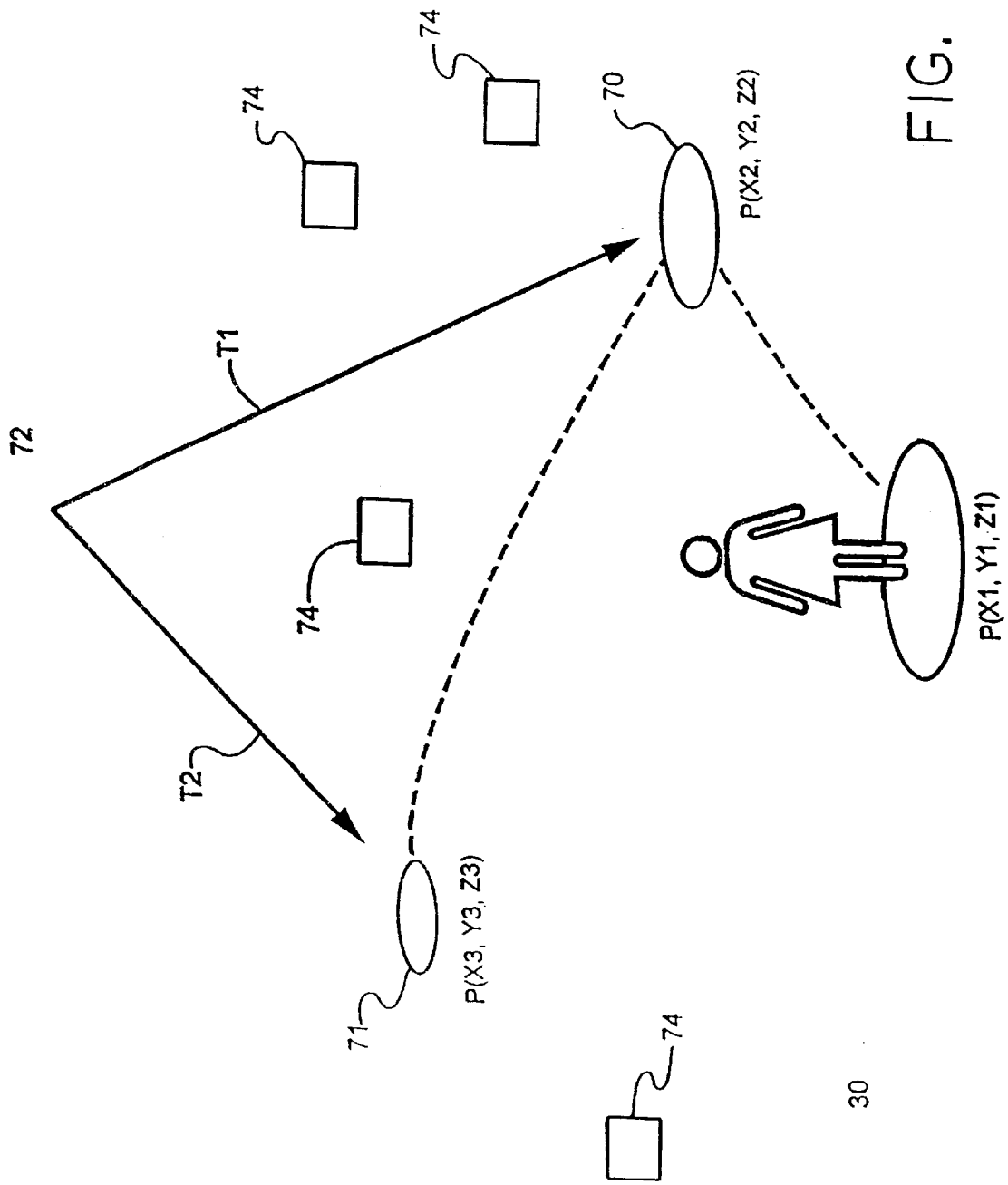
FIG. 5 is a perspective view of a simulated task for the system.

The foregoing and other capabilities of the system are further illustrated by reference to FIG. 5. Therein, the task is to intercept targets 70, 71 emanating from a source 72 and traveling in straight line trajectories T1, T2. The generated virtual space 30 displays a plurality of obstacles 74 which the player must avoid in establishing an interception path with the target 70. The player assumes in the defined physical space a position which is represented on the generated virtual space as position P (X1, Y1, Z1) in accurately scaled translation therewith. As the target 70 proceeds along trajectory T1, the player moves along a personally determined path in the physical space which is indicated by the dashed lines in the virtual space to achieve an interception site coincident with the instantaneous coordinates of the target 70, signaling a successful completion of the first task. This achievement prompts the second target 71 to emanate from the source along trajectory T2. In order to achieve an intercept position for this task, the player is required to select a movement path which will avoid contact or collision with virtual obstacle 74. Thus, within the capabilities of the player, a path shown by the dashed lines is executed in the defined physical space and continually updated and displayed in the virtual space as the player intercepts the protagonist target at position P(X3, Y3, Z3) signaling completion of the second task. The assessment continues in accordance with the parameters selected for the session, at the end of which the player receives feedback indicative of success, i.e., scores or critical assessment based on the distance, elapsed time for various vectors of movement.

Another protocol is a back and forth hop test. Therein, the task is to hop back and forth on one leg over a virtual barrier displayed in the computer-generated virtual space. The relevant information upon completion of the session would be the amplitude measured on each hop which indicates obtaining a height sufficient to clear the virtual barrier. Additionally, the magnitude of limb oscillations experienced upon landing could be assessed. In this regard, the protocol may only measure the vertical distance achieved in a single or multiple vertical jump.

The aforementioned system accurately, and in essentially real time, measures the absolute three dimensional displacements over time of the body's center of gravity when the sensor marker is appropriately located on the player's mass center. Measuring absolute displacements in the vertical plane as well as the horizontal plane enables assessment of both movement skills and movement efficiency.

In many sports, it is considered desirable for the player to maintain a consistent elevation of his center of gravity above the playing surface. Observation of excursions of the player's body center of gravity in the fore-aft (Z) during execution of tests requiring solely lateral movements (X) would be considered inefficient. For example, displacements in the player's vertical (Y) plane during horizontal movements that exceed certain preestablished parameters could be indicative of movement inefficiencies.

In a further protocol using this information, the protagonist icon functions as an aerobics instructor directing the player through a series of aerobic routines. The system can also serve as an objective physiological indicator of physical activity or work rate during free body movement in essentially real time. Such information provides three benefits: (1) enables interactive, computer modulation of the workout session by providing custom movement cues in response to the player's current level of physical activity; (2) represents a valid and unique criteria to progress the player in his training program; and (3) provides immediate, objective feedback during training for motivation, safety and optimized training. Such immediate, objective feedback of physical activity is generally missing in current aerobics programs, particularly in unsupervised home programs.

Quantification of Performance-Related Parameters

In certain embodiments of the present invention, performance-related physical activity parameters related to movement (indicia derived from movement parameters), including calories burned, are monitored and quantified. The repetitive drudgery of conventional stationary exercise equipment that currently measures calories, heart rate, etc. is replaced by the excitement of three-dimensional movement in interactive response to virtual reality challenges presented on the monitor of the inventive system. Excitement is achieved in part by the scaling transformation achieved by the present invention, through which positional changes by the user moving in real space are represented in scaled relationship in the virtual world presented on the monitor.

Performance-related parameters measured and/or quantified by various embodiments of the present invention include those related to (a) determining and training a user's optimal dynamic posture; (b) the relationship between heart rate and physical activity; (c) quantifying quickness, i.e., acceleration and deceleration; and (d) and quantifying energy expenditure during free ranging activities.

It is especially significant that the user's energy expenditure may be expressed as calories burned, inasmuch as this is a parameter of primary concern to many exercisers. One advantage of the present system is that a variety of environments in the virtual world displayed on the monitor can prompt any desired type and intensity of physical activity, achieving activity and energy expenditure goals in an ever-changing and challenging environment, so that the user looks forward to, rather than dreads, exercise, testing, or therapy sessions.

Measurement of motion (movement in three planes) is used to quantify work and energy expenditure. Movement-related quantities (movement parameters) such as force, acceleration, work and power, defined below, are dependent on the rate of change of more elementary quantities such as body position and velocity (the latter of which is also a movement parameter). The energy expenditure of an individual is related to the movement of the individual while performing the invention protocols.

The concept that a complex motion can be considered as a combination of simple bilateral movements in any of three directions is convenient since this approach allows focus on elementary movements with subsequent adding of the effects of these simple components. Such concept relates to the ability to monitor continuously the movement of the individual to measure the resultant energy expenditure.

The ability of this embodiment to accurately measure a subject's movement rests on being able to determine his or her position and velocity at arbitrary points of time. For a given point in time, a position is measured directly. The sampling rate of the position of the individual or player 36 is sufficiently fast to allow accurate measurements to be made at very closely spaced intervals of time. By knowing an individual's position at arbitrary points along its path the velocity can be calculated.

In the present embodiment, positions can be used to determine velocity along a movement path: given the position of the individual at various instances of time, the embodiment can obtain the velocity in several ways. One method is to choose a point and calculate its velocity as being the result of dividing the distance between it and the next point by the time difference associated with those points. This is known as a finite difference approximation to the true velocity. For small spacing between points, it is highly accurate.

If D is the distance between consecutive points and T equal the time period to travel the distance D, then the velocity V is given by the following rate of change formula $$V=D/T,$$

where V has the units of meters per second, m/s.

In three dimensional space, D is computed by taking the change in each of the separate bilateral directions into account. If dX, dY, and dZ represents the positional changes between the successive bilateral directions, then the distance D is given by the following formula $$D=sqrt(dX*dX+dY*dY+dZ*dZ),$$

where "sqrt" represents the square root operation. The velocity can be labeled positive for one direction along a path and negative for the opposite direction. This is, of course, true for each of the bilateral directions separately.

This finite difference approximation procedure can also be used to calculate the acceleration of the object along the path. This is accomplished by taking the change in velocity between two consecutive points and dividing by the time interval between points. This gives an approximation to the acceleration A of the object which is expressed as a rate of change with respect to time as follows $$A=dV/T,$$

where dV is the change in velocity and T is the time interval. Acceleration is expressed in terms of meters per second per second. The accuracy of this approximation to the acceleration is dependent on using sufficiently small intervals between points.

As an alternate to using smaller position increments to improve accuracy, more accurate finite difference procedures may be employed. This embodiment obtains positional data with accuracy within a few centimeters over time intervals of approximately 0.020 seconds, so that errors are assumed to be negligible.

In contrast to the finite difference approach, the positional data could be fitted by spline curves and treated as continuous curves. The velocity at any point would be related to the tangent to the individual's path using derivative procedures of standard calculus. This would give a continuous curve for the velocity from which a corresponding curve could be obtained for the acceleration of the individual.

It will be appreciated that other methods of modeling may be used to provide accurate estimations of velocity and acceleration.

In any case, the determination of the individual's acceleration provides a knowledge of the force F it experiences. The force is related to the mass M of the individual, given in kilograms, and acceleration, by the formula $$F=M*A.$$

This is a resultant formula combining all three components of force and acceleration, one component for each of the three bilateral directions. The international standard of force is a newton which is equivalent to a kilogram mass undergoing an acceleration of one meter per second per second. This embodiment requires that the individual enter body weight prior to playing. (Body weight is related to mass by the acceleration of gravity.)

The effect of each component can be considered separately in analyzing an individual's movement. This is easily illustrated by recognizing that an individual moving horizontally will be accelerated downward due to gravity even as he or she is being decelerated horizontally by air drag. The effects of forces can be treated separately or as an aggregate. This allows one the option to isolate effects or lump effects together. This option provides flexibility in analysis.

Energy and work may be measured in the present invention. The energy expended by an individual in the inventive system can be derived from work. The mechanical work is calculated by multiplying the force acting on an individual by the distances that the individual moves while under the action of force. The expression for work (W) is given by $$W=F*d.$$

The unit of work is a joule, which is equivalent to a newton-meter.

Power P is the rate of work production and is given by the following formula $$P=W/T$$

The standard unit for power is the watt and it represents one joule of work produced per second.

Different individuals performing the same activity expend different amounts of heat due to differences in body mass, gender, and other factors. As indicated above, mechanical work done in an activity is determined in the present invention system by monitoring motion parameters associated with that activity. Total energy expenditure can be derived from known work-to-calories ratios.

A protocol called "Dynamic Posture" represents the athletic stance maintained during sport specific activity that maximizes a player's readiness for a specific task. Examples are the slight crouches or "ready" position of a soccer goalie or a football linebacker.

Testing or training of dynamic posture is achieved by having the user initially assume the desired position and then tracking, in essentially real-time, displacements in the Y (vertical) plane during interactive protocols. Such Y plane displacements accurately reflect vertical fluctuations of that point on the body on which the reflective marker is placed, for example, the hipline, which is often referred to as the Center of Gravity (CG) point.

It may be desirable to determine dynamic posture and train an athlete in obtaining optimal dynamic posture. The optimal dynamic posture during sport-specific activities is determined as follows:

a) A retro-reflective marker is mounted at the athlete's CG point.

b) The invention's computer 22 measures in real-time vertical displacements of the athlete's CG (Y-plane excursions) as he responds to interactive, sport-specific protocols.

c) The invention's computer 22 calculates in essentially real-time the athlete's movement velocities and/or accelerations during performance of sport-specific protocols.

d) The invention calculates the athlete's most efficient dynamic posture defined as that CG elevation that produces maximum velocities and/or accelerations/decelerations for the athlete in the sports-specific protocols.

e) The invention provides numerical and graphical feedback of results.

Once the optimal dynamic posture is determined, training optimal dynamic posture is achieved by the following steps:

a) A retro-reflective marker is mounted at the athlete's CG point.

b) The athlete 36 assumes the dynamic posture that he or she wishes to train.

c) The invention is initialized for this CG position.

d) The invention provides varying interactive movement challenges over sport-specific distances and directions, including unplanned movements, e) Y-plane excursions from the optimal dynamic posture that exceed the pre-set threshold or window will generate real-time feedback of such violations for the user.

f) The invention provides real-time feedback of compliance with the desired dynamic posture during performance of the protocols.

The invention uses unplanned, interactive game-like movement challenges requiring sport-specific responses. The participant will move most effectively during stopping, starting and cutting activities if he assumes and maintains his optimum Center of Gravity (CG) elevation. Additional movement efficiencies are achieved by the player by minimizing CG elevation excursions. The invention is capable of tracking in essentially real-time, the participant's CG elevation by monitoring Y plane displacements. During the training phase, the participant will be provided with real-time feedback of any Y plane excursions exceeding targeted ranges.

The relationship between heart rate and physical activity of the subject during performance of the protocols is also quantified by the present invention. Heart rate is measured by a commercially available wireless (telemetry) device 36A (FIG. 2) in essentially real-time. Conventional cardiovascular exercise equipment attempts to predict caloric expenditure from exercise heart rate. Real time monitoring of heart rate is an attempt to infer the users' level of physical activity. However, as heart rate is affected by factors other than physical activity such as stress, ambient temperature and type of muscular contraction, the ratio or relationship between heart rate and energy expended may be enlightening to the coach, athlete or clinician. For example, physical training lowers the heart rate at which tasks of a given energy cost are performed.

Prior art applications have attempted to measure these two parameters simultaneously in an attempt to validate one of the measurement constructs as a measure of physical activity. In all such cases though, such measurements were not in real-time; they were recorded over time and did not employ position tracking means nor involve interactive protocols used in the inventive system.

In another aspect of the invention, simultaneous assessment and modulation of physical activity and heart rate is achieved as follows:

a) The subject 36 places a retro-reflective marker at his CG point.

b) A wireless heart-rate monitor 36A (FIG. 2) is worn on the subject 36, the monitor 36A in communication in real-time with the computer 22.

c) Subject 36 enters desired target heart-rate range. (This step is optional.)

d) The invention provides interactive, functional planned and unplanned movement challenges (protocols) over varying distances and directions.

e) The invention provides real-time feedback of compliance with selected heart-rate zone during performance of these protocols.

f) The invention provides a graphical summary of the relationship or correlation between heart-rate at each moment of time and free-body physical activity.

The present invention includes assessment and quantification of movement skills such as accelerations and decelerations during unplanned movement protocols over sport-specific distances. Quantification of bi-lateral vector accelerations and decelerations (how well a subject 36 moves left and right) are achieved as follows:

a) A retro-reflective marker is mounted at the athlete's CG point, b) The invention tracks at sufficient sampling rate the athlete's movement in three degrees of freedom during his performance of sport-specific protocols, including unplanned movements over various vector distances, c) The invention calculates in essentially real-time the athlete's movement accelerations and decelerations, d) The invention categorizes each movement leg to a particular vector, e) The invention provides numerical and graphical feedback of bi-lateral performance.

Quantification of the intensity of free-ranging physical activity as expressed in kilocalories per minute, and the total energy expended, is derived from movement data collected as the subject moves in response to prompts from the monitor, personal data such as weight inputted by the subject, and conventional conversion formulae.

During performance of the above protocols, the inventive system can measure the intensity, i.e., strenuousness or energy cost of physical activity during free ranging (functional) activities, expressed in calories per minute, distance traveled per unit of time.

Energy expenditure can be derived from the subject's movement data during performance of free-ranging activities. Well known laboratory instrumentation can be employed to ascertain the coefficient or conversion factor needed to convert work or power or distance derived from the movement data to calories expended. Oxygen uptake, expressed in milliliters per kilogram per minute can determine the caloric expenditure of physical activity and is considered the "gold standard" or reference when evaluating alternative measures of physical activity. The most precise laboratory means to determine oxygen uptake is through direct gas analysis, which would be performed on representative subject populations during their execution of the invention's protocols with a metabolic cart, which directly measures the amount of oxygen consumed. Such populations would be categorized based on age, gender and weight.

Figure 8:
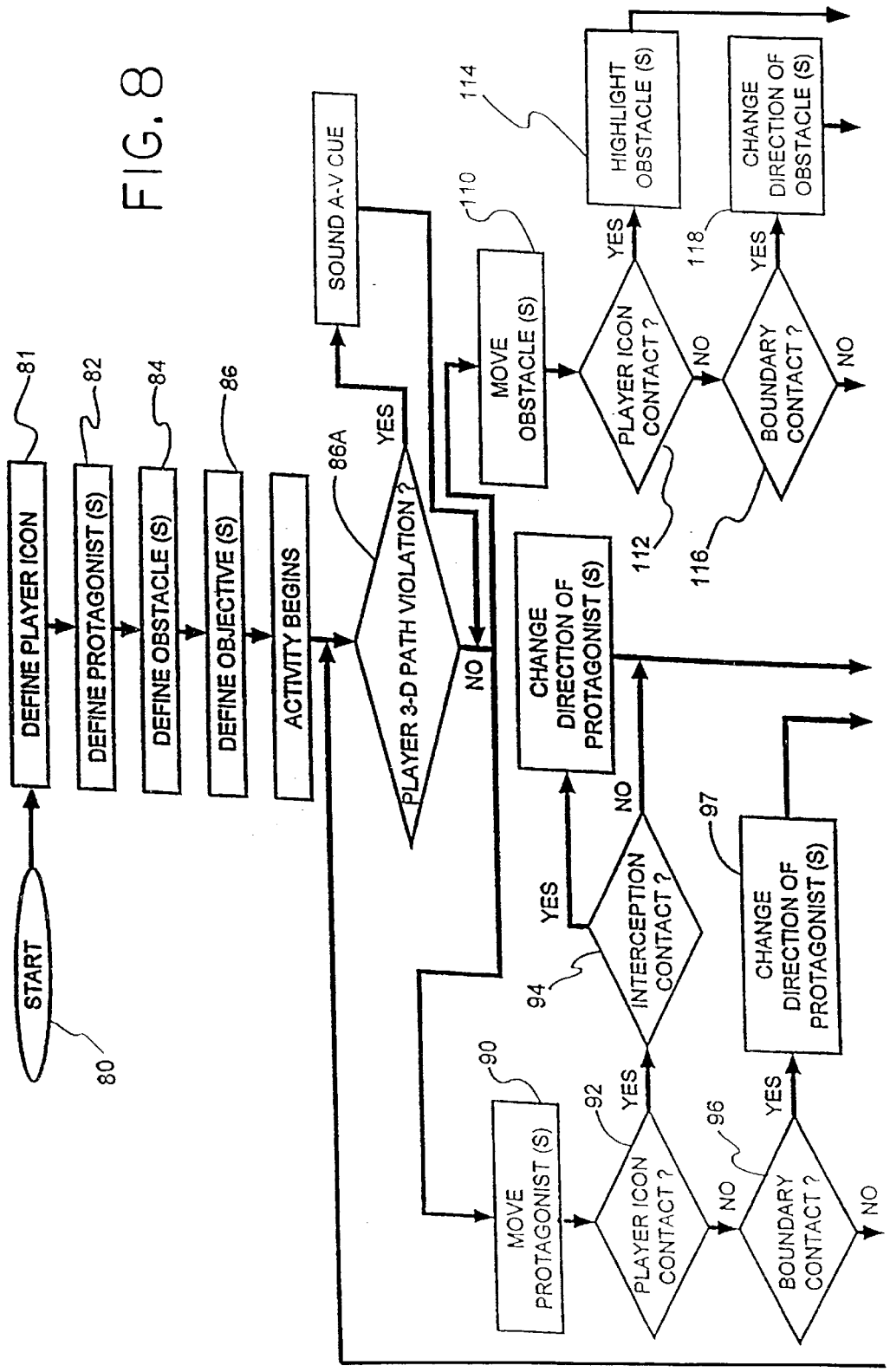
FIGS. 8 and 9 are software flow charts for an embodiment of the invention.
Figure 9:
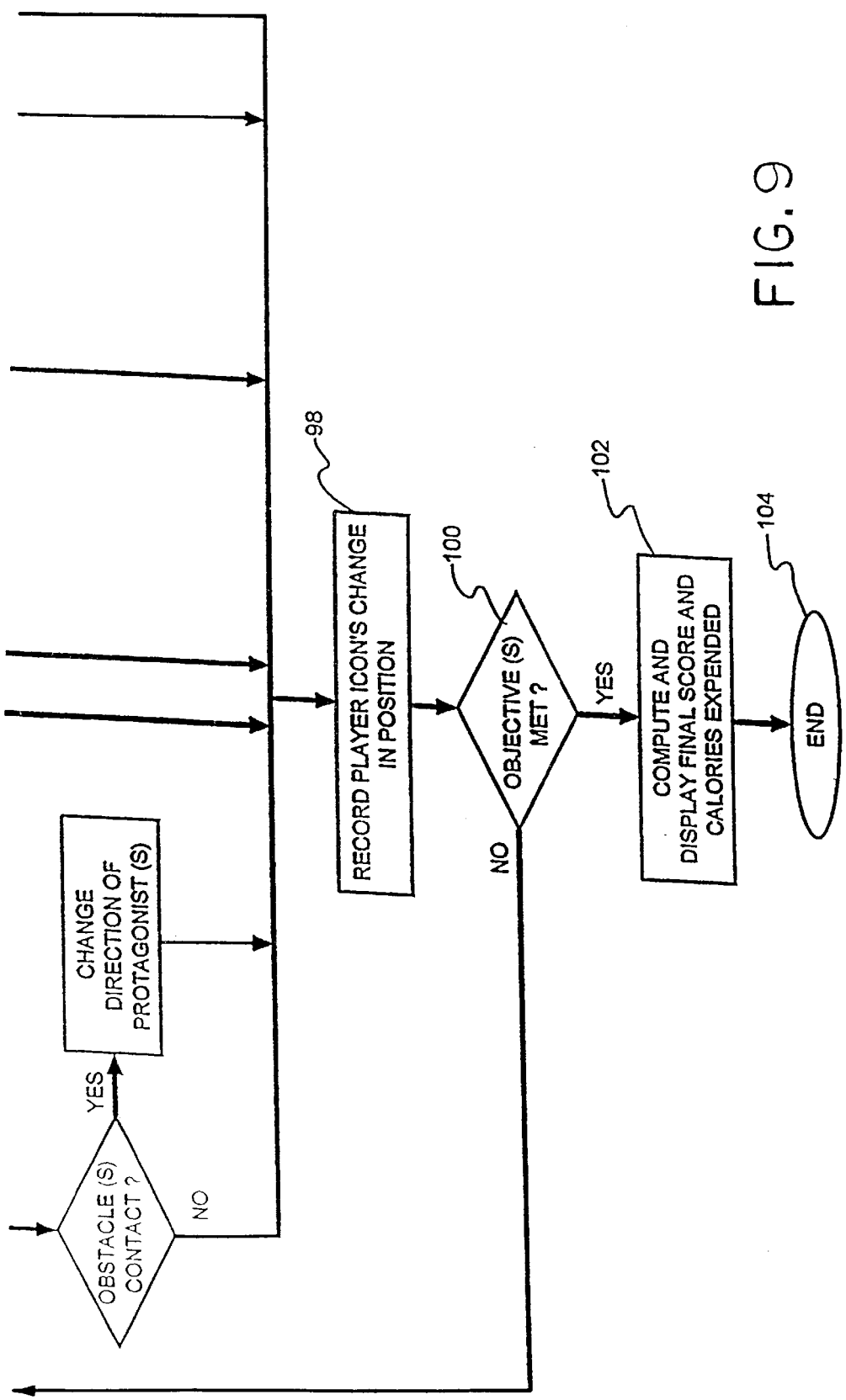

The software flow chart for the tasks of an illustrative embodiment is shown in FIGS. 8 and 9. After the start 80 of the assessment, the user is prompted to DEFINE PLAYER ICON (81). This is when the player's body weight, sex, etc., other information necessary to calculate calories, is entered. The player is prompted to Define Protagonists 82. The player may select the intelligence level, number, speed and size of the protagonists to reside in the selected routine. Thereafter the player is prompted to Define Obstacles 84, i.e., static vs. dynamic, number, speed, size and shape. The player is then prompted to Define Objectives 86, i.e., avoidance or interception, scoring parameters, and goals, to complete the setup routine. As part of DEFINE OBJECTIVES (86), the players 3-D path boundaries should be programmed, the reference frame of play, i.e., 1st person, 3rd person. The player is then prompted by PATH VIOLATION (86A). If yes then provide audio/visual cues alarms and record player's icon change in position else just record player's icon change in position. The OBJECTIVES MET decision block should point here if NO.

To start the task routine, the player is prompted to a starting position for the task and upon reaching this position, the protagonist(s) and the obstacle(s) for the task are generated on the display. The protagonist moves on the display, 90, in a trajectory dependent on the setup definition. For an interception routine, the player moves in a path which the player determines will result in the earliest interception point with the protagonist in accordance with the player's ability. During player movement, the player icon is generated, and continually updated, in scaled translation in the virtual space to the player's instantaneous position in the defined physical space. Movement continues until player contact, 92, and interception, 94, or until the protagonist contacts a boundary of the virtual space corresponding to the boundary of the defined physical space, 96. In the former case, if interception has occurred, a new protagonist appears on a new trajectory, 97. The player icon's position is recorded, 98, the velocity vectors calculated and recorded, and a score of assessment noted on the display. The system then determines if the task objectives have been met, 100, and for a single task, the final score is computed and displayed, 102, and calories burned in calculated, as well as information related to time and distance traveled in completing the task, and the session ends, 104.

In the event the player does not intercept the protagonist icon prior to the latter contacting a virtual space boundary corresponding to the boundary on the defined physical space, the direction of the protagonist is changed dependent on the setup definition, and the pursuit of the protagonist by the player continues as set forth above.

Concurrently with the player pursuit, in the event that obstacles have been selected in the setup definition, the same are displayed, 110, and the player must undertake a movement path to avoid these obstacles. For a single segment task, if the player contacts the obstacle, 112, the obstacle is highlighted, 114, and the routine is completed and scored as described above. In the event a moving obstacle was selected in the setup definition, if the obstacle strikes a boundary, 116, the obstacle's direction is changed, 118, and the task continues.

For a multiple segment task, if the obstacle is contacted, the protagonist's direction changes and the movements continue. Similarly, upon interception for a multiple segment task, a new protagonist trajectory is initiated and the obstacles also may be reoriented. The routine then continues until the objectives of the task have been met, and the session completed.

The tasks are structured to require the player to move forward, backward, left and right, and optionally vertically. The player's movement is quantified as to distance and direction dependent on the sampling rate and the update rate of the system. For each sampling period, the change in position is calculated. At the end of the session, these samples are totaled and displayed for the various movement vectors.

For an avoidance task wherein the objective of the session is to avoid a protagonist seeking to intercept the player, the aforementioned is appropriately altered. Thus if the player is intercepted by the protagonist, the session ends for a single segment task and the time and distance related information is calculated and displayed. For multiple segment tasks, the protagonist trajectory has a new origin and the session continues for the defined task until completed or terminated.

Performance Measurement Constructs

The present invention provides a unique and sophisticated computer sports simulator faithfully replicating the ever-changing interaction between offensive and defensive opponents. This fidelity with actual competition enables a global and valid assessment of an offensive or defensive player's functional, sport-specific performance capabilities. Such assessment may include use of indicia that are or are derived from movement parameter(s). Among these indicia derived from movement parameter(s) are several novel and interrelated measurement constructs which have been derived and rendered operable by specialized position-sensing hardware and interactive software protocols.

Feedback may be provided to the player regarding the measurement constructs. This feedback may take many forms. The feedback may be provided during the interactive session, with there being some effect in the virtual space (and the view) that is a function of one or more of the constructs, for example. Alternatively or in addition, feedback may be provided after the end of one or more interactive sessions.

Figure 10:
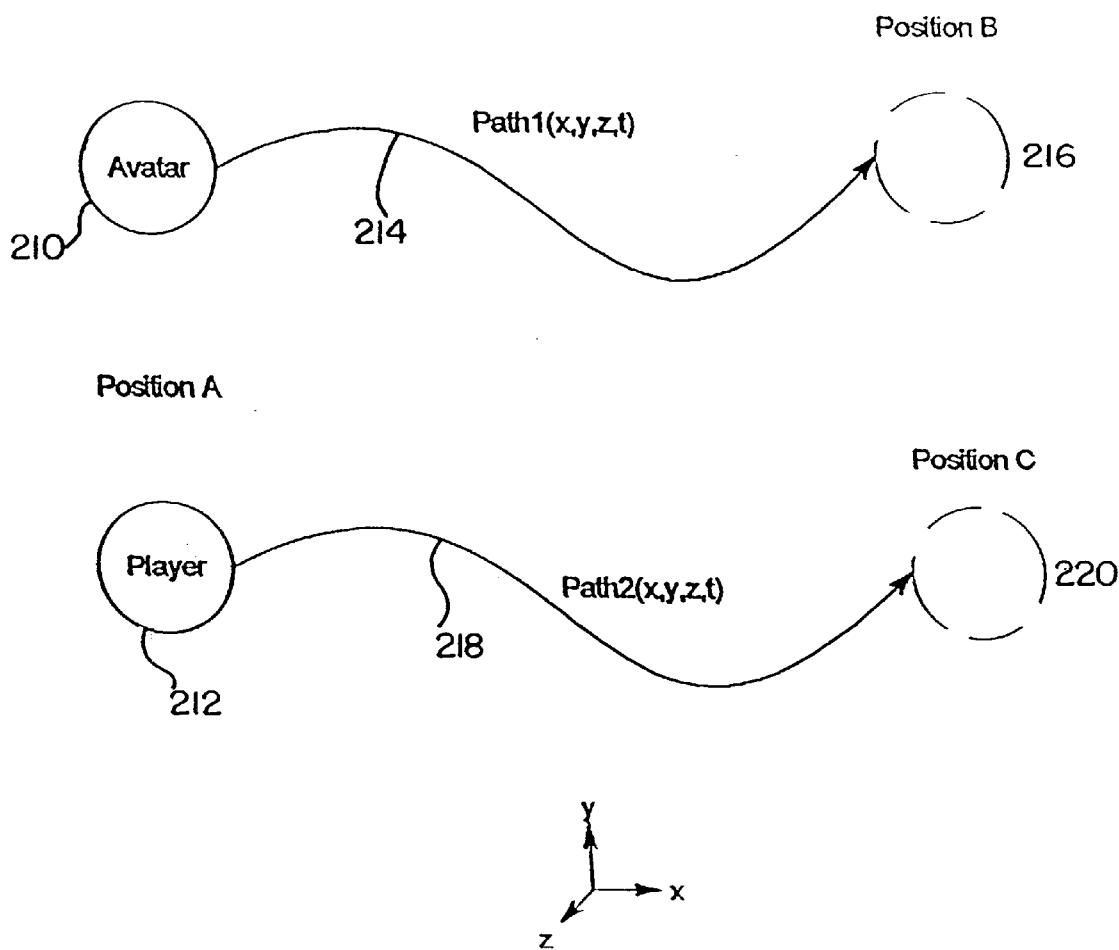
FIG. 10 is a schematic representation of a simulated task that the system executes to determine Compliance.

One of the measurement constructs of the present invention is Compliance, a global measure of the player's core defensive skills is the ability of the player to maintain a synchronous relationship with the dynamic cues that are often expressed as an offensive virtual opponent. The ability to faithfully maintain a synchronous relationship with the virtual opponent is expressed either as compliance (variance or deviation from a perfect synchronous relationship with the virtual opponent) and/or as absolute performance measures of the player's velocity, acceleration and power. An integral component of such a synchronous relationship is the player's ability to effectively change position, i.e., to cut, etc. as discussed below. Referring to FIG. 10, Compliance may be determined as follows:

a) A beacon, a component of the tracking system, is worn at the Player's waist.

b) At Position A software scaling parameters make the virtual opponent 210, coordinates in the virtual environment equivalent to the player's 212 coordinates in the physical environment.

c) The system's video displays the virtual opponent's movement along Path1 (x,y,z,t) 214 as a function of dimensions X, Y and Z, and time (x,y,z,t) to a virtual Position B 216.

d) In response, the Player moves along Path 2 (x,y,z,t) 218 to a near equivalent physical Position C 220. The Player's objective is to move efficiently along the same path in the physical environment from start to finish, as does the avatar in the virtual environment. However, since the virtual opponent typically moves along random paths and the Player is generally not as mobile as the virtual opponent, the player's movement path usually has some position error measured at every sample interval.

e) The system calculates at each sampling interval the Player's new position, velocity, acceleration, and power, and determines the Player's level of compliance characterized as measured deviations from the original virtual opponent 210-Player 212 spacing at position A.

f) The system provides real time numerical and graphical feedback of the calculations of part e.

Figure 11:
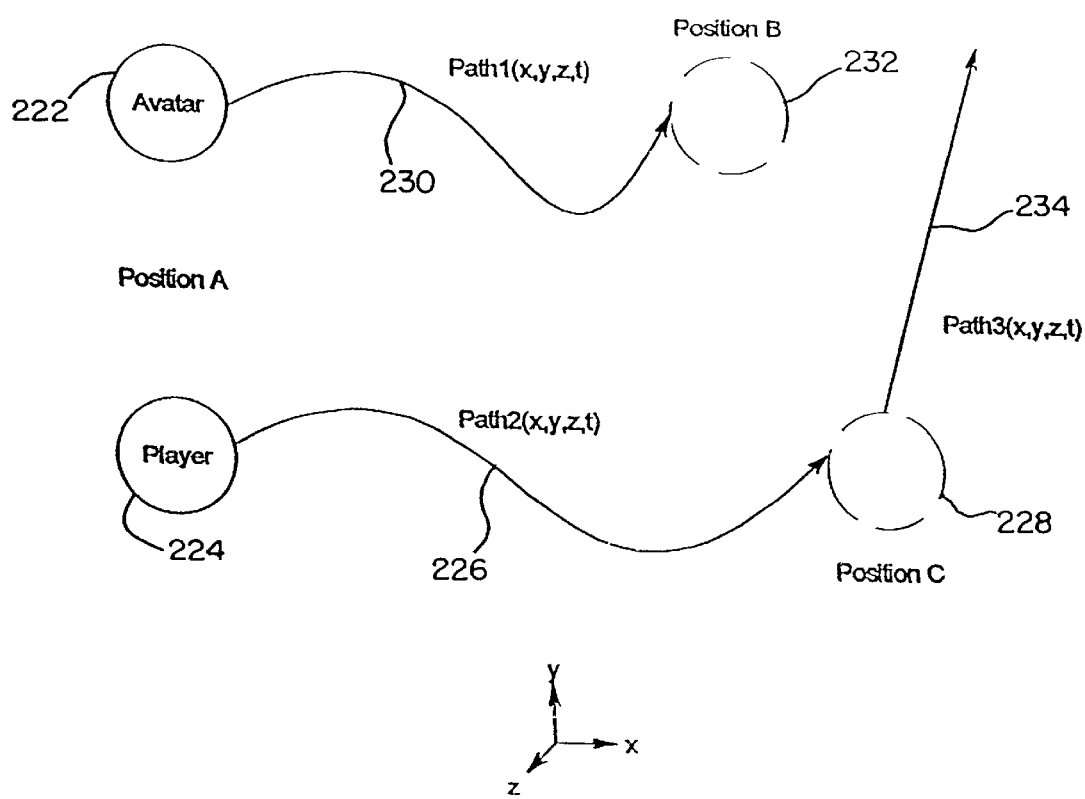
FIG. 11 is a schematic representation of a simulated task that the system executes to determine Opportunity.

Another measurement construct of the present invention is Opportunity—a quantification of the player's ability to create an asynchronous movement event when in an offensive role. The player's ability to execute abrupt changes (to cut) in his or her movement vector direction, expressed in the aforementioned absolute measures of performance, is one of the parameters indicative of the player's ability to create this asynchronous movement event. Referring to FIG. 11, Opportunity may be determined as follows:

a) A beacon, a component of the optical tracking system, is worn at the Player's waist.

b) At Position A, software scaling parameters make the virtual opponent 222, coordinates in the virtual environment equivalent to the player's 224 coordinates in the physical environment.

c) The Player moves along Path2(x,y,z,t) 226 to a physical Position C 228 The Player's objective is to maximize his/her movement skills in order to elude the virtual opponent 222.

d) In response, the system's video displays the virtual opponent's movement along Path1 (x,y,z,t) 230 to an equivalent virtual Position B 232. The virtual opponent's movement characteristics are programmable and modulated over time in response to the Player's performance.

e) The system calculates at each sampling interval the Player's new position velocity, acceleration, and power, and determines the moment the Player has created sufficient opportunity to abruptly redirect his/her movement along Path3(x,y,z,t) 234 to intersect the virtual opponent's x-y plane to elude and avoid collision with the virtual opponent.

f) The system provides real time numerical and graphical feedback of the calculations of part e.

A number of performance components are essential to successfully executing the two aforementioned global roles. Accordingly the system assesses the following performance constructs or components: Dynamic Reaction Time, Dynamic Phase Lag, First Step Quickness, and Dynamic Reactive Bounding, Dynamic Sports Posture, Functional Cardio-respiratory Status, Dynamic Reactive Cutting. These constructs are explained in detail below.

Dynamic Reaction Time is a novel measure of the player's ability to react correctly and quickly in response to cuing that prompts a sport specific response from the player. It is the elapsed time from the moment the virtual opponent attempts to improve its position (from the presentation of the first indicating stimuli) to the player's initial correct movement to restore a synchronous relationship (player's initial movement along the correct vector path).

Dynamic Reaction Time is a measurement of ability to respond to continually changing, unpredictable stimuli, i.e., the constant faking, staccato movements and strategizing that characterizes game play. The present invention uniquely measures this capability in contrast to systems providing only static cues which do not provide for continual movement tracking.

Dynamic Reaction Time is comprised of four distinct phases: the perception of a visual and/or audio cue, the interpretation of the visual and/or audio cue, appropriate neuromuscular activation, and musculoskeletal force production resulting in physical movement. It is important to note that Dynamic Reaction Time, which is specifically measured in this protocol, is a separate and distinct factor from rate and efficiency of actual movement which are dependent on muscular power, joint integrity, movement strategy and agility factors. Function related to these physiological components is tested in other protocols including Phase Lag and First Step Quickness.

Faced with the offensive player's attempt to create an asynchronous event, the defensive player must typically respond within fractions of a second to relevant dynamic cues if the defensive player is to establish or maintain the desired synchronous relationship. With such minimum response time, and low tolerance for error, the defensive player's initial response must typically be the correct one. The player must continually react to and repeatedly alter direction and/or velocity during a period of continuous movement. Any significant response lag or variance in relative velocity and/or movement direction between the player and virtual opponent places the player irrecoverably out of position.

Relevant testing must provide for the many different paths of movement by the defensive player that can satisfy a cue or stimulus. The stimulus may prompt movement side to side (the X translation), fore and aft (the Z translation) or up or down (the Y translation). In many instances, the appropriate response may simply involve a twist or torque of the player's body, which is a measure of the orientation, i.e, a yaw, pitch or roll.

Figure 12:
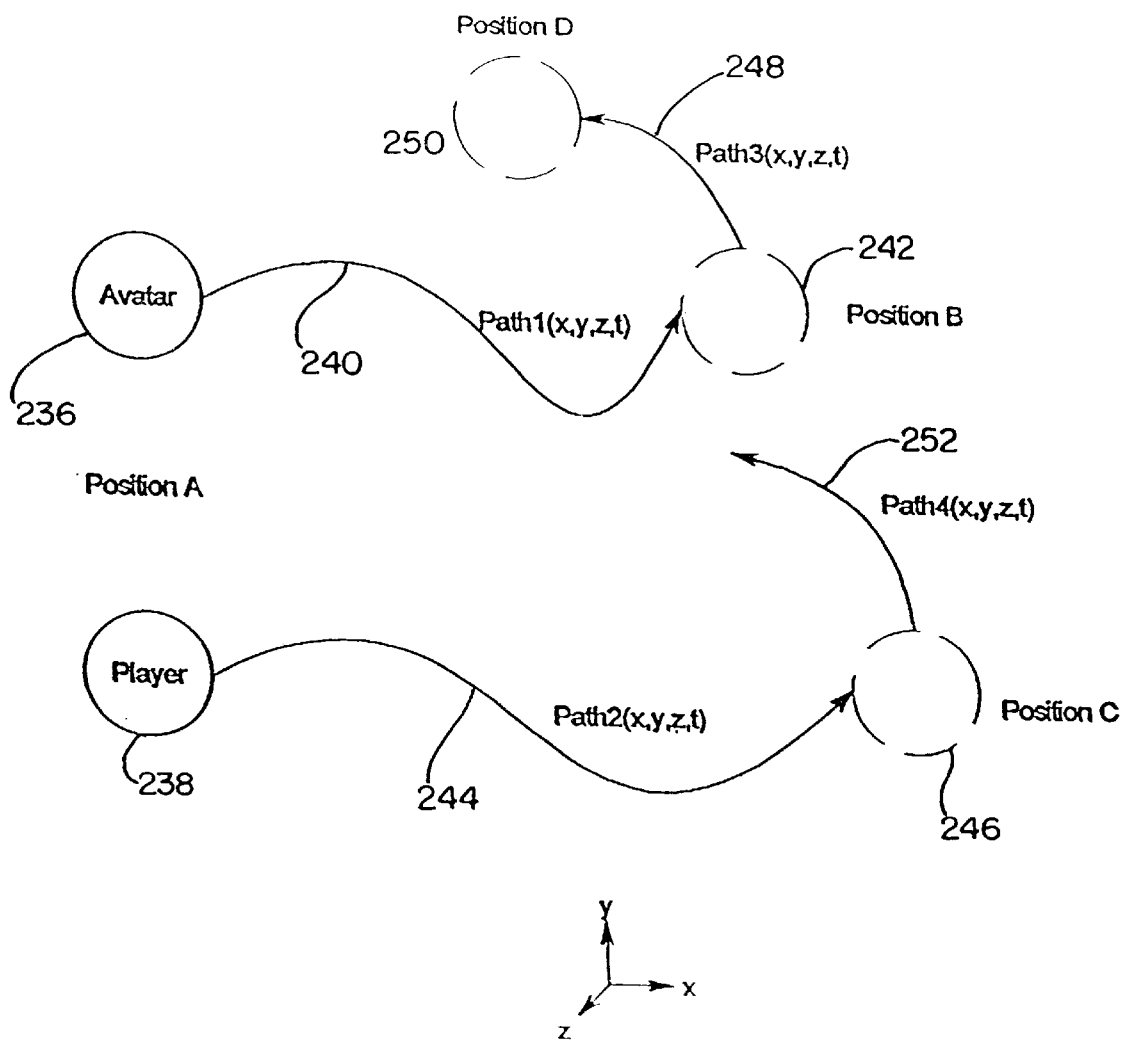
FIG. 12 is a schematic representation of a simulated task that the system executes to determine Dynamic Reaction Time.

Referring to FIG. 12, Dynamic Reaction Time may be determined as follows:

a) A beacon, a component of the optical tracking system, is worn at the Player's waist.

b) At Position A, software scaling parameters make the virtual opponent 236, coordinates in the virtual environment equivalent to the player's 238 coordinates in the physical environment.

c) The system's video displays the virtual opponent's movement along Path1(x,y,z,t) 240 to a virtual Position B 242.

d) In response, the Player moves along Path2(x,y,z,t) 244 to a near equivalent physical Position C 246. The Player's objective is to move efficiently along the same path in the physical environment from start to finish as does the virtual opponent in the virtual environment. However, since the virtual opponent typically moves along random paths and the Player is generally not as mobile as the virtual opponent, the player's movement path usually has some position error measured at every sample interval.

e) Once the virtual opponent reaches Position B 242, it immediately changes direction and follows Path3(x,y,z,t) 248 to a virtual Position D 250. The Dynamic Reaction Timer is started after the virtual opponent's x, y, or z velocity component of movement reaches zero at Position B 242 and its movement along Path3(x,y,z,t) 248 is initiated.

f) The Player perceives and responds to the virtual opponent's new movement path by moving along Path4(x,y,z,t) 252 with intentions to comply to virtual opponent's new movement path. The Dynamic Reaction Timer is stopped at the instant the Player's x, y, or z velocity component of movement reaches zero at Position C 246 and his/her movement is redirected along the correct Path4(x,y,z,t) 252.

g) The system calculates at each sampling interval the Player's new position velocity, acceleration, and power.

h) The system provides real time numerical and graphical feedback of the calculations of part g and the Dynamic Reaction Time.

Dynamic Phase Lag is defined as the elapsed time that the player is "out of phase" with the cuing that evokes a sport specific response from the player. It is the elapsed time from the end of Dynamic Reaction Time to actual restoration of a synchronous relationship by the player with the virtual opponent. In sports vernacular, it is the time required by the player to "recover" after being "out-of-position" while attempting to guard his opponent.

Figure 13:
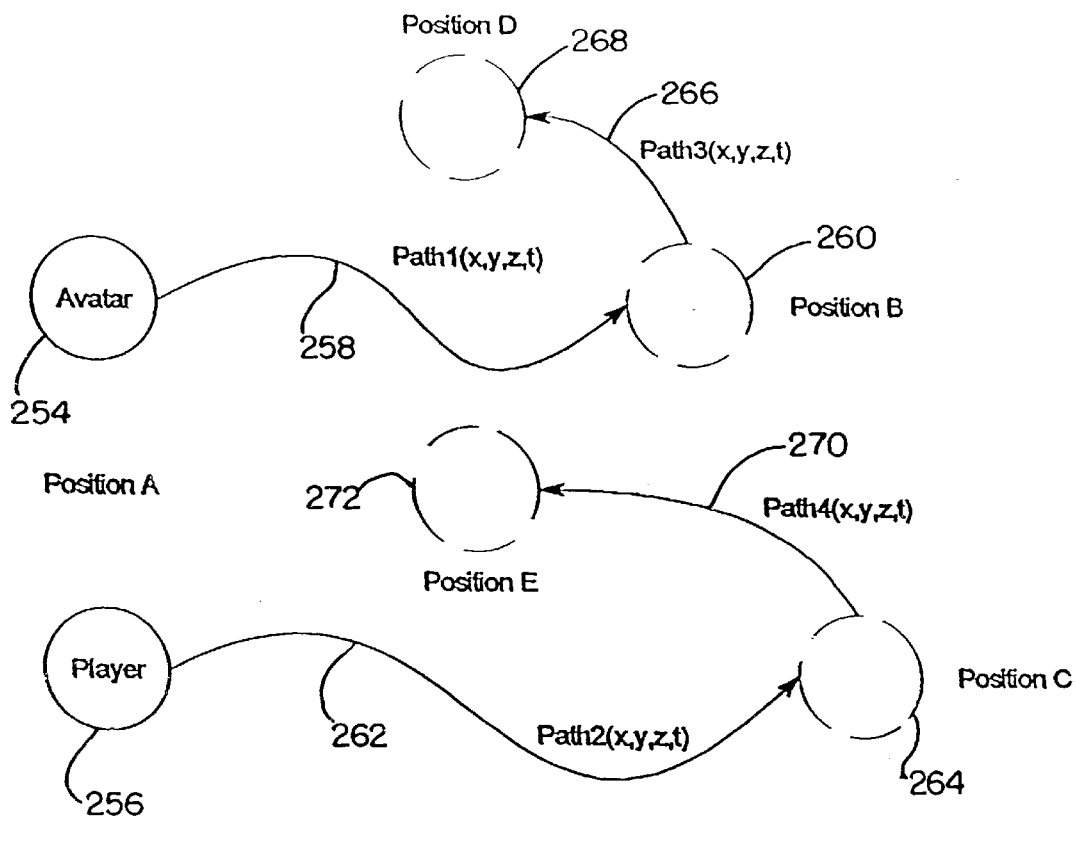
FIG. 13 is a schematic representation of a simulated task that the system executes to determine Dynamic Phase Lag.

Referring to FIG. 13, Dynamic Phase Lag may be determined as follows:

a) A beacon, a component of the optical tracking system, is worn at the Player's waist.

b) At Position A, software scaling parameters make the virtual opponent 254, coordinates in the virtual environment equivalent to the player's 256 coordinates in the physical environment.

c) The system's video displays the virtual opponent's movement along Path1(x,y,z,t) 258 to a virtual Position B 260.

d) In response, the Player moves along Path2(x,y,z,t) 262 to a near equivalent physical Position C 264. The Player's objective is to move efficiently along the same path in the physical environment from start to finish as does the Avatar in the virtual environment. However, since the virtual opponent typically moves along random paths and the Player is generally not as mobile as the virtual opponent 254, the player's movement path usually has some position error measured at every sample interval.

e) Once the virtual opponent reaches Position B 260, it immediately changes direction and follows Path3(x,y,z,t) 266 to a virtual Position D 268.

f) The Player perceives and responds to the virtual opponent's new movement path by moving along Path4(x,y,z,t) 270. The Phase Lag Timer is started at the instant the Player's x, y, or z velocity component of movement reaches zero at Position C 264 and his/her movement is directed along the correct Path4(x,y,z,t) 270 to position E 272.

g) When the Player's Position E finally coincides or passes within an acceptable percentage of error measured with respect to the virtual opponent's at Position D 268 the Phase Lag Timer is stopped.

h) The system calculates at each sampling interval the Player's new position velocity, acceleration, and power.

i) The system provides real time numerical and graphical feedback of the calculations of part h and the Phase Lag Time.

First Step Quickness may be measured as the player attempts to establish or restore a synchronous relationship with the offensive virtual opponent. First step quickness is equally important for creating an asynchronous movement event for an offensive player.

Acceleration is defined as the rate of increase of velocity over time and is a vector quantity In sports vernacular, an athlete with first step quickness has the ability to accelerate rapidly from rest, an athlete with speed has the ability to reach a high velocity over longer distances. One of the most valued attributes of a successful athlete in most sports is first step quickness.

This novel measurement construct purports that acceleration is a more sensitive measure of "quickness" over short, sport-specific movement distances than is average velocity or speed. This is especially true since a realistic simulation of sports challenges, which are highly variable in distance, would not be dependent upon fixed start and end positions. A second reason that the measurement of acceleration over sport-specific distances appears to be a more sensitive and reliable measure is that peak accelerations are reached over shorter distances, as little as one or two steps.

First step quickness can be applied to both static and dynamic situations. Static applications include quickness related to base stealing. Truly sports relevant quickness means that the athlete is able to rapidly change his movement pattern and accelerate in a new direction towards his goal. This type of quickness is embodied by Michael Jordan's skill in driving to the basket. After making a series of misleading movement cues, Jordan is able to make a rapid, powerful drive to the basket. The success of this drive lies in his first step quickness. Valid measures of this sports skill must incorporate the detection and quantifying of changes in movement based upon preceding movement. Because the vector distances are so abbreviated and the player is typically already under movement prior to "exploding", acceleration, power and/or peak velocity are assumed to be the most valid measures of such performance. Measures of speed or velocity over such distances may not be reliable, and at best, are far less sensitive indicators.

Numerous tools are available to measure the athlete's average velocity between two points, the most commonly employed tool being a stopwatch. By knowing the time required to travel the distance between a fixed start and end position, i.e., a known distance and direction, the athlete's average velocity can be accurately calculated. But just as an automobile's zero to sixty-mph time, a measure of acceleration, is more meaningful to many car aficionados than its top speed, an average velocity measure does not satisfy interest in quantifying the athlete's first step quickness. Any sport valid test of 1st step quickness must replicate the challenges the athlete will actually face in competition.

In situations where the athlete's movement is over short, sport-specific distances that are not fixed start and stop positions, the attempt to compare velocities in various vectors of unequal distance is subject to considerable error. For example, comparison of bilateral vector velocities achieved over different distances will be inherently unreliable in that the athlete, given a greater distance, will achieve higher velocities. Conventional testing means, i.e., without continual tracking of the player, can not determine peak velocities, only average velocities.

Only by continuous, high-speed tracking of the athlete's positional changes in three planes of movement can peak velocity, acceleration, and/or power be accurately measured. For accurate assessment of bilateral performance, the measurement of power, proportional to the product of velocity and acceleration, provides a practical means for normalizing performance data to compensate for unequal distances over varying directions since peak accelerations are achieved within a few steps, well within a sport-specific playing area First Step Quickness may be determined as follows.

Figure 14:
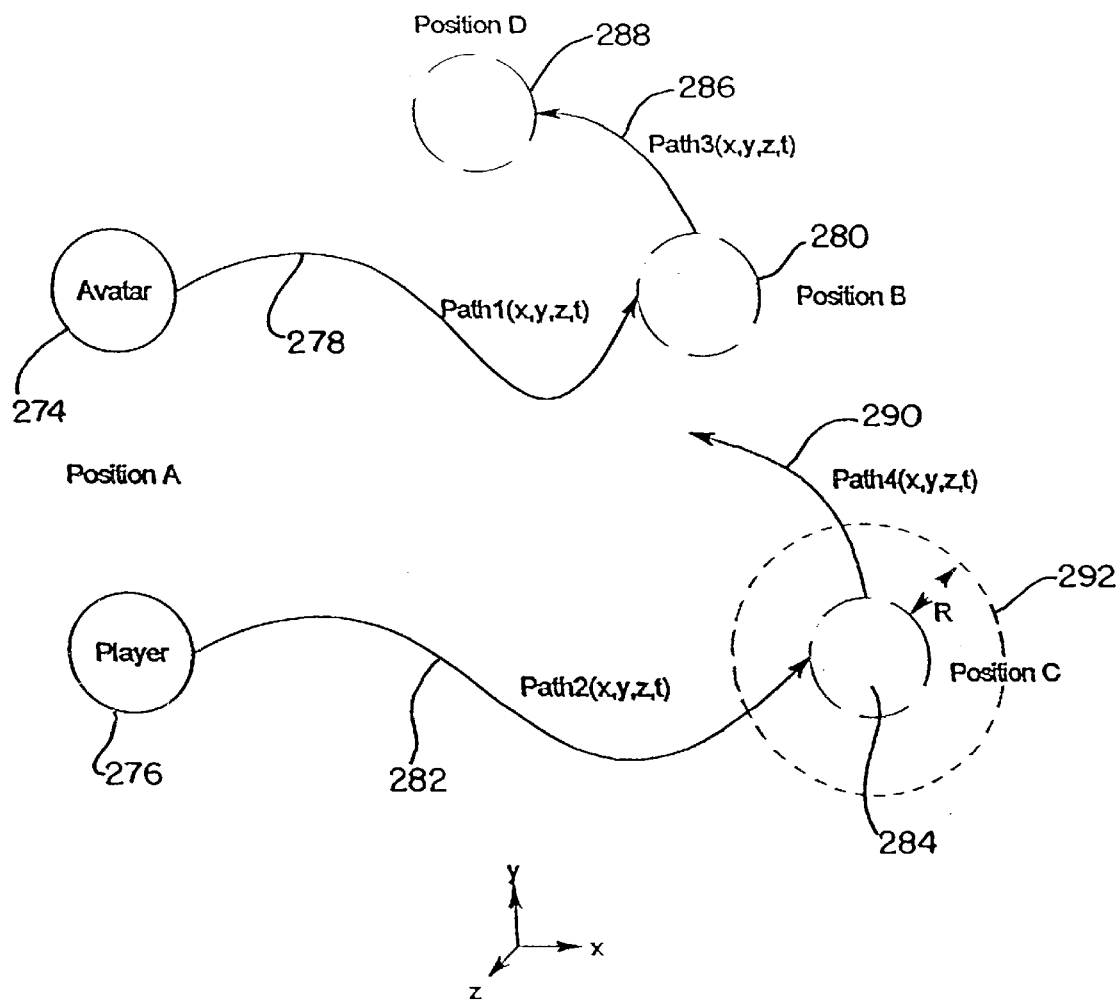
FIG. 14 is a schematic representation of a simulated task that the system executes to determine First Step Quickness.

Referring to FIG. 14,
a) A beacon, a component of the optical tracking system, is worn at the Player's waist.
b) At Position A, software scaling parameters make the virtual opponent 274 coordinates in the virtual environment equivalent to the player's 276 coordinates in the physical environment.
c) The system's video displays the virtual opponent's movement along Path1 (x,y,z,t) 278 to a virtual Position B 280.
d) In response, the Player moves along Path2(x,y,z,t) 282 to a near equivalent physical Position C 284. The Player's objective is to move efficiently along the same path in the physical environment from start to finish as does the virtual opponent in the virtual environment. However, since the virtual opponent typically moves along random paths and the Player is generally not as mobile as the virtual opponent, the player's movement path usually has some position error measured at every sample interval.
e) Once the virtual opponent reaches Position B 280, it immediately changes direction and follows Path3(x,y,z,t) 286 to a virtual Position D 288.
f) The Player perceives and responds to the virtual opponent's new movement path by moving along Path4(x,y,z,t) 290 with intentions to comply to virtual opponent's new movement path.

g) The system calculates at each sampling interval the Player's new position, velocity, acceleration, and power. Within a volume 292 having radius R, either the measurement of peak acceleration or the measurement of peak power, proportional to the product of peak velocity and acceleration, characterizes First Step Quickness.
h) The system provides real time numerical and graphical feedback of the calculations of part g.

Dynamic Reactive Bounding is the player's ability to jump or bound in response to cuing that evokes a sport specific response in the player. In certain protocols of the present invention, measured constructs include the player's dynamic reaction time in response to the virtual opponent's jumps as well as the player's actual jump height and/or bound distance and trajectory. Static measures of jumping (maximal vertical jump) have poor correlation to athletic performance. Dynamic measurements made within the present invention's simulation provide sports relevant information by incorporating the variable of time with respect to the jump or bound.

A jump is a vertical elevation of the body's center of gravity, specifically a displacement of the CM (Center of Mass) in the Y plane. A jump involves little, if any, horizontal displacement. In contrast, a bound is an elevation of the body's center of gravity having both horizontal and vertical components. The resulting vector will produce horizontal displacements in some vector direction.

Both the high jump and the long jump represent a bound in the sport of track and field. Satisfactory measures currently exist to accurately characterize an athlete's performance in these track and field events. But in these individual field events, the athlete is not governed by the unpredictable nature of game play.

Many competitive team sports require that the athlete elevate his or her center of gravity (Y plane), whether playing defense or offense, during actual game play. Examples include rebounding in basketball, a diving catch in football, a volleyball spike, etc. Unlike field events, the athlete must time her or his response to external cues or stimuli, and most frequently, during periods of pre-movement. In most game play, the athlete does not know exactly when or where he or she must jump or bound to successfully complete the task at hand.

It is universally recognized that jumping and bounding ability is essential to success in many sports, and that it is also a valid indicator of overall body power. Most sports training programs attempt to quantify jumping skills to both appraise and enhance athletic skills. A number of commercially available devices are capable of measuring an athlete's peak jump height. The distance achieved by a bound can be determined if the start and end points are known. But no device purports to measure or capture the peak height (amplitude) of a bounding exercise performed in sport relevant simulation. The peak amplitude can be a sensitive and valuable measure of bounding performance. As is the case with a football punt, where the height of the ball, i.e., the time in the air, is at least as important as the distance, the height of the bound is often as important as the distance.

The timing of a jump or bound is as critical to a successful spike in volleyball or rebound in basketball as its height. The jump or bound should be made and measured in response to an unpredictable dynamic cue to accurately simulate competitive play. The required movement vector may be known (volleyball spike) or unknown (soccer goalie, basketball rebound).

This novel measurement construct tracks in real time the actual trajectory of a jump or bound performed during simulations of offensive and defensive play. To measure the critical components of a jump or bound requires continuous sampling at high rates to track the athlete's movement for the purpose of detecting the peak amplitude as well as the distance achieved during a jumping or bounding event. Real time measurements of jumping skills include jump height, defined as the absolute vertical displacement of CM during execution of a vertical jump, and for a bound, the peak amplitude, distance and direction.

Figure 15:
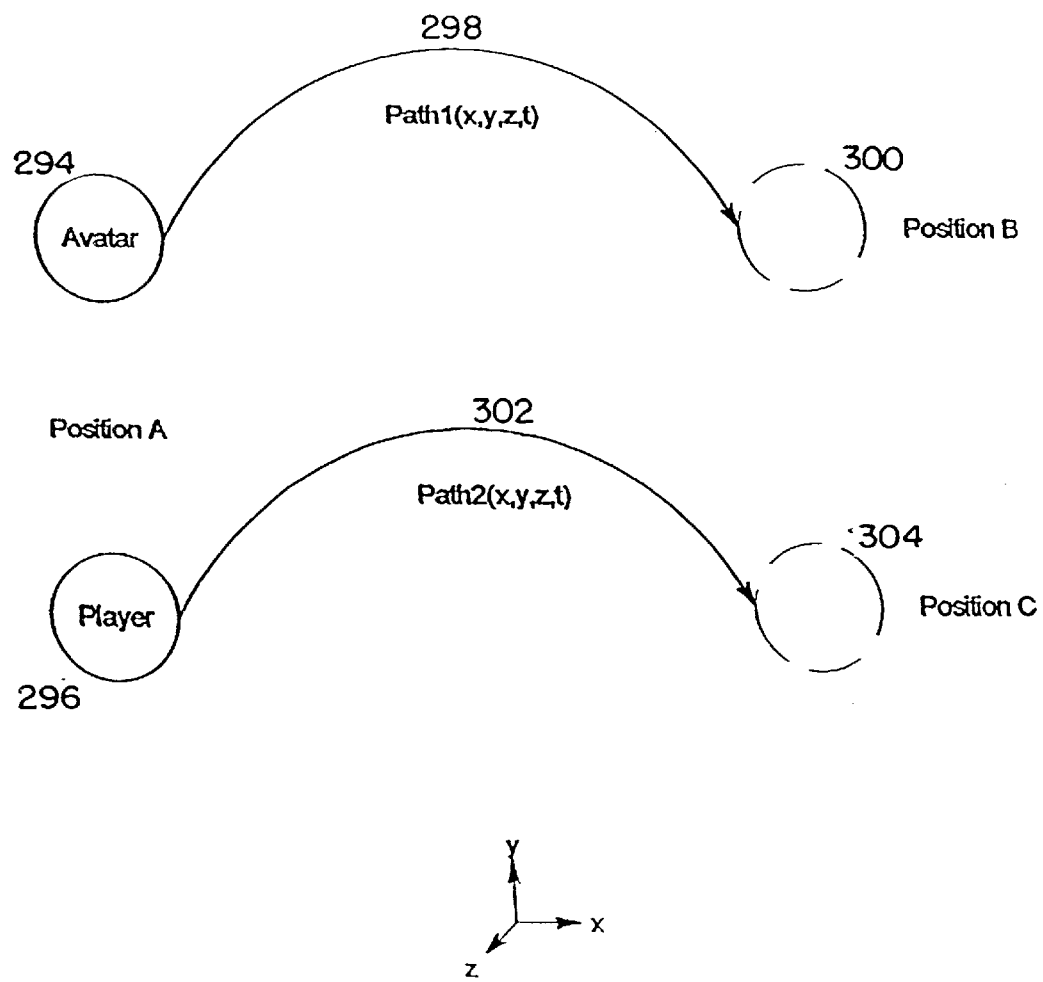
FIG. 15 is a schematic representation of a simulated task that the system executes to determine Dynamic Reactive Bounding.

Referring to FIG. 15, Dynamic Reactive Bounding may be determined as follows.

a) A beacon, a component of the optical tracking system, is worn at the Player's waist.

b) At Position A, software scaling parameters make the virtual opponent 294, or virtual opponent's coordinates in the virtual environment equivalent to the player's 296 coordinates in the physical environment.

c) The system's video displays the virtual opponent's movement along Path 1 (x,y,z,t) 298 to a virtual Position B 300. The virtual opponent's resultant vector path or bound is emphasized to elicit a similar move from the Player 296.

d) In response, the Player 296 moves along Path2(x,y,z,t) 302 to a near equivalent physical Position C 304. The Player's objective is to move efficiently along the same path in the physical environment from start to finish as does the virtual opponent in the virtual environment. However, since the virtual opponent typically moves along random paths and the Player is generally not as mobile as the virtual opponent, the player's movement path usually has some position error measured at every sample interval.

e) The system calculates at each sampling interval the Player's new position, velocity, acceleration, and power. In addition, components of the Player's bounding trajectory, i.e., such as air time, maximum y-displacement, are also calculated.

f) The system provides real time numerical and graphical feedback of the calculations of part e. The Player's bounding trajectory is highlighted and persists until the next bound is initiated.

Dynamic Sports Posture is a measure of the player's sports posture during performance of sport specific activities. Coaches, players, and trainers universally acknowledge the criticality of a player's body posture during sports activities. Whether in a defensive or offensive role, the player's body posture during sports specific movement directly impacts sport specific performance.

An effective body posture optimizes such performance capabilities as agility, stability and balance, as well as minimizes energy expenditure. An optimum posture during movement enhances control of the body center of gravity during periods of maximal acceleration, deceleration and directional changes. For example, a body posture during movement in which the center of gravity is "too high" may reduce stability as well as dampen explosive movements; conversely, a body posture during movement that is "too low" may reduce mobility. Without means of quantifying the effectiveness of a body posture on performance related parameters, discovering the optimum stance or body posture is a "hit or miss" process without objective, real time feedback.

Optimal posture during movement can be determined by continuous, high speed tracking of the player's CM in relationship to the ground during execution of representative sport-specific activities. For each player, at some vertical (Y plane) CM position, functional performance capabilities will be optimized. To determine that vertical CM position that generates the greatest sport-specific performance for each player requires means for continual tracking of small positional changes in the player's CM at high enough sampling rates to capture relevant CM displacements. It also requires a sports simulation that prompts the player to move as she or he would in actual competition, with abrupt changes of direction and maximal accelerations and decelerations over varying distance and directions.

Training optimum posture during movement requires that the player strive to maintain their CM within a prescribed range during execution of movements identical to those experienced in actual game play. During such training, the player is provided with immediate, objective feedback based on compliance with the targeted vertical CM. Recommended ranges for each player can be based either on previously established normative data, or could be determined by actual testing to determine that CM position producing the higher performance values.

Figure 16:
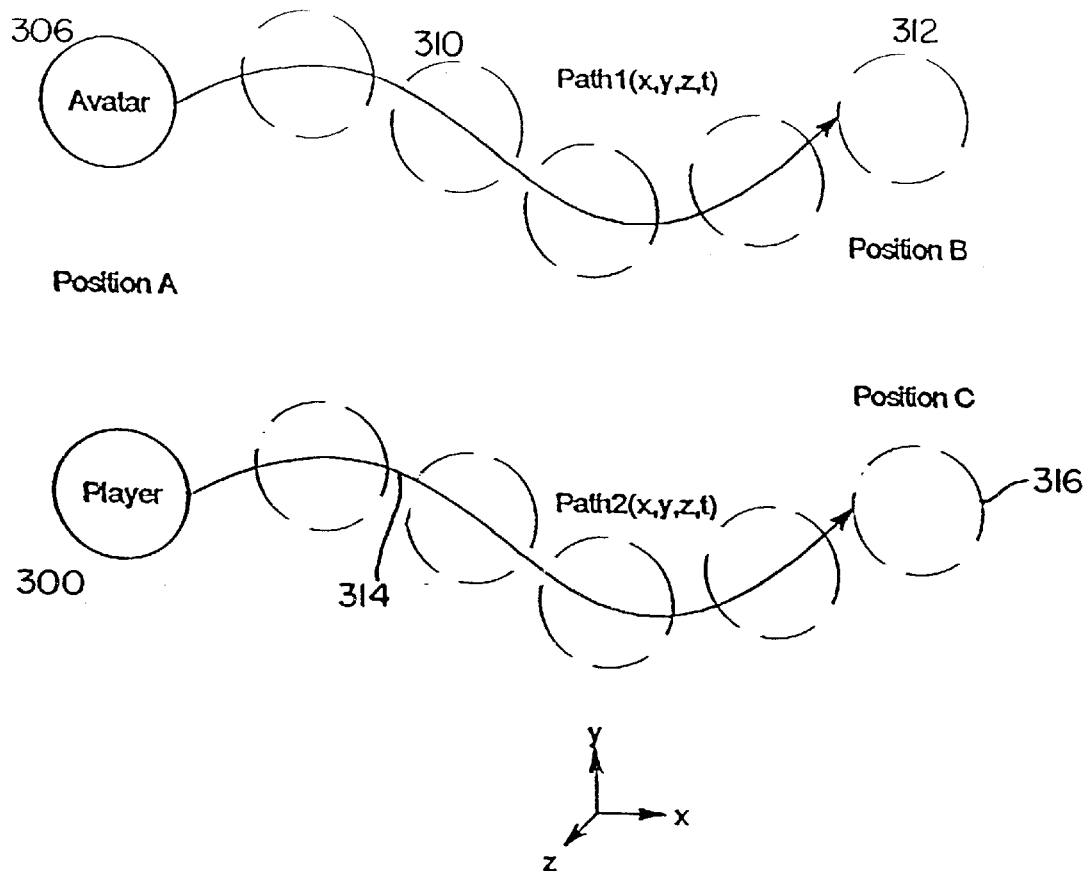
FIG. 16 is a schematic representation of a simulated task that the system executes to determine Dynamic Sports Posture.

Referring to FIG. 16, Dynamic Sports Posture during sport-specific activities may be determined as follows:

a) A beacon, a component of the optical tracking system, is worn at the Player's waist.

b) At Position A, software scaling parameters make the virtual opponent 306, coordinates in the virtual environment equivalent to the player's 308 coordinates in the physical environment.

c) The system's video displays the virtual opponent's movement along Path1(x,y,z,t) 310 to a virtual Position B 312.

d) In response, the Player moves along Path2(x,y,z,t) 314 to a near equivalent physical Position C 316. The Player's objective is to move efficiently and in synchronicity city to the virtual opponent's movement along the same path in the physical environment from start to finish as does the virtual opponent in the virtual environment. However, since the virtual opponent 306 typically moves along random paths and the Player 308 is generally not as mobile as the virtual opponent, the player's movement path usually has some position error measured at every sample interval.

e) The system calculates at each sampling interval the Player's most efficient dynamic posture defined as the CM elevation that produces the optimal sport specific performance.

f) The system provides real time numerical and graphical feedback of the calculations of part e.

Once the optimal Dynamic Posture is determined, training optimal Dynamic Posture may be achieved by the following steps:

a) A beacon, a component of the optical tracking system, is worn at the Player's waist.

b) The Player 308 assumes the dynamic posture that he/she wishes to train.

c) The system provides varying interactive movement challenges over sport specific distances and directions, including unplanned movements.

d) Y-plane positions, velocity, accelerations and power measurements that are greater or less than or equal to the pre-set threshold or window will generate real-time feedback of such violations for the Player 308.

e) The system provides real-time feedback of compliance with the desired dynamic posture during performance of the protocols.

Functional Cardio-respiratory Status (Fitness) is the player's cardio-respiratory status during the aforementioned sports specific activities. In most sports competitions, there are cycles of high physiologic demand, alternating with periods of lesser demand. Cardiac demand is also impacted upon by situational performance stress and attention demands. Performance of the cardiorespiratory system under sports relevant conditions is important to efficient movement.

Currently, for the purpose of evaluating the athlete's cardio-respiratory fitness for sports competition, stationary exercise bikes, treadmills and climbers are employed for assessing cardiac response to increasing levels of physical stress. Though such exercise devices can provide measures of physical work, they are incapable of replicating the actual stresses and conditions experienced by the competitive athlete in most sports. Accordingly, these tests are severely limited if attempts are made to correlate the resultant measures to actual sport-specific activities. It is well known that heart rate is influenced by variables such as emotional stress and the type of muscular contractions, which can differ radically in various sports activities. For example, heightened emotional stress, and a corresponding increase in cardiac output, is often associated with defensive play as the defensive player is constantly in a "coiled" position anticipating the offensive player's next response.

For the cardiac rehab specialist, coach, or athlete interested in accurate, objective physiological measures of sport-specific cardiovascular fitness, no valid tests have been identified. A valid test would deliver sport-specific exercise challenges to cycle the athlete's heart rate to replicate levels observed in actual competition. The athlete's movement decision-making and execution skills, reaction time, acceleration-deceleration capabilities, agility and other key functional performance variables would be challenged. Cardiac response, expressed as heart rate, would be continuously tracked as would key performance variables. Feedback of heart rate vs sport-specific performance at each moment in time will be computed and reported.

It will be appreciated that feedback regarding heart rate may be provided independent of feedback regarding sports-specific performance.

Functional Cardio-respiratory Fitness is a novel measurement construct capable of quantifying any net changes in sport-specific performance relative to the function of the cardio-respiratory system. Functional Cardio-respiratory Status may be determined as follows:

a) A beacon, a component of the optical tracking system, is worn at the Player's waist.
b) A wireless heart rate monitor 36A (FIG. 2) is worn by the Player. The monitor communicates in real-time with the system.
c) The system provides sport-specific exercise challenges to cycle the Player's heart rate to replicate levels observed in actual sport competition.
d) The system provides interactive, functional planned and unplanned movement challenges over varying distances and directions.
e) The system provides real-time feedback of compliance with a selected heart-rate zone during performance of defined protocols.
f) The system provides a real-time numerical and graphical summary of the relationship or correlation between heart rate at each sample of time and free-body physical activity.

Dynamic Reactive Cutting is a measure of the player's ability to execute an abrupt change in position, i.e., a "cut" can be a directional change of a few degrees to greater than 90 degrees. Vector changes can entail complete reversals of direction, similar to the abrupt forward and backward movement transitions that may occur in soccer, hockey, basketball, and football. The athlete running at maximum velocity must reduce her or his momentum before attempting an aggressive directional change, this preparatory deceleration often occurs over several gait cycles. Once the directional change is accomplished, the athlete will maximally accelerate along his or her new vector direction.

Accurate measurement of cutting requires continuous tracking of position changes in three planes of movement; ascertaining the angle scribed by the cutting action; and measuring both the deceleration during braking prior to direction change and the acceleration after completing the directional change.

For valid testing, the cues (stimuli) prompting the cutting action must be unpredictable and interactive so that the cut can not be pre-planned by the athlete, except under specific training conditions, i.e., practicing pass routes in football. It must be sport specific, replicating the types of stimuli the athlete will actually experience in competition. The validity of agility tests employing ground positioned cones and a stopwatch, absent sport-relevant cuing, is suspect. With knowledge of acceleration and the player's body weight, the power produced by the player during directional changes can also be quantified.

Figure 17:
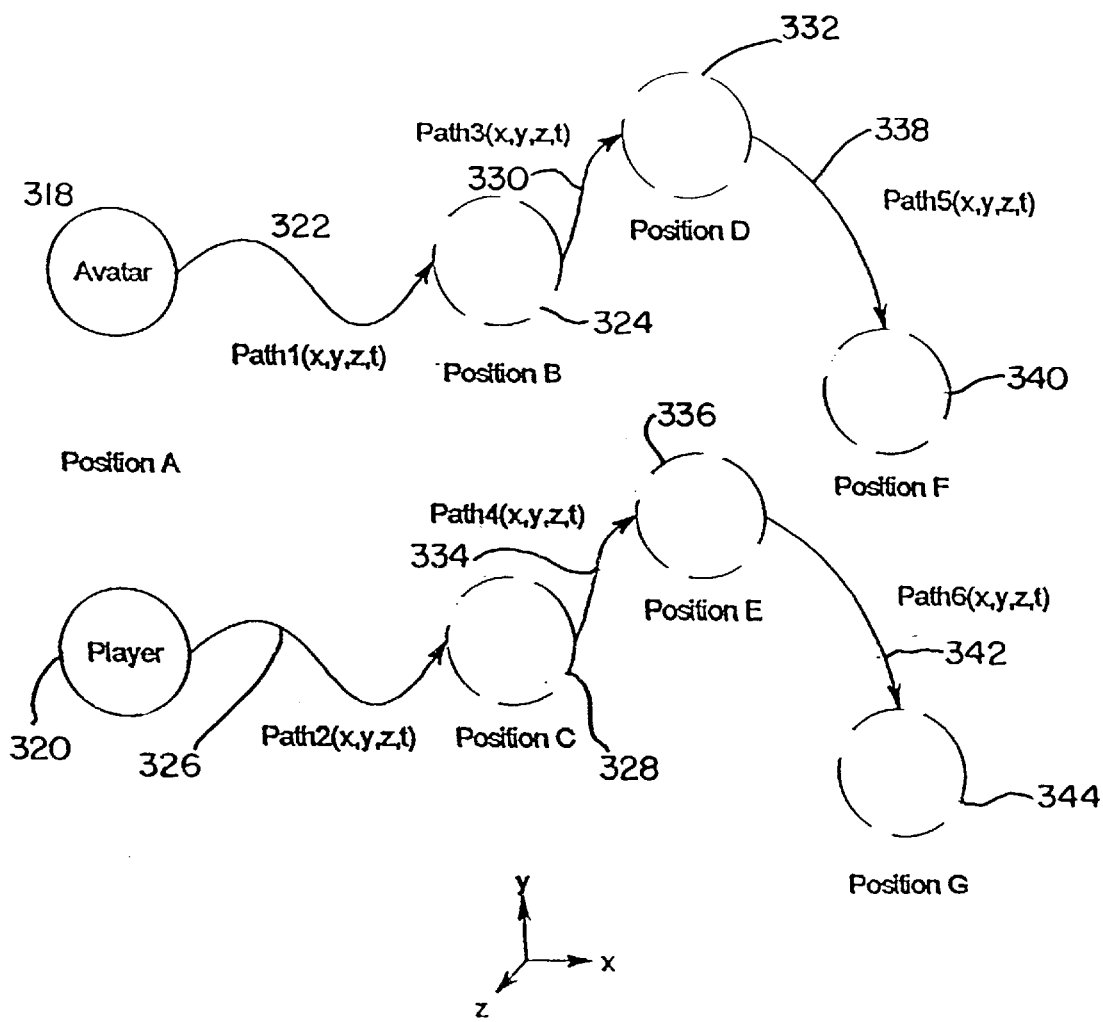
FIG. 17 is a schematic representation of a simulated task that the system executes to determine Dynamic Reactive Cuffing.

Referring to FIG. 17, Vector Changes and Dynamic Reactive Cutting may be determined as follows:

a) A beacon, a component of the optical tracking system, is worn at the Player's waist.
b) At Position A, software scaling parameters make the virtual opponent 318, or virtual opponent's coordinates in virtual environment equivalent to the player's 320 coordinates in the physical environment.
c) The system's video displays the virtual opponent's movement along Path1(x,y,z,t) 322 to a virtual Position B 324.
d) In response, the Player 320 moves along Path2(x,y,z,t) 326 to a near equivalent physical Position C 328. The Player's objective is to move efficiently along the same path in the physical environment from start to finish as does the virtual opponent 318 in the virtual environment. However, since the virtual opponent typically moves along random paths and the Player is generally not as mobile as the virtual opponent, the player's movement path usually has some position error measured at every sample interval.
e) Once the virtual opponent 318 reaches Position B 324, it immediately changes direction and follows Path3(x,y,z,t) 330 to a virtual Position D 332.
f) The Player perceives and responds to the virtual opponent's new movement path by moving along Path4(x,y,z,t) 334 to physical Position E 336.
g) Once the virtual opponent 318 reaches virtual Position D 332, it immediately changes direction and follows Path5(x,y,z,t) 338 to virtual Position F 340.
h) The Player perceives and responds to the virtual opponent's new movement path by moving along Path6(x,y,z,t) 342 to physical Position G 344.
i) Subsequent virtual opponent 318 movement segments are generated until sufficient repetition equivalency is established for all vector movement categories represented during the performance of sport-specific protocols, including unplanned movements over various distances and direction.

j) The system calculates at each sampling interval the Player's new position and/or velocity and/or acceleration and/or power and dynamic reactive cutting.

k) The system provides real time numerical and graphical feedback of the calculations of part j.

It should be noted that these motor-related components of sports performance and fitness (which may be or may be derived from movement parameter(s)) are equally important to safety, success and/or productivity in demanding work environments, leisure sports, and many activities of daily living.

The performance-related components are often characterized as either the sport-specific, functional, skill or motor-related components of physical fitness. These performance-related components are obviously important for safety and success in both competitive athletics and vigorous leisure sports activities. It should be equally obvious that they are also essential for safety and productive efficiency in demanding physical work activities and unavoidably hazardous work environments such as police, fire and military—as well as for maintaining independence for an aging population through enhanced mobility and movement skills.

First Person Perspective

Another embodiment of the invention involves a personal perspective, also known as a first person perspective This perspective is a view on the display of the virtual space from the perspective of the player. It is in contrast to the type of information shown on the display 28 in FIGS. 2–4, which is generally termed a third person perspective. In a third person perspective the view of the virtual space is from some viewpoint outside of the playing field, akin to the view a spectator would have. The viewpoint is generally fixed, although the viewpoint may move as action in the virtual space shifts to different parts of the virtual space. For example, the third person perspective in a basketball simulation may shift between two half-court views, depending on where the ball and the players are in virtual space.

In a third person perspective the movement of the icons in virtual space is represented by the movement of icons within the generally fixed view. Thus movement of a player icon to a different location in virtual space results in movement of a corresponding player icon within the view from the generally fixed viewpoint.

Figure 18:
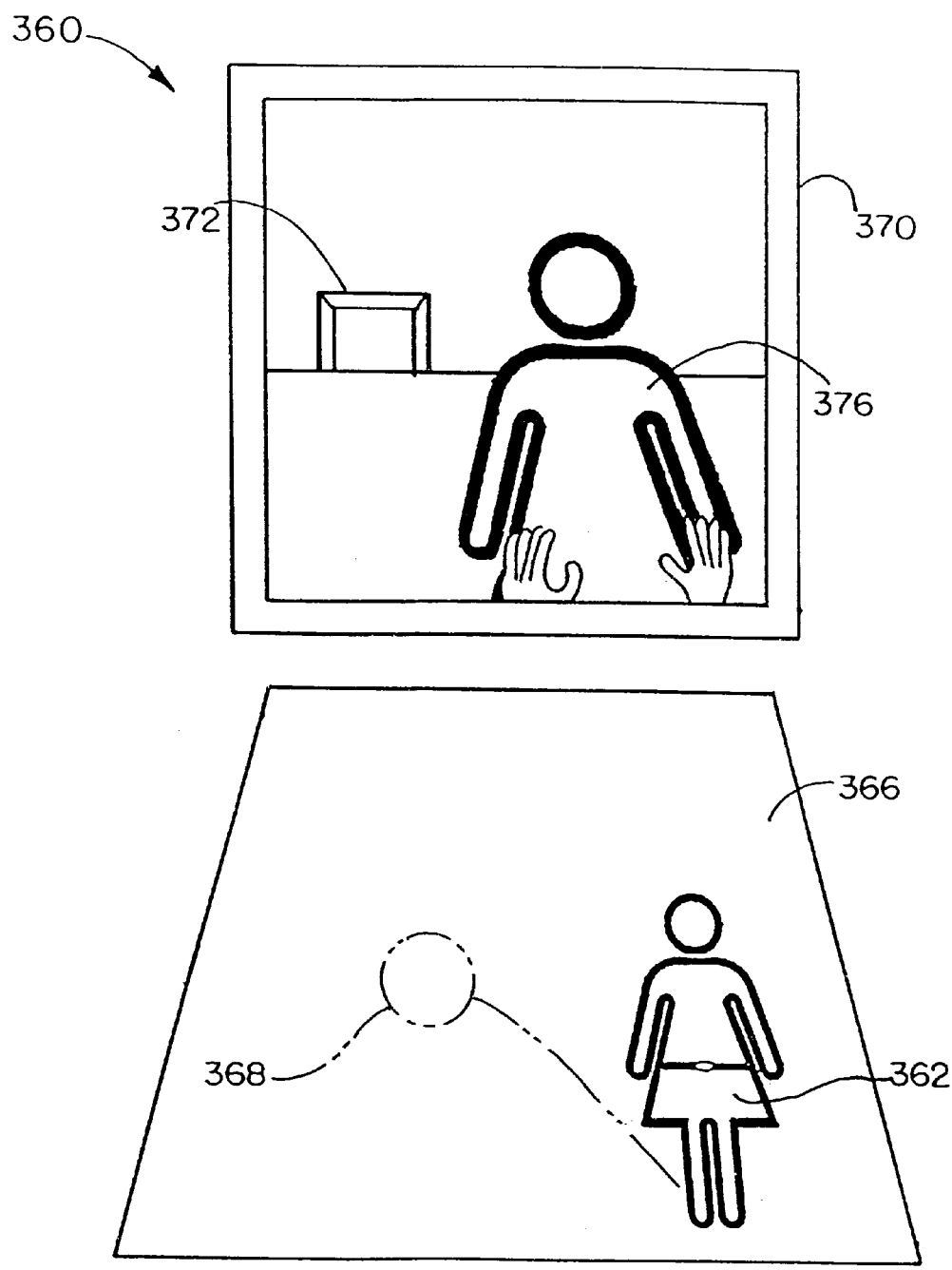
FIG. 18 is a perspective view of an alternate embodiment of the invention which uses a first person perspective view.

However, a first person view is a view from a perspective within the simulation. A system 360 including first person viewing is shown in FIG. 18. Such a perspective is generally that of a participant in the simulation, such as a player 362. The player 362 moves within a physical space 366, such movement being detected by a tracking system as described above. As the player 362 moves to a new location 368, for example, the view on a display 370 is altered to show virtual space from the viewpoint in virtual space corresponding to the new location 368. Thus the viewpoint will correspond to that of a virtual being (corresponding to the player) at a location in virtual space corresponding to the player's location in physical space.

A stationary object 372 in the virtual space will change its position on the display to reflect its position relative to the new viewpoint. A movable object in virtual space such as a protagonist 376 also changes its position on the display 370 in response to a shift in viewpoint caused by movement of the player 362. In addition, the protagonist 376 also is able to change its position within the virtual space. A change in position by the protagonist will also result in a change of its position on the display 370.

The system 360 may also display a representation indicating part of the virtual being corresponding to the player 362, for example the hands 378 shown on the display 370 in FIG. 18. Such display elements may be used, for example, to indicate items held by the virtual being in the virtual space, to indicate position of part of the player's body (e.g., whether the hands are raised), or to indicate orientation of the player. The representation may resemble part of a human body, e.g., hands, feet, etc. Alternatively the representation may be of other objects, e.g., wings, abstract shapes, etc. The representation may or may not be always in the displayed view.

The display of a first person perspective increases the fidelity of the simulation, by making the view on the display closer to that which would be perceived by the player in a real life activity.

Multiple Player Encounters

It will be appreciated that it is possible to have simulations or games using the above systems where multiple players participate at once. Such multiple players may merely be displayed together, not interacting, or may alternatively interact by competing against one another or by cooperating in a task or tasks.

Figure 19:
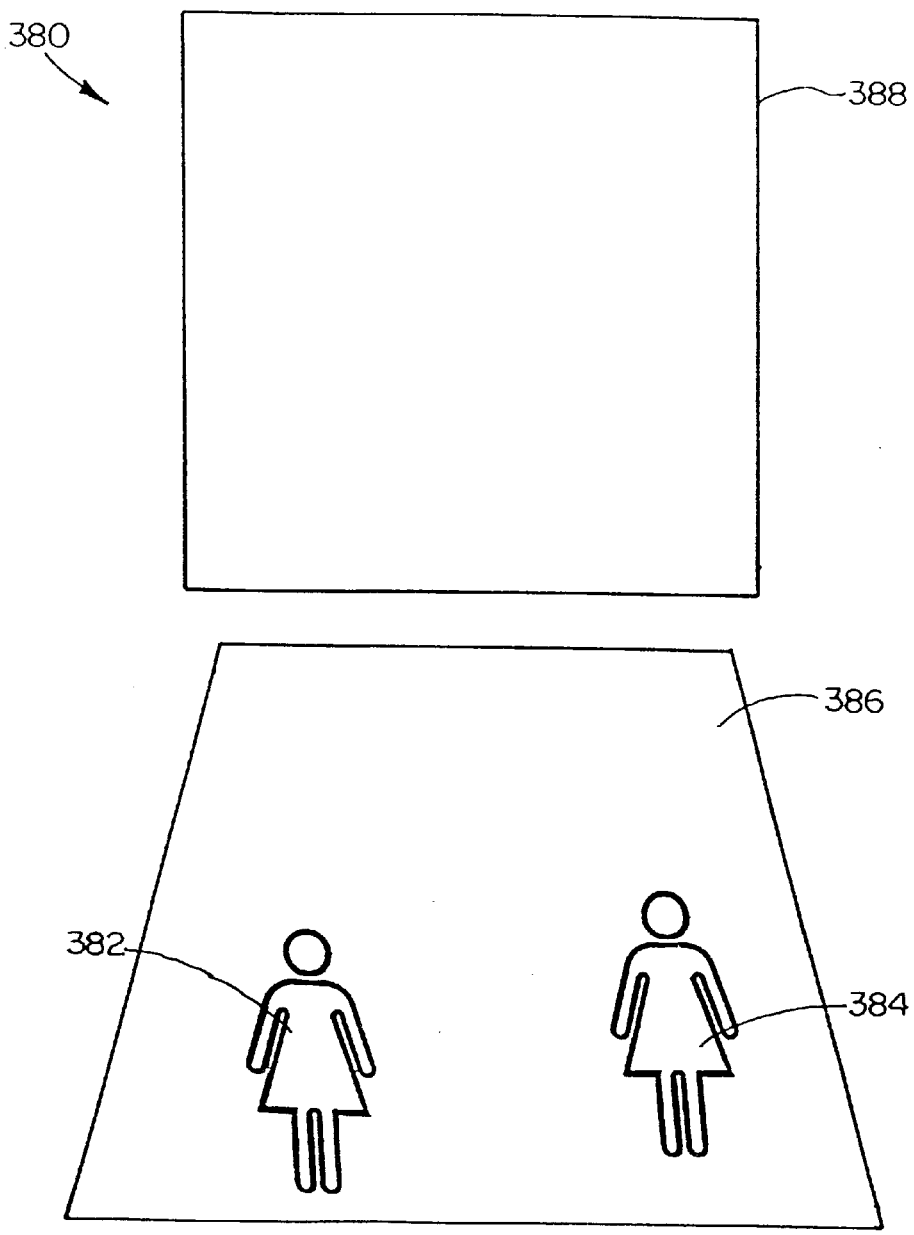
FIG. 19 is a perspective view of the invention being used for multiplayer play.

As shown in FIG. 19, a system 380 has multiple players 382 and 384 which participate using the same physical space 386 and display 388. Displayed player icons 390 and 392 correspond to the positions of the players 382 and 384. It will be appreciated that it is desirable for the tracking system associated with the system 380 to be able to differentiate between the players 382 and 384.

Figure 20:
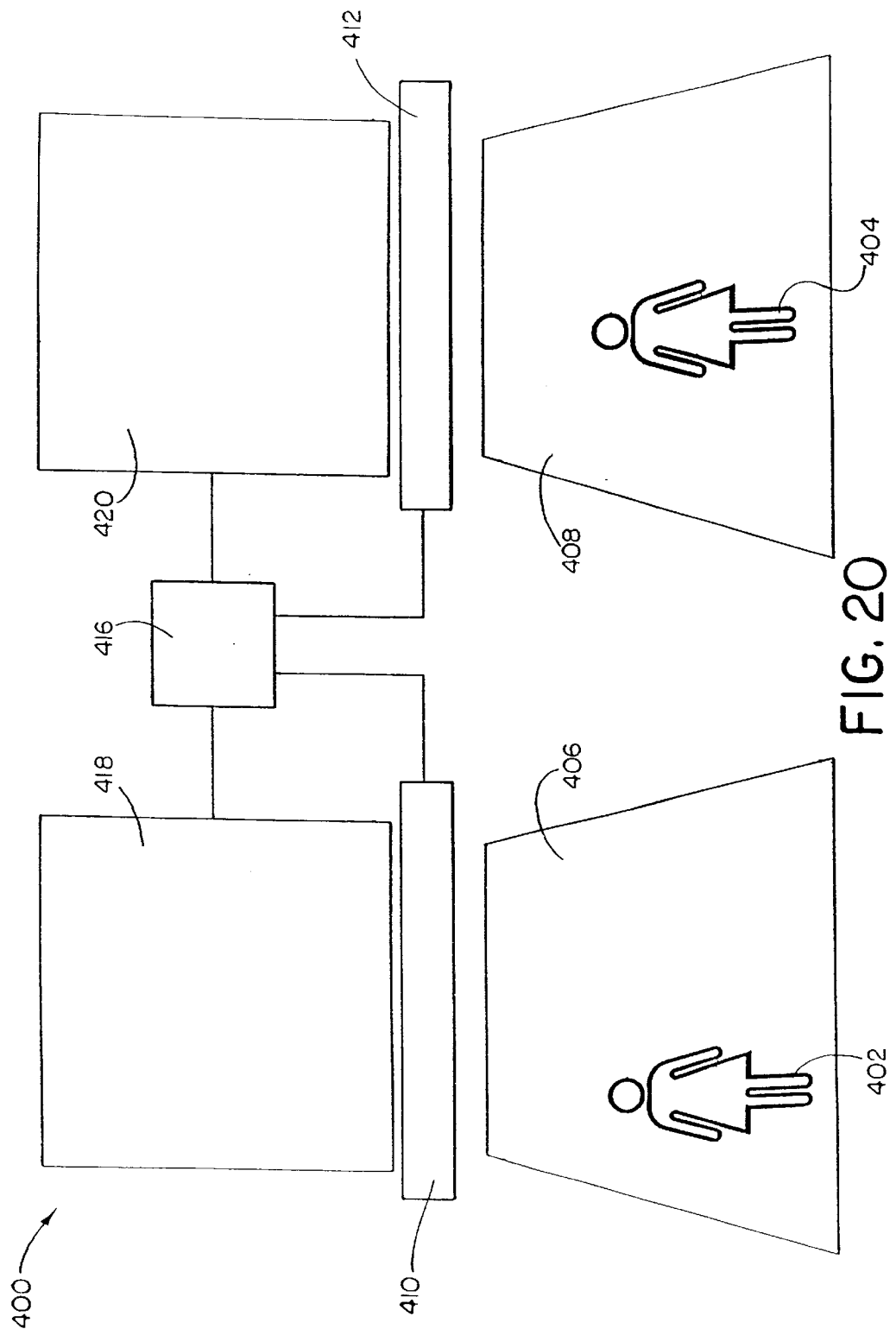
FIG. 20 is a perspective view of an alternate embodiment of the invention that uses multiple physical spaces and displays.

It will be appreciated that a system where the players share the same physical space presents the potential of the players colliding, possibly leading to injury. Accordingly, FIG. 20 shows an alternate embodiment, a system 400 in which multiple players 402 and 404 participate simultaneously in separate respective physical spaces 406 and 408.

The physical spaces 406 and 408 may be located in the same room, in which case it may be possible to have one tracking system track the position of both of the players. However, it may be more effective to have separate tracking systems for each of the physical spaces. This is shown in the illustrated embodiment, with tracking systems 410 and 412 corresponding to respective physical spaces 406 and 408.

It will be appreciated that separate tracking systems will generally be needed if the physical spaces 406 and 408 are in different locations, such as in different rooms or in different buildings.

The tracking systems 410 and 412 are operatively coupled to a computer 416 (which consist of two separate computer units in communication with one another and/or with a central computer unit). The computer 416 in turn is operatively coupled to displays 418 and 420 which correspond to the physical spaces 406 and 408, respectively. The operative coupling between the computer 416, and the tracking systems 410 and 412 and the displays 418 and 420 may be accomplished by means of hard-wired cables between these components. Alternatively, it will be appreciated that the operative coupling may employ other means such as modems and telephone lines, radio or infrared light signals, or connections to computer networks such as the World Wide Web. Thus such connections may be made over long distances, allowing players separated by a large physical distance to participate in a simulation in the same virtual space. It will be appreciated that more than one computer or processor may be used, especially with systems connected over large distances.

The displays 418 and 420 may show the same view of virtual space, such as a the same third person perspective. Alternatively and preferably, the displays 418 and 420 may show different views of the virtual space. For example, for a simulated tennis match each of the displays may show a third person perspective view from the end of the court corresponding to the respective physical spaces. Alternatively, different first person perspective views of the physical space may be shown on each of the displays. Thus each display may have a viewpoint in virtual space corresponding to the location of the player viewing that display.

It will be appreciated that more than two players may be involved in the same simulation, with additional physical spaces, displays, tracking systems, and/or computers added as appropriate. For example, each player may have an individual game unit (a display, tracking system, and physical space), while all the players share a computer or computers. It will be appreciated that even when more than one physical space is used, more than one player may occupy each physical space. For example, a simulated tennis doubles match may involve two physical spaces, with two players occupying each physical space.

It will be appreciated that the multiplayer simulation disclosed above allows the performance of more than one person to be evaluated simultaneously. In addition, the use of a live player as a virtual opponent results in a more realistic sports simulation. Despite advances in technology and artificial intelligence, computers are unable to capture the nuances of human thinking and behavior in general, and sports strategy in particular. Much of sports performance is governed by compressed time frames—mere milliseconds—within which offensive and defensive opponents are capable of a wide variety of movements associated with six degrees of freedom. Computers are as of yet unable to fully simulate this behavior.

Performance Scaling

Figure 21:
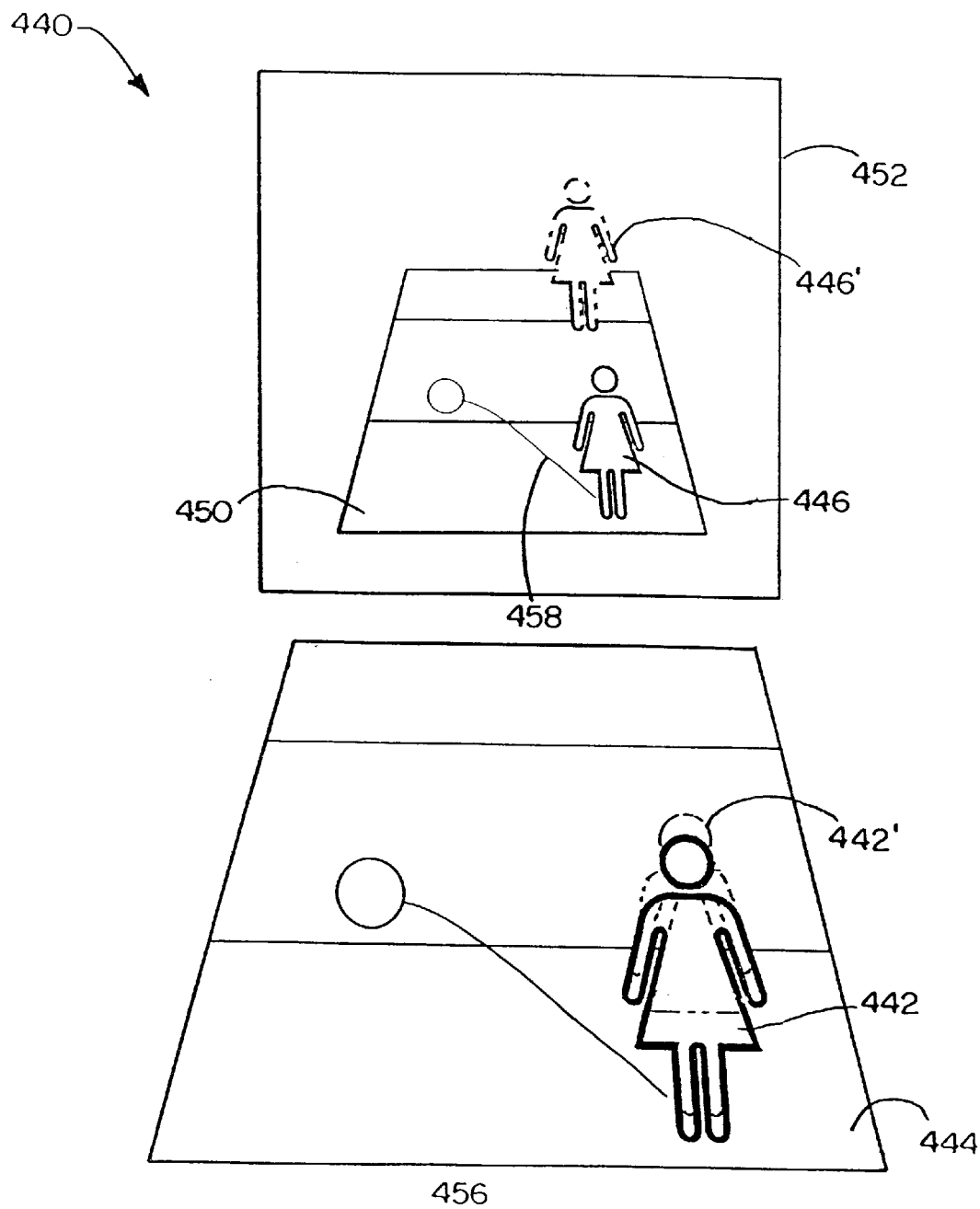
FIG. 21 is a perspective view of an alternate embodiment of the present invention which uses scaling factors.

FIG. 21 illustrates an alternate embodiment of the invention which includes performance scaling, also known as handicapping. There is shown in FIG. 21 a testing and training system 440 with performance scaling. One or more scaling factors define the relationship between movements of a player 442 in a physical space 444 and changes in the virtual space position corresponding to the player 442 (represented in FIG. 21 as the position of player icon 446 in a representation of virtual space 450 shown on a display 452).

If the player 442 makes a small jump, such as to position 442', this could be represented in virtual space and displayed as a much larger jump to position 446'. A scale factor could be used to control the relationship between the actual jump height and the apparent jump height in virtual space. Such scaling may be linear or nonlinear.

Similarly, movement by the player 442 along a path 456 may be displayed through use of a scale factor as movement of a greater or lesser distance, such as movement along a virtual path 458.

The scale factors may be different for movement in different directions. In addition, the scale factors may be adjusted to take into account differences in skill levels and training levels of different players and different avatars or protagonists. Thus through use of scale factors a child may be enabled to compete evenly in a virtual basketball game against a protagonist having the ability of Michael Jordan, for example.

Scaling may also be used to provide positive feedback which encourages further efforts. For example, a person undergoing rehabilitation after an injury is likely to react positively to a large apparent result in virtual space to a physical effort that produces only a small movement. Such a person may thereby be encouraged to continue exercising and improving skills when he or she might otherwise become discouraged.

Scaling may be adjusted during an individual protocol, or during a series of protocols making up a training session. Such adjustments may be made in response to increased performance, for example due to acquisition of new skills, or decreased performance, for example due to fatigue or injury.

It will be appreciated that scaling may be integrated with the multiplayer systems described above so as to handicap one of the opponents relative to the other. This handicapping may be used to make competitive an encounter between two opponents of unequal skill, such as a parent and a child, or a fan and a trained athlete. Through scaling a wily, though physically less adept, person, such as a coach, may more directly interact for teaching purposes with a more physically able student.

It will be appreciated that there are many other permutations of the above-described handicapping and scaling concepts. For example, a multiplayer tennis match may be handicapped by providing one of the players with a higher net (which would be perceived only in that player's display). A scaled lag may be added to slow down the apparent quickness of one of the players. One player may have a maximum top speed for changes of position in the virtual space.

Progression Algorithm

Using the above-described systems, protocols may be created that are designed to lead a player or subject through a series of motions. For example, a protocol may be used to drill a subject on a skill, such as lateral motion or timed leaping ability. Groups of protocols may be created that involve skills specific to a certain sport, the groups being selectable for playback as such by a user. For example, drills involving basketball skills or drills involving baseball skills may be grouped, allowing an athlete with a particular interest or in training for a specific sport to easily locate and playback drills for developing appropriate skills.

The invention allows modulation, over a continual range, of playback of stored protocols. This modulation may be accomplished by the speed, amplitude, and/or direction of motion by an avatar or protagonist during playback of a protocol. Such modulation may be used to tailor an exercise program to the abilities of an individual user. For example, a rehabilitating geriatric may be sufficiently challenged by playback of a given protocol at 20% of the speed it was recorded at. However, an elite healthy athlete may require playback of the same protocol at 140% of the speed it was recorded at. User-specific modulation levels may be recorded for analysis of results and for recall for future training sessions of that user. As a user progresses the modulation of protocols may be changed to continue to provide the user with new challenges.

Playback of protocols may also be modulated during an individual protocol or series of protocols in response to user performance. For example, comparison of current performance to past performance may indicate that the user is ready to begin training at a new, higher level of performance—modulation of playback of protocols may be revised accordingly to provide a new challenge within that training session. Alternatively, modulation may be revised in response to decreased performance, for example due to fatigue or injury.

Modulation of the playback of stored protocols allows a single protocol to be used by subjects having different skill levels. Thus results for various training sessions of one user, and the results of various users of different skill levels, may readily be compared.

Recordation of Protocols

Figure 22:
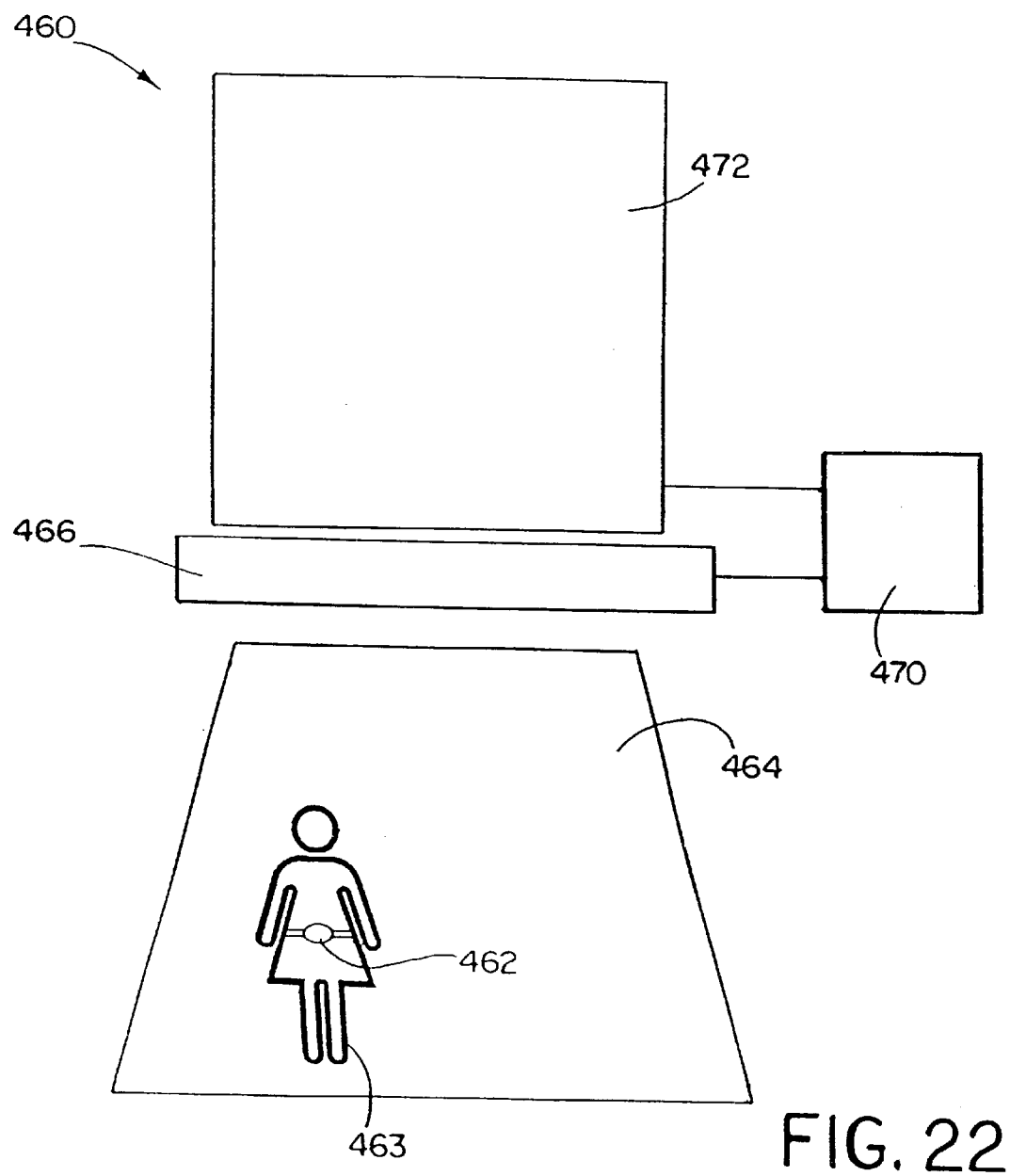
FIG. 22 is a perspective view of an alternate embodiment of the present invention which can record movement protocols.

Further in accordance with the invention, a system 460 which is able to record protocols for later playback, is shown in FIG. 22. In the system 460 a trainer or protocol creator 462 wearing a beacon or reflector 463 moves within a physical space 464, thereby creating a three dimensional contour pattern. The motion of the trainer 462 is tracked by a tracking system 466 as described above. The positional data output from the tacking system 466 is sent to a computer 470. The computer 470 includes a storage device such as a floppy disk drive, a hard disk drive, a writeable optical drive, a tape drive, or the like. Alternatively, the storage device may be separate from the computer.

The storage device records the movement contours of the trainer 462 for later playback. The position of the trainer 462 may also be represented on a display 472 by the location of an icon in a virtual space, thus providing feedback to the trainer regarding his or her movements. Such recordation is preferably at a rate of at least 20 Hz, is more preferably at a rate of at least 50 Hz, and is even more preferably at a rate of 70 Hz.

The protocol so recorded by the system 460 may be played back, with the motion of an avatar following the recorded motion contour of the trainer 462. The avatar following this recorded motion contour may be interacted with by a player or subject. For example, the player may be trained to emulate the trainer's movements by attempting to maintain synchronicity with the avatar's movements. A measure of compliance may be made between the player's motions and the prerecorded motions of the trainer.

Thus the system 480 may be used as follows:
a) The protocol creator 462 dons the beacon 463 and "choreographs" a desired movement pattern while his or her positional changes over time are recorded. This recording represents the creator's movement contour pattern.
b) A user attempts to follow (the synchronicity measurement construct), or somehow interacts with, the prerecorded movement contour pattern at a selected playback rate.
c) The user is provided with real time feedback as to his or her compliance.

It will be appreciated that the recording feature of the system 480 may be used to record motions of a subject for later playback, for review and/or evaluation by the subject or by others.

Measurement of Orientation

As indicated above, beacons may be used to measure orientation of body of the player or subject. Measurement of orientation is useful in situations where an appropriate response to a stimulus may simply involve a twist or torque of the player's body. The ability to measure orientation is valuable in a number of respects.

Orientation may used to increase fidelity of simulation. Display of an icon representing the player or subject may be altered depending upon the orientation of the player. In multiplayer simulations, representation of orientation imparts useful information to an opponent, since many maneuvers such as fakes and feints often mostly or totally involve changes in orientation as opposed to changes in position.

For first person perspectives, taking orientation into account allows the view a player sees to be revised based on changes in orientation of a player.

Since orientation is a part of posture, measurement and display of orientation is useful in training correct sports posture. Taking orientation into account in the display would provide better feedback to the player regarding his or her orientation.

Measurement of player orientation may be used in determining certain measurement parameters, such as reaction time and first step quickness.

Measurement of orientation allows for calculation of rotational accelerations. Rapid, properly timed accelerations of the body center (the hips) are essential in many sports for speed and power development. As is known from the martial arts, rapid twisting of the hips is essential for both effective movement and power generation. First step quickness may be redefined as an acceleration of the player's hips (translational or rotational) in the correct direction.

Measurement of Upper Extremity Movements

Figure 23:
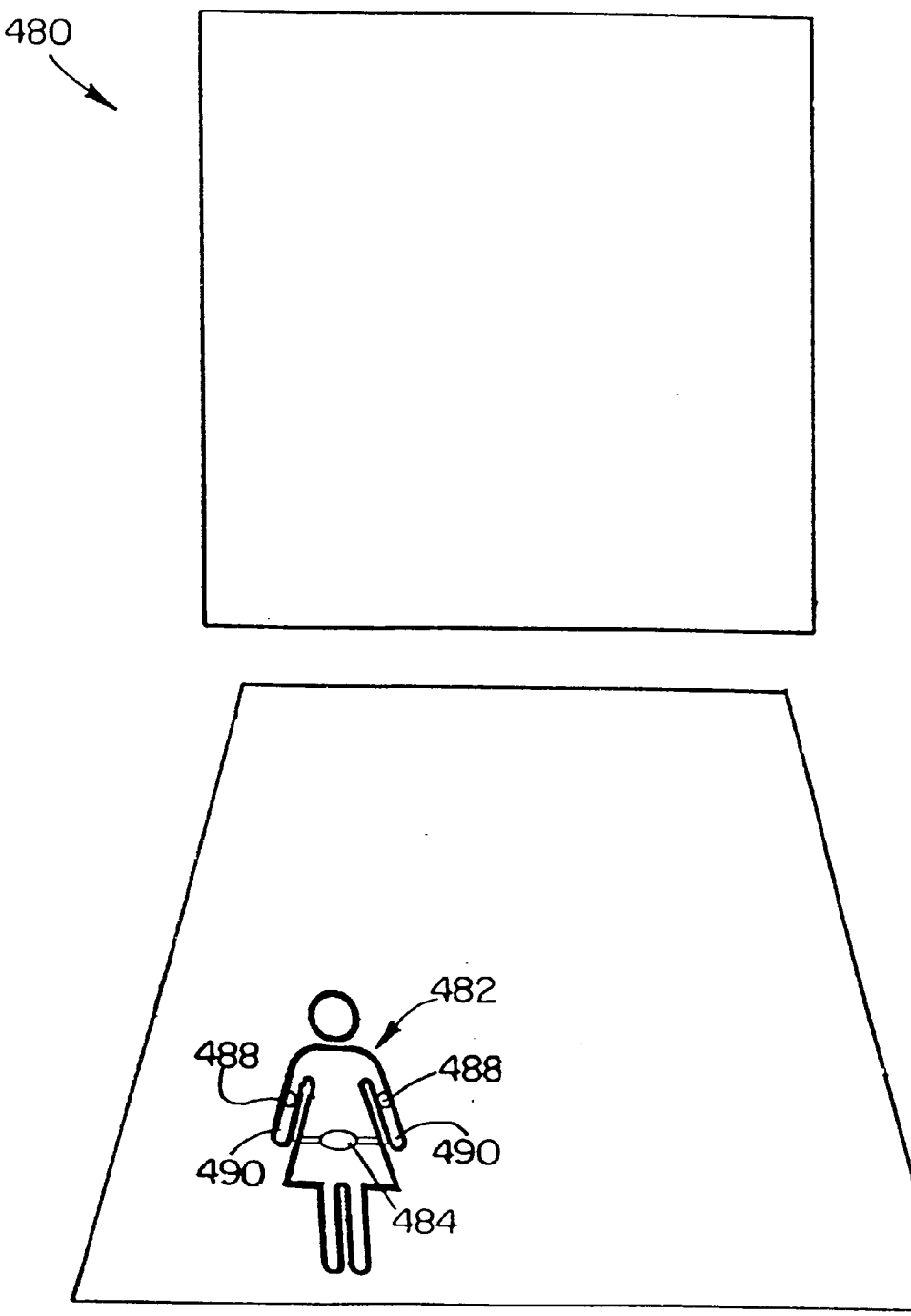
FIG. 23 is a perspective view of an alternate embodiment of the present invention which tracks the position of a player's upper extremities.

Referring to FIG. 23, a training system 480 is shown that tracks movement of upper extremities (arms) of a player 482. The player 482 wears a beacon or reflector 484 for tracking whole body motion, as is described for many of the embodiments above. Additionally, the player has an upper beacon or reflector 488 on each of his or her upper extremities 490. The upper beacons 488 may be placed on the upper or lower arms, on the wrists, or on the hands, as desired. A tracking and display system similar to those described above is used to track and display motion of the upper extremities and of the whole body.

Tracking of movement of upper extremities provides enhanced simulation in activities where movement of the upper extremities is important, such as boxing, tennis, handball, and activities that involve catching or using the hands to move an object.

By use of the upper beacons 488 on one or both upper extremities, measurements may be extracted related to the player's ability to react, initiate and coordinate his or her upper extremities. The ability to quantify such performance is valuable for sports enhancement (football lineman, boxers, handball players, etc.) and physical medicine (rehabilitation of shoulder and elbow injuries, etc.).

Specific parameters that may be measured or calculated taking into account upper extremity movements include: Dynamic Reaction Time (how quickly the hands respond to cues); Vector Acceleration (magnitude of the acceleration of the hands/arms); Synchronicity (ability of hands to follow interactive cues); and CardioVectors (heart rate relationship to work performed by the hands).

The training system 480 may be modified to additionally or alternatively track the lower body extremities, as by use of lower beacons on the legs, feet, hips, etc.

Movement Resistance

It is desirable to provide tactile and force feedback provide for enhancement of a virtual reality experience, allowing a subject or player to experience forces simulating those of the activities simulated in virtual reality. For example, if a weight is lifted in the physical world, the subject feels a resistance to the movement (due to its weight).

Figure 24:
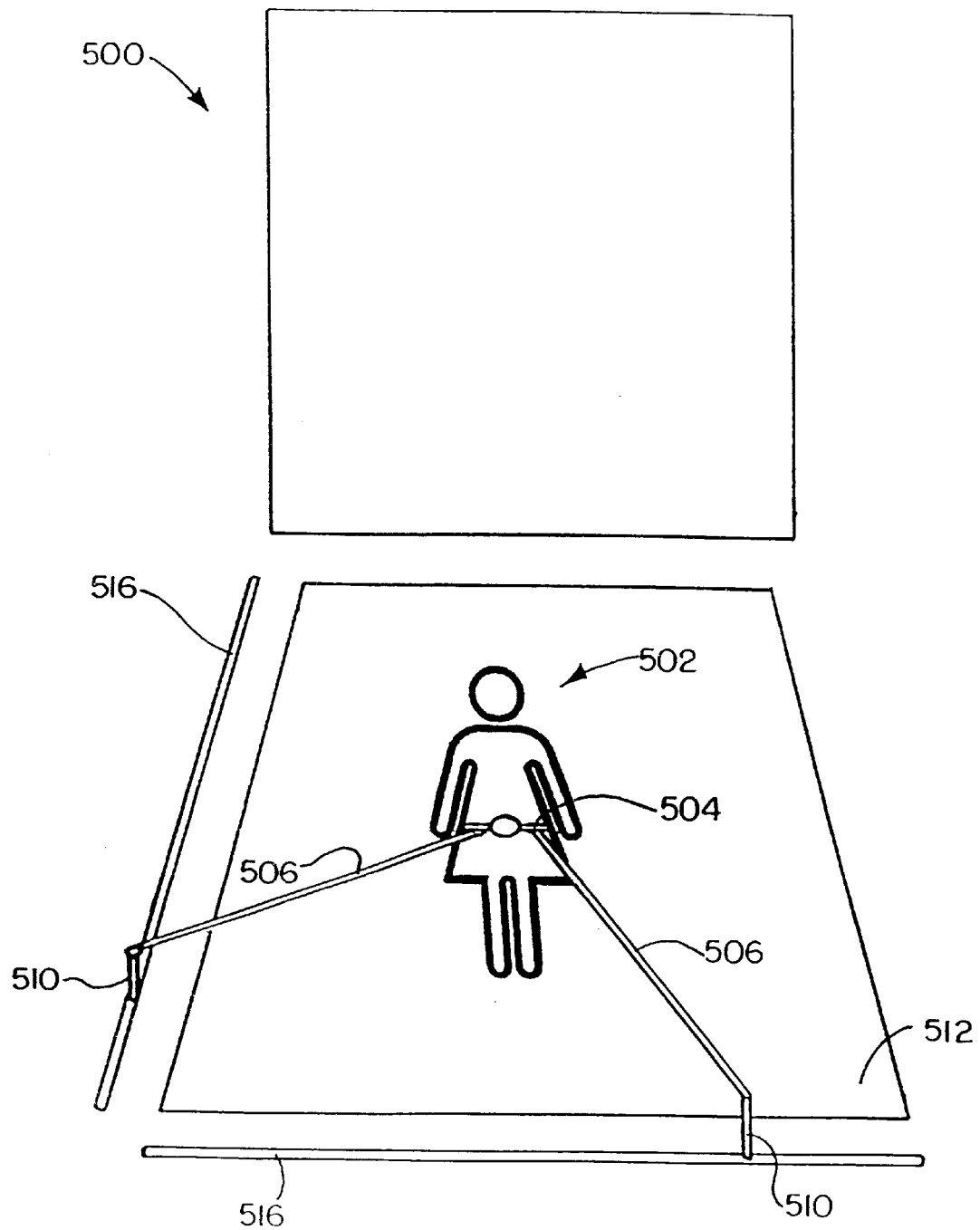
FIG. 24 is a perspective view of an alternate embodiment of the present invention which includes resistance devices that oppose player motion.

Referring to FIG. 24, a training system 500 is shown that includes means to provide physical resistance to movements of a player or subject 502. The tracking and display components of the training system 500 are similar to those described further with respect other embodiments, and such description is not repeated for this embodiment.

The player 502 wears a belt 504 around his or her waist. One end of each of one or more resistance devices 506 are attached to the belt. The resistance devices 506 provide a force against which the player 502 must pull in order to move. As shown the resistance devices 506 are elastomeric or elastic bands which provide an opposing force as they are stretched. The other end of the resistance devices 506 are attached to posts or stakes 510, which are preferably outside of the physical space 512 on a floor (as shown), or on a wall or ceiling. As shown in FIG. 23, the posts or stakes 510 may slide freely in slots 516 outside of the physical space 512.

The resistance devices 506 thus provide resistance to movement of the player 502. As the player moves within the physical space 512, one or more of the resistance devices 506 is stretched. This stretching produces a force on the player 502 opposing his or her motion. This opposing resistance acts to progressively overload the subject or player in each movement plane, thereby accelerating progress due to well-known principles of athletic training.

Other suitable resistance devices include springs and gas-filled cylinders, as well as cords sold under the trademark SPORT CORDS.

Preferably, resistance devices would be provided for all three planes of movement (X, Y, Z). Resistance devices for providing resistance in the Y-direction (resistance to jumping or leaping) may be anchored to the floor in the vicinity of the player. Anchors for the resistance devices may be recessed in the floor.

It will be appreciated that resistance devices may be attached to the player at places other than the waist. For example, the resistance devices may be attached to lower and/or upper extremities to provide resistance to movement of specific parts of the body.

Additionally or alternatively, resistance devices with both ends attached to different parts of the body may be used. Such a device may be attached, for example, from arm to leg, from upper arm to lower arm, from upper leg to lower leg, from head to arm, from arm to waist, or from arm to other arm.

Use of resistance devices coupled with accurate measurement of location of the player or subject allows enhanced accuracy of sports results in more sports relevant movement patterns. The system 500 also allows quantification of the effects of added resistance both in real time and progressively over time.

The resistance devices may also be used to enhance the simulation by simulating the apparent conditions encountered by the virtual counterpart that the subject controls. For example, the resistance provided by the resistance devices may simulate the resistance the subject's counterpart experiences while treading through mud, snow, or waist deep water. With appropriate force feedback, the subject not only sees the forces acting on his or her counterpart, but actually "experiences" these forces in the physical world. Such resistance may be provided by one or more actuators such as piston-cylinder assemblies, motors, etc., connected to the player, the force exerted by the actuator(s) being controlled by the system to provide for a force feedback to the player or a force consistent with the virtual reality in which the player exists.

The resistance devices may also be used to provide handicapping in multiplayer games, with levels of resistance chosen to compensate for differences in skill between the players.

Tracking Movement in Conjunction With Use of Exercise Apparatuses

Figure 25:
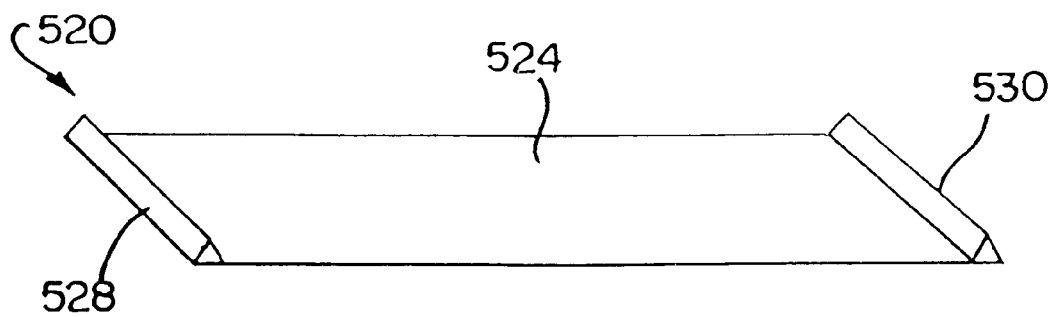
FIG. 25 is a perspective view of a prior art slide board.

The slide board is a widely used exercise apparatus which is used for conditioning and rehabilitation to help improve lateral movement, power, proprioception and endurance. As shown in FIG. 25, a typical slide board 520 has a flat, slippery sliding surface 524 with stops boards 528 and 530 on either end. A user uses a foot to push off the stop board 528, for example, glides or slides across the sliding surface 524, and then changes direction by pushing off the stop board 530 with the other foot. Slide boards are often used to simulate the physical demands of ice skating.

Figure 26:
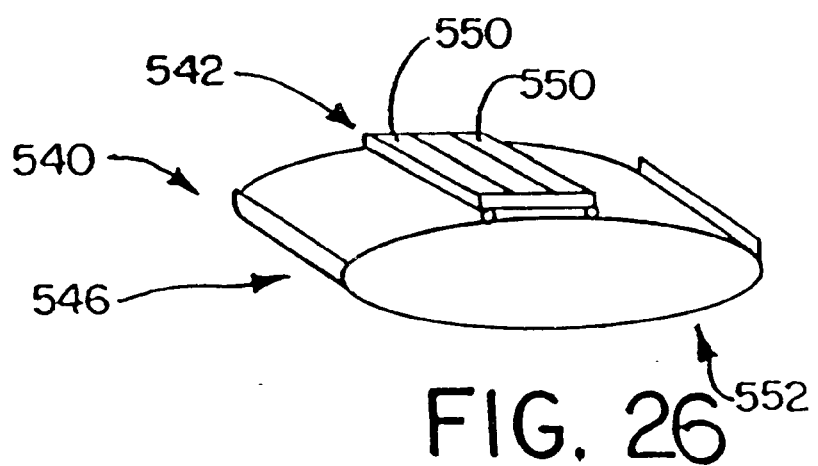
FIG. 26 is a perspective view of a prior art ski simulation device.

Another stationary exercise device involving back-and-forth movement is the ski simulation device 540 shown in FIG. 26. The device 540 has a tension-loaded skate 542 that glides laterally across an arc-shaped platform 546. The skate 542 has foot pads 550 thereupon for a user stand on. As the user moves back and forth, the skate 542 moves from side to side and the device 540 rocks back and forth on a curved or arcuate surface 552 of the platform 546. Such devices are used for improving balance, motor skills, endurance, and muscle tone for the lower body. An example of such a device is one sold under the trademark PRO-FITTER.

Figure 27:
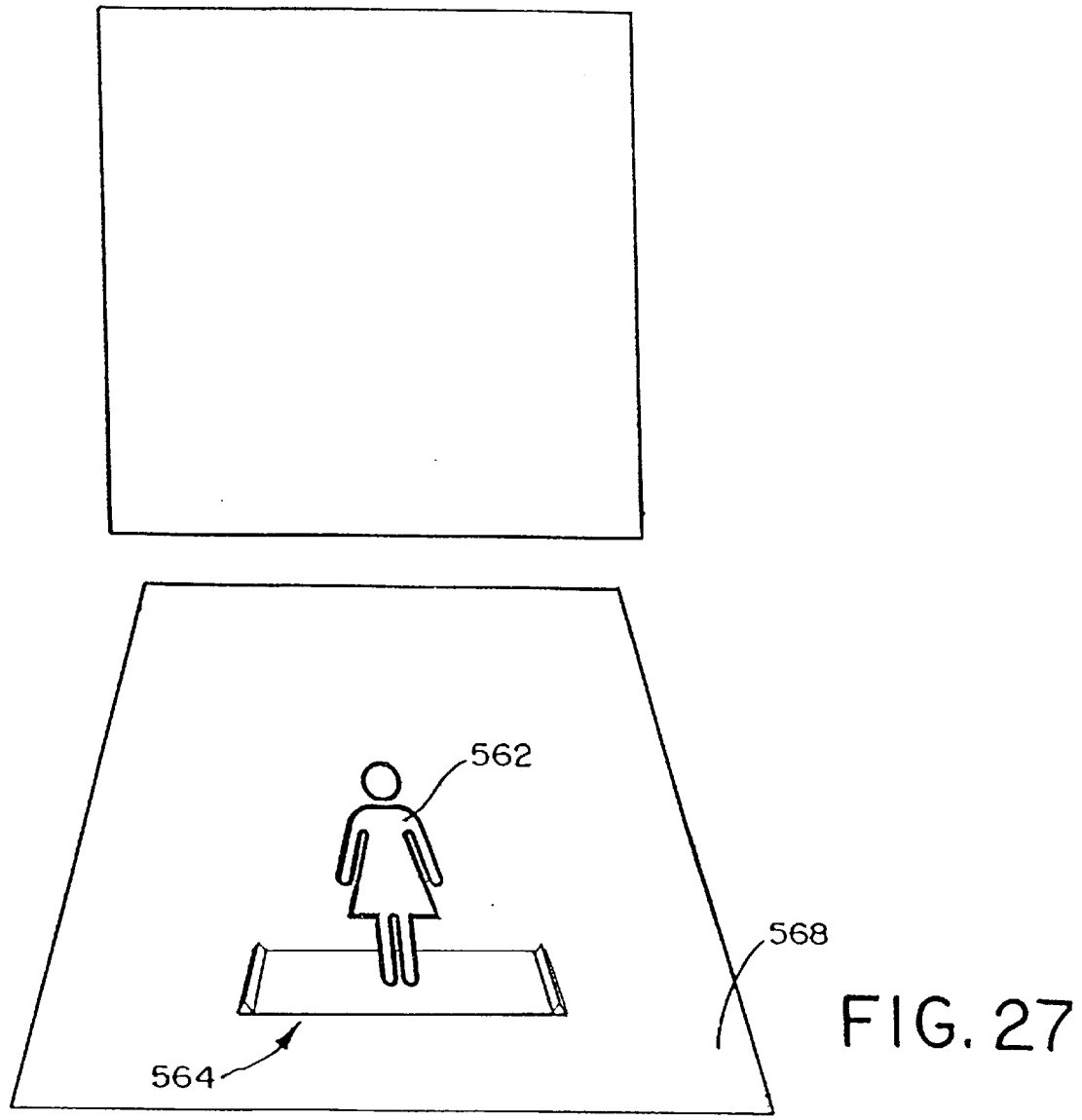
FIG. 27 is a perspective view of an alternate embodiment of the present invention which includes an exercise device used by the player.

The devices shown in FIGS. 25 and 26 may be used in conjunction with the tracking and display systems described earlier. Referring to FIG. 27, a training and simulation system 560 is shown. The system 560 has tracking and display components similar to those described earlier with regard to other embodiments. A subject 562 interacts with an exercise device 564 which is within in a physical space 568. The subject's movement is tracked and displayed. The devices shown in FIGS. 25 and 26 and described above are exemplary exercise devices. Such displaying may involve either first person or third person perspectives, both described above.

Measurement constructs such as the Dynamic Sports Posture construct described above may be used to analyze the movements of the subject 562.

A system such as the system 560 may be used to enhance the simulation of a w sports experience by displaying appropriate surroundings while using the exercise device 564. For example moguls, tree branches, other skiers, etc. may be displayed during a skiing simulation. The speed of apparent movement in the displayed virtual space may be tied to the speed of movement of the subject.

Reactive Power Training

Typical exercise programs incorporate two primary components—isolated limb/joint resistive training (strength training) and aerobic cardiovascular (CV) training. Though generally popular, such programs are considered inferior for those seeking improved functional or sport specific performance accompanied by substantial increases in lean body mass (more muscle).

One reason that such programs are considered inferior is neither of the traditional components meaningfully contributes to such core functional capabilities as balance, reaction time, agility and reactive power. The traditional strength training component of isolated joint/limb training component is designed to increase the amount of load that can be lifted, not to appreciably enhance the individual's ability to efficiently and, where required, explosively negotiate his or her environment. Strength training does not train the nervous system to efficiently work in conjunction with the muscle fibers to produce optimum functional performance.

Additionally, for those seeking the lean, muscular, powerful physiques of the elite sprinter, gymnast or body builder, the traditional aerobic CV component may be counterproductive. In his book Explosive Power & Strength, Dr. Donald Chu noted that "aerobic training has become a dominant component of most conditioning programs . . . . However, except in the early stages of their careers, aerobic training for strength and power athletes is out of the question. Aerobic training may help an athlete recover from high-intensity exercise, but it does so at the expense of speed and power and increases the risk of overuse injuries and overtraining. Endurance training is important, but . . . be certain that the type of endurance developed is specific to the sport."

Consequently, the most efficient and effective meaning of developing the lean powerful, functional bodies that many fitness club members covet, and that many athletes and seniors require, involves training for power. Power training, simply stated, is comprised of multiple, relatively brief bouts (periods) of high intensity exercise. For example, sprinters run at the fastest possible pace for a brief period of time—the result is significant muscle hypertrophy. By contrast, distance runners work at a sustainable pace, doing a nominal amount of work per unit of time. It is this specificity of training that produces the contrasting long, thin thigh muscles of the marathon runner and the highly defined, large muscles of the sprinter.

Figure 28:
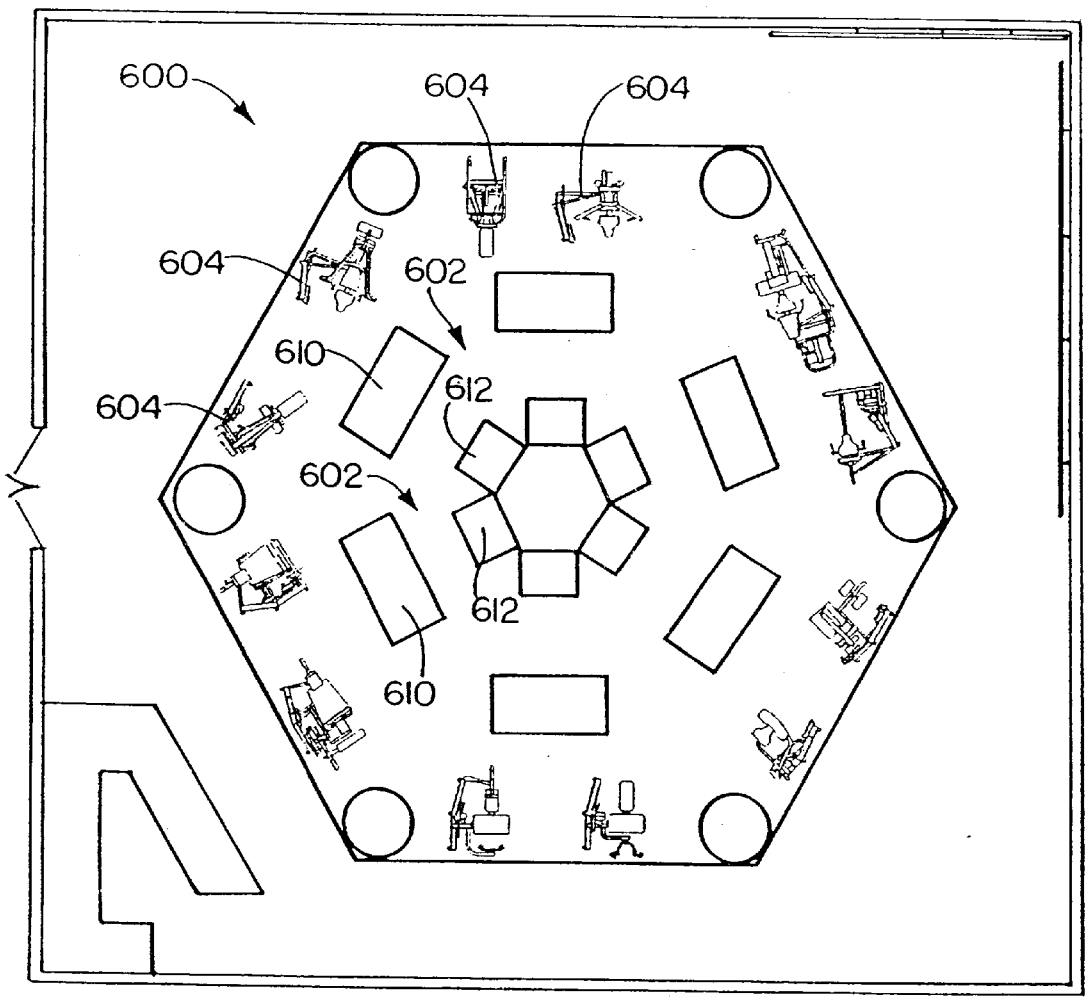
FIG. 28 is a plan view of a reactive power training system of the present invention.

Referring to FIG. 28, a reactive power training system 600 is shown. The training system 600 includes both reactive training devices 602 and strength training devices 604.

The reactive training devices 602 provide cues to a subject (also referred to as a user or player) to perform movements in response. For example, the reactive training devices may involve the subject attempting to mimic the movements of an avatar on a display screen. The cues are provided for numerous movements over a short period of time.

Preferably, the cues include prompts for numerous both planned and unplanned movement challenges. Preferably cues will be to elicit movements that elevate the subject's heart rate to a desired target zone. The cues may include auditory and/or visual cues.

The cues will preferably elicit movements in at least two dimensions. Examples of such two-dimensional movements include movement within a rectangular floor area, movement along a line combined with jumping, and movement along a line (such as by sliding) while maintaining a desired posture. It will be appreciated that there are many such other movements in at least two dimensions which may be cued by the reactive training device.

The reactive movements prompted by the reactive training devices may include training scenarios designed to enhance sports specific skills. For example, soccer skills may be enhance by engaging the user in a simulated soccer game.

As shown in FIG. 28, the reactive training devices 602 each include a physical space 610 and a tracking and display system 612. The tracking and display system 612 continually tracks the position of the subject during training. To facilitate tracking, the subject may wear a marker, such as a reflector, emitter, or beacon, the location of which is tracked by the reactive power device.

The marker may emit or transmit a signal which enables the reactive training system to identify a particular subject. For example, the marker may emit sound waves (either sonic or ultrasonic) or light waves (either visible or non-visible) that the reactive training system is able to associate with the particular subject. Thus within a single training session a user may be able to interrupt a particular reactive training scenario after a bout of reactive training, with the reactive training device able to later "recognize" the user and continue the scenario from the point of interruption.

Alternatively or in addition, the recognition of a particular user may be used to call forth a reactive training scenario or sequence particular to that user.

It will be appreciated that the marker may emit or transmit other information, such as the heart rate of the wearer. However, a heart monitor worn by the subject may have a separate telemetry system.

It will be appreciated that a user may be identified to a reactive training device by other means, such as by entry of identification number on a keypad or touch screen, or by insertion into the device of an object bearing indicia, such as a bar code or a magnetic medium, which identifies the user.

The numerous testing and training system embodiments described above are suitable for use as reactive training devices. Many of the features of the testing and training systems, such as providing real-time feedback to the subject or user, are desirable as well in the reactive training device.

It will appreciated that alternatively other devices that provide cues that elicit responsive movements from subjects are suitable for use as reactive training devices in the reactive power training system.

The reactive training devices may provide real-time feedback to the subject during use of the reactive power training device. The feedback may related to one or more of the constructs described above. For example, the feedback may be indicative of the subject's reactive power, with the feedback possibly including an indication of the subject's acceleration, velocity, or power.

Although as illustrated all of the reactive training devices are the same, it will be appreciated that all of the reactive training devices need not be identical. In addition, a greater or lesser number of reactive training devices may be employed.

Examples of suitable strength training devices include the Total Gym, Cybex or LifeFitness selectorized strength machines, BowFlex, free weight bars and dumbbells, pulleys, elastomeric cables, chin bars and the like. Preferably the strength training devices are capable of training various of the user's muscles. For example, some of the strength training devices may be directed to working the upper body muscles, while others may be directed to working the lower body muscles.

Figure 29:
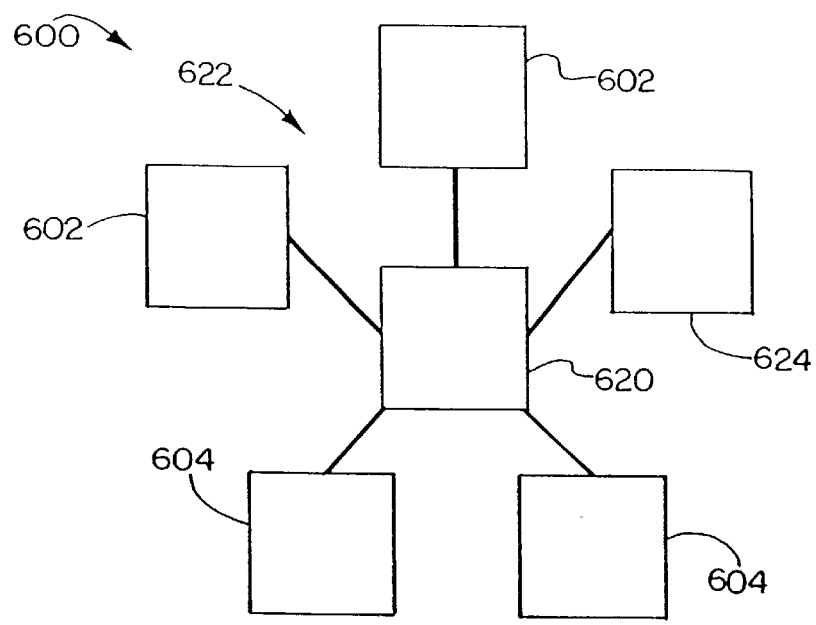
FIG. 29 is a schematic view of the network connections of the system of FIG. 28.

Referring to FIG. 29, the reactive power training system 600 includes a network administration computer 620 which is coupled to the reactive training devices 602 to form a network 622. The network allows information received at the reactive training devices (such as identification information or performance information) to be stored in a storage device 624 that is part of the network administration computer 620. This stored information may be accessed by any of the reactive training devices 602 in order to provide the user with cues appropriate for the user's desired exercises. In addition, the stored information may be used to modulate the cues based on the user's progress within a training session and between sessions.

The network administration computer 620 includes a data entry device 626 for entering and/or updating information in the storage device 624. Suitable data entry devices include keyboards, mice, touch screens, disk drives, and CD-ROM drives.

The strength training devices 604 may also be coupled to the network 622. Information about the strength training exercises performed (such as the number of repetitions, the weight, the distance traveled, and/or the setting of the machine) may thereby be transmitted to the storage device 624.

Information may also be sent along the network 622 to a suitable display included as part of each of the strength training devices 604. Such a suitable display may be integrally incorporated with the rest of the strength training device. Alternatively the display may be in the vicinity of the strength training device, alongside the strength training device, for example. The information sent may include the information regarding the exercises to be performed, and/or may include other information.

While the reactive power training system is preferably networked as described above, it will be appreciated that reactive power training system may in whole or in part non-networked. For example, information regarding the exercises performed on the strength training devices may be recorded manually, with the information later entered into the networked storage device.

During the recommended two to three reactive power training sessions per week, a subject follows a training sequence which preferably alternates between 30 to 120 second bouts (periods) of exercise on reactive training devices 602, and resistive strength enhancing activities on the strength training devices 604. These highly stimulating, engaging training sessions can be completed in approximately 35 to 50 minutes. It is believed that resistive strength training prepares (fires up) the muscle fibers prior to reactive training to create a state where the neuromuscular system is most receptive to growth.

Thus use of the training system 600 transforms the strength and power developed through isolated joint/limb training into truly functional reactive power. It develops the type of CV fitness that leads to enhanced sports performance for sports demanding repetitive explosive movement. Further, it provides a time efficient, entertaining means of creating a well-defined, powerful physique.

The reactive training devices 602 direct the flow of tasks over each training session, and over a series of the user's training sessions. For example, after a suitably-timed bout of exercise on the reactive training device the user may be prompted to proceed to a specific strength training device. Such a prompt may be coupled with other information, for example information regarding the performance of the just-completed bout of exercise.

The network administration computer 620 may be programmed to direct users so that the strength training devices 604 are used efficiently. For example, the network administration computer may be programmed to send a user to a strength training machine which is currently unused, if the unused machine is part of that user's training sequence and has not yet been used by that user in the present training session.

There is a valuable synergistic effect derived from of power reactive training. It is widely known that significant benefits to the cardiovascular system are derived from exercise that elevates the subject's heart rate to the targeted zone for a period of approximately 20 to 40 minutes. Preferably the bouts of reactive training are sufficiently strenuous to maintain the user's heart rate in the target zone during the resistive strength training that occurs between bouts of reactive training. As one purpose of the present invention to develop reactive power, it is desirable for the CV training component (here use of the reactive training devices) to contribute to the subject's ability to function successfully during anaerobic power activities. Further, the CV component ideally create a training environment (situation) that replicates the type of muscular contractions and anxiety that the subject will actually encounter in competition or demanding work environment.

Exercise scientists and coaches have searched for a single variable that could accurately characterize both performance and fitness.

Currently, a subject's overall performance fitness must be characterized by a number of performance variables. These variables may include measures of lower and/or upper body strength, aerobic or anaerobic endurance, speed or the like. Few of these measures share a common denominator that would allow comparison between all training components.

With Reactive Power Training, there is one variable that is descriptive of the exercise components that comprise the program. This single variable, power, is the common denominator that enable accurate assessment of the benefits a subject derives from both isolated limb strength training, as well as the benefits derived from sport specific movement training.

Current measures of progress do not provide such a global measure. Measures of isolated joint strength, i.e., a bench press or squat for example, are not reflective of functional movement capabilities. Current core tests for athletes measure the amount of load that can be lifted or how fast they can run. As such, these tasks are specialized strength and speed measures and are not reflective of the subject's ability to move with power and skill amidst his or her environment. Most often, no indication of movement skills is provided—balance, speed, coordination, agility, perception, recognition, cognition, etc. are all left unmeasured.

The present invention can quantify isolated limb power, which contributes to the ability to move with skill and power, as well as reactive power, which is the ability to actually move with skill and power. The above-described reactive power training system is uniquely capable of measuring reactive power.

By monitoring the activities of the subject while performing tasks that are reflective of that individual's skill domain, dynamic (reactive) power can be quantified. For an athlete, this entails sport specific tasks, with the measurement location being the kinematic description of movements of the pelvis during execution within a computer simulation. Consequently, both isolated limb strength and power are quantified, as well as dynamic power.

For the reasons given above, it is preferable that strength training and reactive training be co-mingled and alternated within the same training session. However, it will be appreciated that a serial approach to training may be used. In such an approach most of all of the strength training is done either before or after the reactive training.

Real Time Segmented Feedback

Movement challenges created for the player by movement of the virtual; opponent or avatar may include many relatively short, discrete movement segments or legs. These segments may prompt movement amounting to only a few inches of movement of the player's center of mass. These segments may be without fixed start or end positions. However, start or end positions may be approximated, for example, by positions where the player changes direction, or by movement of the player a given distance away from a position where he or she was at rest.

In achieving maximal performance gains, it is beneficial for the player to be given sensitive, real time, accurate feedback. It is preferable for real time feedback to be provided to the player very soon after his or her completion of each movement segment, regardless of the segment distance (generally detected as a core displacement of the player's center of mass).

The present invention includes calculation of performance values (based for example on the parameters described above) by continuously sampling positional changes in at least two planes of movement, and preferably in three planes of movement.

On Screen Display of Performance Parameters

Figure 30:
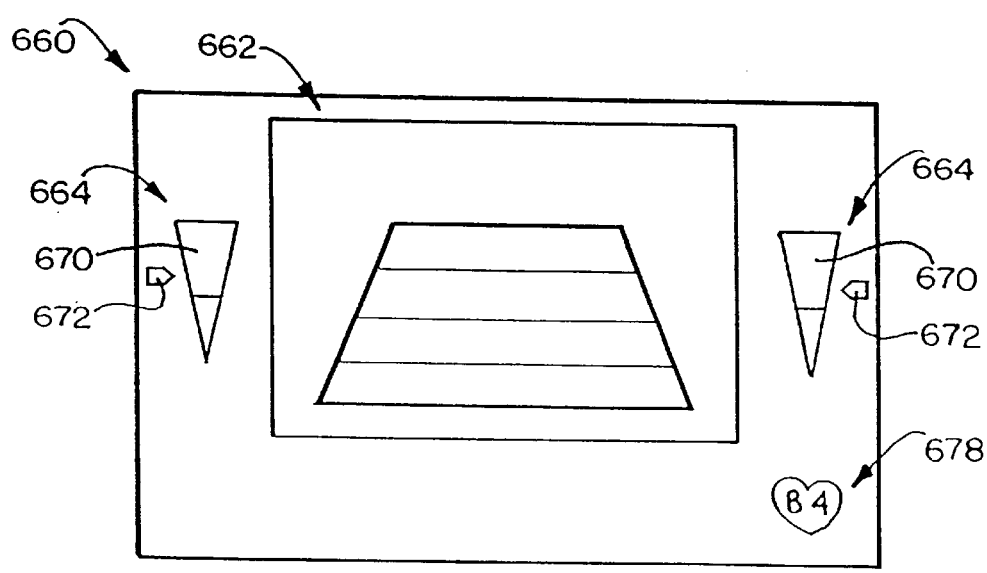
FIG. 30 is a representation of a screen display of a testing and training system of the present invention.

FIG. 30 shows a monitor or display 660 which provides feedback to a player (or user or subject) using a testing and training system such as those described above. The monitor 660 may be similar to the monitor 28 described above.

In addition to a view 662 of virtual space, the monitor 660 also displays parameter indications 664 of one or more parameters.

The parameter indications 664 display information related to performance parameters such as those described above.

For example, the parameter indications may be useful in providing the above-described real time segmented feedback.

The relation to measured performance parameters may be direct, for example displaying an indication of the player's elevation. Alternatively, the relationship between performance parameters and the displayed information may be more attenuated. The displayed information may be of a derived or calculated parameter such as power. It may alternatively be of some "game score" which is an indication of one or more aspects of the player's performance.

The display of information in the parameter indications 664 is preferably graphical, although the information may additionally or alternatively be displayed in other ways, such as numerically. As shown, the information in each of the parameter indications 664 is represented graphically by changing the color of part of a displayed inverted triangle 670.

The scaling of the parameter indications 664 may be changeable, accommodating for example the differences expected in performance of different players, and the different movements expected in different types of testing and training scenarios.

The parameter indications 664 each include a flag 672 which provides an indication of the maximum value of the displayed parameter. For example, the flag for an indication of player elevation may display the maximum elevation of the player thus far. This elevation information is an important parameter for posture training, training a player to maintained a crouched position, for example. The elevation information is also useful, for example, for informing the player of his or her highest jump.

It will be appreciated that the parameter indications need not include flags, and may include additional flags. It will be further be appreciated that the flags may be used for a wide variety of other purposes, for example showing minimum parameter values.

The parameter indications 664 are preferably updated in real time, in order to provide the player with timely feedback on performance.

The monitor 660 also displays a heart indication 678 which indicates the heart rate of the player. The heart indication may be graphical or numerical, and may include an auditory signal, such as the simulated sound of a beating heart. The heart rate of the player may be measured and transmitted for display using a heart monitor such as that described above.

Learning Task Implementation

Tracking and display systems such as those described above may be employed for use in kinesthetic educational learning tasks. As mentioned earlier, some learners benefit from education utilizing kinesthetic processes, and it is expected that brain development is enhanced by simultaneously engaging different cognitive functions simultaneously. In addition, it is expected that learning may be enhanced by increases in the student's metabolic rate, such as increases in metabolic rate that result from the student's execution of learning task(s). Such increased metabolic rate may be due to an increase in the body's need, and subsequent delivery of, oxygen to support the production of energy in the body. It will be appreciated that increased metabolic rate due to increased activity can result in increased alertness. Thus increasing metabolic rate in a student can enhance a learning activity. However, numerous other factors—some as yet unidentified—for the observed enhanced learning state may be contributing.

Figure 31:
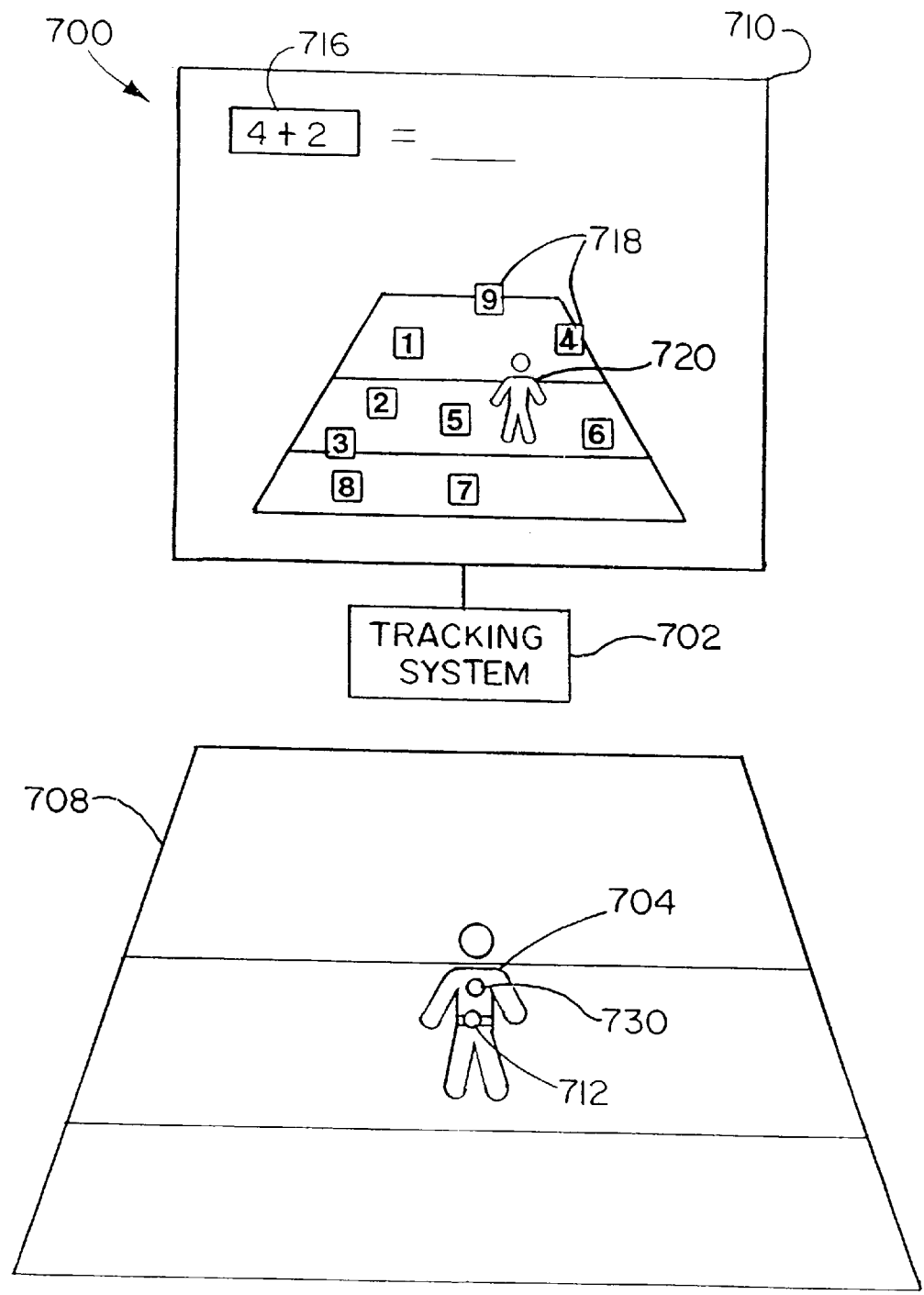
FIG. 31 is a representation of an interactive education system in accordance with the present invention.

Therefore, referring now to FIG. 31, an education system 700 is shown which synergistically enhances the learning process by including a kinesthetic approach to learning which preferably causes a heightened metabolic rate. The education system 700 includes a tracking system 702 for tracking a student 704 (also referred to herein as a "subject" or "person") as he or she moves in a defined physical space 708. The tracking system 702 is operatively coupled to a display 710 which displays information that prompts the subject 704 to engage in a cognitive learning task.

The term "cognitive learning," as used herein, is defined as learning which involves the attainment of abstract information which has general applicability outside of the learning task. Such information includes, for example, academic or scholastic material traditionally taught in schools. Examples of such academic information include multiplication tables and the content and order of the alphabet. "Cognitive learning" as used herein also includes learning other information, such as the steps of an industrial process. Cognitive learning broadly embraces learning involving mental concepts or skills, or speculative knowledge, which can be abstracted from the physical world and which has general applicability outside of the learning task.

The education system 700 prompts the student 704 to engage in full-body movement so as to raise his or her metabolic rate. Whole-body motion is an effective way of raising a person's metabolic rate (increasing oxygen consumption), as opposed to merely increasing the person's heart rate. It will be appreciated that several conditions other than core body movement may contribute to an increased heart rate which is not directly related to a proportional increase in metabolic rate or oxygen consumption. Anxiety and unresisted arm movement are two examples. A reflector or beacon 712, which may be similar to the reflector or beacon 38 described above, is provided on the subject or student 704 to enable the tracking system 702 to track him or her. This tracking allows the student's position within the physical space 708 to be monitored. Preferably the tracking is in three dimensions, as described above with respect to other embodiments. However, it will be appreciated that core body movement in two dimensions has the potential of elevating the metabolic rate to desired levels. Thus the student's performance could be monitored and quantified in a variety of ways.

Further, this tracking allows the movements of the student in the physical world to be connected to interactions in a virtual world, information regarding this interaction being communicated to the student by use of the display 710. The display and task may involve updating in real time a view of a virtual space, the updating being made in response to movements of the student or subject 704 within the physical space 708. The task may involve displaying cognitive learning elements, such as elements 716 and 718, on the display 710 for viewing by the subject 704. The task may also involve movement through the virtual space of a student icon 720 representing the subject or student 704. In the illustrated example movement of the student 704 within the physical space 708 causes movement of the corresponding student icon 720 within the virtual space displayed on the display 710.

The exemplary cognitive learning task in the illustrated embodiment involves the solving of arithmetic problems. The equation to be solved is shown as the cognitive element 716. The cognitive elements 718 are manipulable virtual objects bearing representation of possible solutions of the equation. These cognitive elements 716 are shown as positioned at various points in the virtual space, the positions in virtual space corresponding to positions in the physical space 708. The student 704 is able to manipulate one of the cognitive elements 718 within the virtual space by moving to a position in the physical space which corresponds to the position of the object in the virtual space. A change in the virtual location of the sensor 712 caused by a change in posture of the student 704, for example crouching or bending down, may be used as a signal for the system to display the student icon 720 as picking up the nearby cognitive element 718. The student 704 may then attempt to "solve" the equation by inserting the picked up cognitive element into the equation, in the virtual space. This may be accomplished for example, by moving to a location in the physical space 708 that corresponds to a preselected location in the virtual space, and/or by making a predetermined change in posture, for example by jumping.

It will be appreciated that the illustrated embodiment is but one example of the wide variety of cognitive learning tasks that may be accomplished. The educational system may be used to teach fundamental skills, such as the alphabet, colors, numbers, vocabulary, shapes and spatial relationships. More complicated information, such as math concepts, language and sentence structure, geography, and musical principles may also be taught using the system. The virtual environment may be represented as a traditional schoolroom or playground, for example, depicting objects and conditions associated with that environment, such as a chalk board or swing set, that serve as programmatic references or potentially active areas for activity selection and control. The virtual environment may also depict real or abstract environments, for example historical locations or maps, that transmit information that is to be learned by the student 704.

Preferably, the learning task described herein is progressive. Initially, the student is presented with problems/challenges that are easily solved through movement. Easily solved challenges allow the student to move more confidently and frequently which leads to an elevated metabolic rate. This increased metabolic rate enhances the learning state, thereby facilitating the student's efforts to solve progressively more difficult challenges. Over time, this progression become self perpetuating.

In another exemplary application, an educational game's primary goal is object recognition. The virtual environment depicts a playroom backdrop with familiar static objects, such as a bookcase, desk, and a centrally-positioned toy box. The student's viewing perspective for this environment, including his/her perceived distance from the objects, is chosen to evoke a sense of spaciousness and volume. The student's two-dimensional icon in the virtual environment may be, for example, an animated stuffed figure able to move within the confines of the area surrounding the toy box.

When the student is ready, virtual objects such as toys are animated and escape from the toy box by bounding out and skipping to various locations on the floor in the virtual environment. A teacher avatar visually and/or audibly instructs the student to return a specific one of the toy objects to the toy box. This instruction may involve, for example, stating the name of the object or showing a pictorial representation of the object. The student directs movements of his/her icon to the correct horizontal position of the requested toy object by moving his/her position in the physical space in the real world. The real world movements are mapped to movements in the virtual world or environment, but are scaled to fit the view of the display.

The student's icon may be represented as grabbing the toy when the student's icon is sufficiently close to the virtual toy object, and when the student for example sufficiently lowers his/her vertical body position. This lowering of vertical body position may be represented in the display by an animation sequence which shows the icon performing a proper kneeling down technique.

The education system may combine informational learning with physical training by for example examining the position, velocity and acceleration of downward movement to data for a similar type of movement accomplished with proper technique. The student may be required, for example, to repeat such a physical movement if it is not sufficiently close to the proper technique for such a movement.

When the student rises from the lowered body position, the toy object is displayed as being in the student icon's hands. Once the student icon possesses the toy, the student moves toward the toy box. When the student icon reaches the toy box, the toy is released into the toy box. The teacher avatar may then voice a congratulatory response and identify the next toy object to be retrieved. The game score for such an activity may be based, for example, on correct identification of the toy objects and the time required to complete the activity. The educational task may thus involve use of characters or avatars in the virtual environment which instruct or otherwise interact with the student and/or his/her icon. Cues or other feedback to the student regarding movements within the virtual environment or performance of the task may be auditory and/or visual.

It will be appreciated that performance criteria, such as those described in detail above with regard to other embodiments of the invention, may be used to quantify movement of the student while performing the educational task.

It will be appreciated that the above-described educational simulations, tasks, or other challenges, involve both the student's mind and body in interactive activities that elevate the metabolism, thereby contributing to a heightened state of educatability. The activities also synergistically engage the student's capacity to learn kinesthetically, by involving core body movements as part of the task.

A number of factors may be responsible for the enhanced ability to learn while the metabolism is elevated. For example, physical activities that elevate the metabolism increase blood flow to the brain and increase core body temperature. As blood flow is increased, hemoglobin releases oxygen more readily at higher temperatures. Additionally, facilitative nerve transmission also may occur at the higher core body temperatures caused by higher metabolic rates, thereby potentially assisting in improving reaction time.

It will further be observed that the increased metabolic rate is achieved by physical movements which are part of the educational task. By combining the physical movements and the educational task together, a synergistic effect may occur which enhances the learning state or capacity of the student when compared with elevations of metabolic rate due to secondary physical tasks which are not integrally part of an educational task (e.g., reading a book while riding a stationary bicycle). The education system 700 preferably involves activities which integrate the body (by physical activity), the mind (by cognitive learning), and the spirit (by entertaining, engaging experiences). However, it will be appreciated that, if desired, the educational activities may be wholly or in part uncoupled from the physical activities which raise the metabolic rate.

A metabolic rate monitor 730 may be used to monitor the metabolic rate of the student 704. Information from the metabolic rate monitor may be used to adjust the educational task to maintain the student's metabolic rate at a desired elevated level. For example, the pace of an educational task may be speeded up or slowed down to raise or lower the student's metabolic rate. It will be appreciated that other aspects of the educational task or challenge may be modified to make it more or less physically demanding, as required to maintain the desired elevation of metabolic rate.

An exemplary metabolic rate monitor is a heart rate monitor. It will be appreciated, however, that the practice of measuring heart rate to determine aerobic exercise intensity relies on the assumption that metabolic rate and heart rate are related. As noted above, several conditions may contribute to an increased heart rate which is not directly related to a proportional increase in metabolic rate or oxygen consumption. Anxiety and unresisted arm movement are two examples. Therefore the use of a heart rate monitor as a metabolic rate sensor is connected to the use of core body movements to raise the metabolic rate, as described above. The heart rate monitor may be the same or similar to that as described above with regard to earlier embodiments.

Educational Game Implementation

What follows is an example embodiment of an educational game employing a continuous tracking system available from Arena, Inc. under the trademark TRAZER. It will be understood that this embodiment is merely exemplary, and is not meant to be limiting.

Create a suitable 2D or 3D virtual environment or viewing surface database using Autodesk 3D Studio or similar industry-standard design tool. The database is comprised of graphical objects, surface textures, view properties, and lighting management description that together creates familiar cueing regularly employed by current educational computer games. For example, the virtual environment may be represented as a traditional school room or playground, depicting objects and conditions associated with that environment, such as a chalkboard or swing set, that serve as programmatic reference or potentially active screen areas for activity selection and control. The choice of virtual environment is not limited in scope according to real-world possibilities, but may depict fantasy places or historical locations. Regardless of thematic content, the virtual environment serves to promote and coordinate the desired learning objectives, while maintaining a consistent and suitable presentation for the intended student's age level.

Next create suitable 2D or 3D graphical animations and/or static 2D surfaces, that include menus, text, backdrops, and other bitmap operations that serve to instruct, guide, enhance or encourage the desired progression through the activities. The animation sequences are created using Autodesk 3D Studio or similar industry-standard animation design tool. The 2D surfaces are created using JASC Paint Shop Pro or similar industry-standard graphics design tool. The animation sequences may include a primary character or avatar that instructs the student on game play by demonstrating proper body movement and positioning. Or the animation sequences may be less interactive and secondary to the primary educational task, such as scrolling performance report cards on progress, or inanimate objects that "come alive" and perform brief and amusing monologues and actions as a personification of its intended educational function.

When utilized as the primary or secondary visual feedback under control of TRAZER, these graphical environments and objects require real time manipulation and/or translation within the virtual environment. A suitable 2D and 3D graphics engine is required to facilitate this control, such as Image Space, Inc.'s CUBE Technology or similar industry-standard 3D graphics engines. The suitable 3D graphics engine implementation is fully optimized in Pentium and Pentium MMX 32-bit mode, for both Win32 and extended DOS environments. The suitable 3D graphics engine is capable of 6 degree-of-freedom polygon-based 3D graphics rendering, providing both texture-mapped and solid-color rendering, and supports the latest 3D graphics acceleration hardware, including Real3D StarFighter AGP or compatible manufacturer. The suitable 2D graphics engine implementation supports full-functionality BITBLT in supported video modes for both Win32/Direct X and extended DOS environments. CUBE Technology offers a library of functions characteristic of a 3D graphics engine for the application w design, in the form of a proprietary application programming interface (API).

Once the graphical elements are completed the application program is designed utilizing Microsoft Visual Studio C/C++ development environment or similar industry-standard C/C++ development tools. In part, the application program describes the methods in which the graphical 2D/3D environment database is loaded and manipulated, including animation and light management, graphical object instantiation and control, view port settings, sound effects, frame buffer control, bitmaps and texture maps location, etc. To elicit the desired educational objective through core body movement, TRAZER's proprietary API is fully supported and integrated into the programmatic control of the game and/or kinematic control of the graphical object(s) representing the student within the virtual environment. TRAZER reports the student's real world position coordinates, which the game's program reinterprets as screen coordinates associated to a particular graphical object or group of objects.

Additionally, TRAZER numerically derives the student's instantaneous velocity and acceleration components of movement that are used by the game to ascertain certain performance criteria required by a specific type of movement. For example, the game may require the student move continuously from starting location to end location without hesitation. Simply measuring total distance between starting and end location and transit time to derive speed would not convey subtle details regarding body position along the movement path. The student may have abruptly accelerated towards his/her target, but then briefly stopped then started again due to lack of confidence or indecision. Another student may have quickly moved along a more convoluted, zig-zag path towards his/her target. And a third student may have less quickly followed the ideal straight line path to the target. In all examples, a simple speed calculation may have shown the same results, betraying the obvious differences in technique and ability. TRAZER's instantaneous velocity and acceleration measurements allow the game to more accurately evaluate movement technique when proper technique is crucial to satisfy the game's objectives.

The primary programming task is to utilize the CUBE and TRAZER's APIs library functions within the application to cause the student to move in a prescribed manner through visual and auditory feedback in order to successfully achieve a certain educational objective.

For example, an educational game's primary goal is object recognition. The virtual environment is designed that depicts a playroom backdrop with familiar static w objects, such as a bookcase, desk, and a centrally positioned toy box. The student's viewing perspective of this environment, including his/her perceived distance from objects, is defined to evoke a sense of spaciousness and volume. The student's 2D avatar is represented in this virtual environment as an animated stuffed figure that can move within the confines of the area surrounding the toy box. Since the student's viewing perspective does not allow visual examination of his/her avatar from the side or top, a 3D animation is unnecessary.

When the student is ready, A random number of 2D toys are momentarily animated and escape from the toy box by bounding out and skipping to various locations on the floor. A teacher avatar visually and/or audibly presents a copy of the toy object that the student should find and return to the toy box as quickly as possible. The student directs the movements of his/her avatar to the correct horizontal position of the requested toy by moving his/her position in the real world. The real world movements are mapped in the same Cartesian axis orientation as in the virtual world, but scaled to fit the smaller view port of the video screen. The program compares the convergence of the toy and student's avatar horizontal plane coordinates and indicates correct positioning by employing a different avatar and/or toy animation sequence.

The student's avatar grabs the toy when the student sufficiently lowers his/her vertical body position, which action the program interprets as a correct response and changes the student's avatar animation sequence to demonstrate the proper kneeling down technique. The program examines the position, velocity, and acceleration of downward movement by real time comparison to a stored template file consisting of sequential time slices of position, velocity, and acceleration data of the same technique performed correctly. The program qualifies the technique using a windowed difference threshold comparison on sample-by-sample basis. A tolerance violation requires the student to repeat the movement to continue.

When the student begins to rise from this position, the original toy animation is removed from the screen and now the student's avatar displays the toy in hand. Once the student's avatar possesses the toy, the student moves towards the toy box. When the student's avatar reaches the toy box, the toy is released into the toy box. The teacher avatar voices a congratulatory response and presents the next toy. The game proceeds until all the toys have been returned to the toy box. A score is awarded based on correct identification of the toys and time to complete the activity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of educating comprising:
    prompting a person to engage in body core movement which elevates the person's metabolic rate; and
    prompting the person to engage in a cognitive academic learning task while the person's metabolic rate is elevated,
    wherein the prompting to engage in a cognitive academic learning task includes displaying a view of a virtual space, and
    wherein the promoting to engage in body core movement and the prompting to engage in a cognitive academic learning task both include promoting the person to engage in a body core movement cognitive academic learning task.

2. The method of claim 1, wherein the prompting to engage in a body core movement cognitive academic learning task includes tracking an overall physical location of a person within a defined physical space; updating in real time a virtual location corresponding to the physical location of the person; updating in real time the view of the virtual space; and displaying the view in real time.

3. The method of claim 2, wherein the prompting to engage in a body core movement cognitive academic learning task further includes updating the location of a virtual protagonist icon in the virtual space.

4. The method of claim 2, wherein the updating a view includes updating a first person perspective view of the virtual space from the virtual location.

5. The method of claim 2, wherein the displaying the view includes displaying cognitive learning elements.

6. The method of claim 1, wherein the prompting to engage in a body core movement cognitive academic learning task includes delivering cognitive learning challenges to the person by a computer.

7. The method of claim 1, wherein the prompting to engage in a body core movement cognitive academic learning task includes prompting the person to engage in interactive challenges that involve manipulation of objects in a virtual world by body core movement of the person in a defined physical space.

8. The method of claim 1, further including ascertaining the degree of metabolic rate elevation.

9. The method of claim 8, further including adjusting the prompting to engage in body core movement to maintain the metabolic rate elevation at a desired level.

10. The method of claim 8, wherein the ascertaining the degree of metabolic rate elevation includes monitoring the person's heart rate.

11. The method of claim 10, wherein the monitoring the person's heart rate includes monitoring the heart rate using a sensor worn by the person.

12. An interactive education system comprising:
    a continuous tracking system for determining changes in an overall physical location of a person, in a defined physical space; and
    a computer operatively coupled to the tracking system for updating in real time a virtual location in a virtual space corresponding to the physical location of the person in the physical space, and for updating a view of the virtual space,
    wherein the view includes cognitive academic learning material; and
    wherein the tracking system and the computer provide an interactive academic educational challenge wherein movement of the body core of the person in the physical space causes manipulation of objects in the virtual space.

13. The method of claim 12, further comprising a display operatively coupled to the computer for displaying the view.

14. The system of claim 12, further comprising a metabolic rate monitor worn by the person and operatively coupled to the computer.

15. The system of claim 14, wherein the metabolic rate monitor is a heart monitor.

16. An interactive education system comprising:

means for elevating a person's metabolic rate by prompting body core movement of the person; and means for engaging the person in a cognitive academic learning task while the person's metabolic rate is elevated, and wherein the means for engaging includes, along with the means for elevating, means for prompting the person to engage in a body core movement cognitive academic learning task.

17. The system of claim 16, further comprising means for ascertaining the person's metabolic rate.

18. The method of claim 1, wherein the prompting the person to engage in a body core movement cognitive learning task includes progressively prompting the person, such that the person is initially presented with challenges that are easily solved through movement, and is thereafter presented with progressively more difficult challenges.

* * * * *